United States Patent
Onoda et al.

[11] Patent Number: 6,127,541
[45] Date of Patent: Oct. 3, 2000

[54] IMIDAZOQUINAZOLINE DERIVATIVES

[75] Inventors: Yasuo Onoda; Yuji Nomoto; Tetsuji Ohno, all of Shizuoka; Koji Yamada, Sagamihara; Michio Ichimura, Mishima, all of Japan

[73] Assignee: Kyowa Hakko Kogyo Co., Ltd., Tokyo, Japan

[21] Appl. No.: 09/065,061

[22] PCT Filed: Aug. 29, 1997

[86] PCT No.: PCT/JP97/03023

§ 371 Date: Apr. 27, 1998

§ 102(e) Date: Apr. 27, 1998

[87] PCT Pub. No.: WO98/08848

PCT Pub. Date: Mar. 5, 1998

[30] Foreign Application Priority Data

Aug. 30, 1996 [JP] Japan ................................ 8-230807

[51] Int. Cl.[7] .................................................. C07D 487/02
[52] U.S. Cl. .......................... 544/251; 544/60; 544/115; 540/575
[58] Field of Search .............. 544/251, 60, 115; 540/575

[56] References Cited

U.S. PATENT DOCUMENTS 5,661,147  8/1997  Machii et al. .......................... 514/218
5,679,683  10/1997  Bridges et al. ........................ 514/267

FOREIGN PATENT DOCUMENTS 0 635 507  1/1995  European Pat. Off. .
WO 95/19970  7/1995  WIPO .

OTHER PUBLICATIONS

J. Org. Chem., vol. 51, No. 5 (1986) 616–620.
J. Med. Chem., vol. 29, No. 6 (1986) 972–978.
J. Med. Chem., vol. 32, No. 10 (1989) 2247–2254.

Primary Examiner—John M. Ford
Attorney, Agent, or Firm—Fitzpatrick, Cella, Harper & Scinto

[57] ABSTRACT

Imidazoquinoline derivatives of the formula

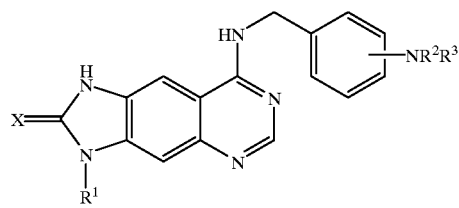

(wherein X may be O or S) provide selective cyclic guanosine 3',5' monophosphate (cGMP)—specific phosphodiesterase (PDE) inhibitory activity. The compounds are useful for treating or ameliorating cardiovascular disease such as thrombosis, angina pectoris, hypertension, heart failure and arterial sclerosis, as well as asthma, impotence and the like.

13 Claims, No Drawings

IMIDAZOQUINAZOLINE DERIVATIVES

FIELD OF THE INVENTION

The present invention relates to imidazoquinazoline derivatives or pharmaceutically acceptable salts thereof which have the cyclic guanosine 3',5'-monophosphate (cGNP)—specific phosphodiesterase (PDE)inhibitory activity and are useful for treating or ameliorating cardiovascular diseases such as thrombosis, angina pectoris, hypertension, heart failure, arterial sclerosis, as well as asthma, impotence and the like.

BACKGROUND OF THE INVENTION cGMP plays an important role as a second messenger in intracellular signal transduction. An inhibitor of cGMP-specific PDE, an enzyme which degrades cGMP, increases the concentration of intracellular cGMP, enhances the effects of endothelium-derived relaxing factor (EDRF), nitro vasodilator or atrial natriuretic peptide, shows the anti-platelet activity, the anti-vasocontraction activity and the vasodilating activity, and are useful for treating cardiovascular diseases such as thrombosis, angina pectoris, hypertension, congestive heart failure, post-PTCA restenosis, peripheral vascular diseases, arterial sclerosis etc., inflammatory allergic diseases such as bronchitis, chronic asthma, allergic asthma, allergic coryza etc., alimentary canal diseases such as irritable intestine syndrome etc., glaucoma, impotence and the like. The PDE inhibitory activity and the adenosine receptor antagonistic activity of imidazo[4,5-g]quinazoline derivatives are described in J. Med. Chem., 29, 972 (1986), J. Med. Chem., 32, 2247 (1989), J. Org. Chem., 51, 616 (1986) and the references cited therein. However, these compounds are neither particularly strong PDE inhibitors nor selective cGMP-specific PDE inhibitors.

Further, 8-anilino-2,3-dihydro-1H-imidazo[4,5-g]quinazoline-2-one derivatives are disclosed in EP635507. However, a substituent at 8-position in the compounds described in EP635507 is limited to an anilino group. Further, there is no description in EP635507 of the PDE inhibitory activity of the compounds.

In addition, 2,3-dihydro-1H-imidazo[4,5-g]quinazoline derivatives with cCMP-specific PDE inhibitory activity are disclosed in WO95/06648. However, in the case where a substituent at the 8-position in the compounds in WO95/06648 is aralkyl, a substituent in the aryl moiety of said aralkyl is limited to dialkyl-substituted amino such as dimethyl amino etc., lower alkyl, lower alkoxy, halogen and trifluoromethyl. There is no description therein of those compounds where the substituent in the aryl moiety of the aralkyl is monoalkyl-substituted amino or those compounds having cyclic amino groups such as morpholino, piperidino and thiomorpholino.

The PDE inhibitors known so far inhibit not only cGMP-specific PDE but also the cyclic adenosine 3',5'-monophosphate (cAMP) specific PDE which is an enzyme similar thereto, and therefore causes the elevation of the concentration of cAMP as well as intracellular cGMP and may cause side effects and the like. Further, the inhibitory activities thereof are not yet sufficient, and compounds which are more potent and selective are expected and desired.

DISCLOSURE OF THE INVENTION

The object of the invention is to provide imidazoquinazoline derivatives or pharmaceutically acceptable salts thereof which have potent and selective cGMP-specific PDE inhibitory activity, increases the concentration of intracellular cGMP, enhances the effects of endothelium-derived relaxing factor (EDRF), nitro vasodilator or atrial natriuretic peptide, shows the anti-platelet activity, the anti-vasocontraction activity and the vasodilating activity, and are useful for treating or ameliorating cardiovascular diseases such as thrombosis, angina pectoris, hypertension, congestive heart failure, post-PTCA restenosis, peripheral vascular diseases, arterial sclerosis etc., inflammatory allergic diseases such as bronchitis, chronic asthma, allergic asthma, allergic coryza etc., alimentary canal diseases such as irritable intestine syndrome etc., glaucoma, impotence and the like.

The present invention relates to imidazoquinazoline derivatives represented by formula (I):

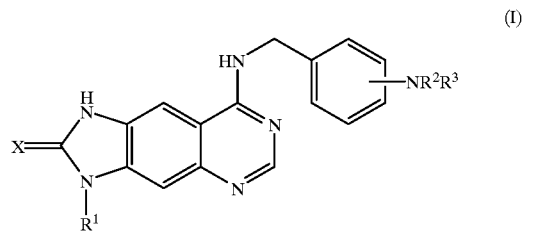

wherein $R^1$ represents hydrogen, substituted or unsubstituted lower alkyl, substituted or unsubstituted cycloalkyl, substituted or unsubstituted bicycloalkyl, substituted or unsubstituted tricycloalkyl, substituted or unsubstituted benzocycloalkenyl, substituted or unsubstituted lower alkenyl, substituted or unsubstituted aralkyl, substituted or unsubstituted aryl, or substituted or unsubstituted heteroaryl, $R^2$ represents hydrogen, substituted or unsubstituted lower alkyl, substituted or unsubstituted cycloalkyl, substituted or unsubstituted bicycloalkyl, substituted or unsubstituted tricycloalkyl, substituted or unsubstituted benzocycloalkenyl, substituted or unsubstituted lower alkenyl, substituted or unsubstituted aralkyl, substituted or unsubstituted aryl, or substituted or unsubstituted heteroaryl, $R^3$ represents hydrogen, substituted lower alkyl, substituted or unsubstituted cycloalkyl, substituted or unsubstituted bicycloalkyl, substituted or unsubstituted tricycloalkyl, substituted or unsubstituted benzocycloalkenyl, substituted or unsubstituted lower alkenyl, substituted or unsubstituted aralkyl, substituted or unsubstituted aryl, or substituted or unsubstituted heteroaryl, or $R^2$ and $R^3$ are combined to represent a substituted or unsubstituted N-containing heterocyclic group, and X represents O or S, or pharmaceutically acceptable salts thereof.

Hereinafter, the compounds represented by formula (I) are referred to as Compound (I). The same applies to the compounds of other formula numbers.

In the definitions of the groups of formula (I), the lower alkyl includes a straight-chain or branched alkyl group having 1 to 8 carbon atoms, such as methyl, ethyl, propyl, isopropyl, butyl, isobutyl, sec-butyl, tert-butyl, pentyl, isopentyl, neo-pentyl, sec-pentyl, tert-pentyl, hexyl, isohexyl, heptyl, octyl, and isooctyl. The cycloalkyl includes a cycloalkyl group having 3 to 8 carbon atoms, such as cyclopropyl, cyclobutyl, cyclopentyl, cyclohexyl, cycloheptyl, and cyclooctyl. The bicycloalkyl includes a bicycloalkyl group having 7 to 10 carbon atoms, such as bicylo[2.2.1]heptyl, bicyclo[2.2.2]octyl, and bicylo[3.3.1]nonyl. The tricycloalkyl includes a tricycloalkyl group having 9 to 12 carbon atoms, such as tricyclo[3.3.1.1$^{3,7}$]decyl, tricyclo[3.3.1.0$^{3,7}$]nonyl, and tricyclo[5.4.0.0$^{2,9}$]undecyl. The benzocycloalkenyl includes a benzocycloalkenyl group having 8 to 12 carbon atoms, such as benzocylobutenyl, indanyl and benzocyclooctenyl. The lower alkenyl includes a straight-chain or branched alkenyl group having 2 to 6 carbon atoms, such as vinyl, allyl, propenyl, methacryl, butenyl, crotyl, pentenyl and hexenyl. The aralkyl includes an aralkyl group having 7 to 15 carbon atoms, such as benzyl, phenethyl, benzhydryl and naphthylmethyl. The aryl includes phenyl and naphthyl, and the heteroaryl includes pyridyl, quinolyl, isoquinolyl, thienyl, furyl, pyrrolyl, benzothienyl, benzofuryl, indolyl, tetrahydroquinolyl, tetrahydroisoquinolyl and imidazolinyl. The hydroxy-containing lower alkyl includes a lower alkyl group substituted with 1 to 3 hydroxy groups, such as hydroxymethyl, 2-hydroyethyl, 3-hydroxypropyl, 4-hydroxybutyl, 3-hydroxybutyl, 2-hydroxybutyl and 5-hydroxypentyl. The N-containing heterocyclic group includes pyrrolidinyl, piperidino, piperazinyl, morpholino, thiomorpholino, homopiperazinyl, imidazolyl, 1-perhydroazepinyl, 1-perhydroazocinyl and tetrahydroisoquinolyl.

The substituted lower alkyl, substituted cycloalkyl, substituted bicycloalkyl, or substituted tricycloalkyl has the same or different 1 to 3 substituents such as cycloalkyl, hydroxy, lower alkoxy, hydroxyalkoxy, carboxy, lower alkoxycarbonyl, amino, monoalkyl-substituted amino, dialkyl-substituted amino, monoaryl-substituted amino, diaryl-substituted amino, nitro, halogen, substituted or unsubstituted heteroaryl, substituted or unsubstituted alicyclic heterocyclic group etc. The alkyl moiety of the lower alkoxy, lower alkoxycarbonyl, monoalkyl-substituted amino and dialkyl-substituted amino has the same meaning as the above-identified lower alkyl. The aryl moiety of the monoaryl-substituted amino and diaryl-substituted amino has the same meaning as defined above. The halogen includes fluorine, chlorine, bromine and iodine. The heteroaryl has the same meaning as defined above. Examples of alicyclic heterocyclic groups are tetrahydrofuryl, piperidino, piperidyl, morpholino, morpholinyl, thiomorpholino, thiomorpholinyl. piperazinyl, homopiperazinyl, pyrrolidinyl, imidazolyl and tetrahydroisoquinolyl. The substituent of the substituted alicyclic heterocyclic groups include the same lower alkyl, aryl or aralkyl as defined above. The substituted alicyclic heterocyclic group includes e.g. N-methylpiperazinyl, N-ethylpiperazinyl, N-methylhomopiperazinyl, N-phenylpiperazinyl and N-benzylpiperazinyl.

The substituted benzocycloalkenyl, substituted lower alkenyl, substituted aralkyl, substituted aryl, substituted heteroaryl, or substituted N-containing heterocyclic group has the same or different 1 to 5 substituents such as lower alkyl, hydroxy, the same hydroxy-containing lower alkyl as defined above, lower alkoxy, lower alkoxyalkyl, carboxy, lower alkoxycarbonyl, amino, monoalkyl-substituted amino, dialkyl-substituted amino, nitro, sulfonamide, halogen and trifluoromethyl. The alkyl moiety of the lower alkyl, lower alkoxy, lower alkoxyalkyl, lower alkoxycarbonyl, monoalkyl-substituted amino and dialkyl-substituted amino has the same meaning as the above-identified lower alkyl. The halogen has the same meaning as the above-identified halogen. Preferable examples of substituted N-containing heterocyclic groups are N-methylpiperazinyl, N-ethylpiperazinyl, N-methylhomopiperazinyl, N-phenylpiperazinyl, N-benzylpiperazinyl and benzylpiperidino.

The pharmaceutically acceptable salts of Compounds (I) include pharmaceutically acceptable acid addition salts, for example, inorganic acid addition salts such as hydrochloride, hydrobromide, hydroiodide, nitrate, sulfate, phosphate etc. and organic acid addition salts such as formate, acetate, benzoate, tartrate, maleate, fumarate, succinate, oxalate, glyoxylate, aspartate, methanesulfonate, benzenesulfonate etc.

Then, a process for preparing Compound (I) is described below.

Process 1-1

Starting Compound (VII) for preparation of Compound (I) can be prepared according to the following reaction steps.

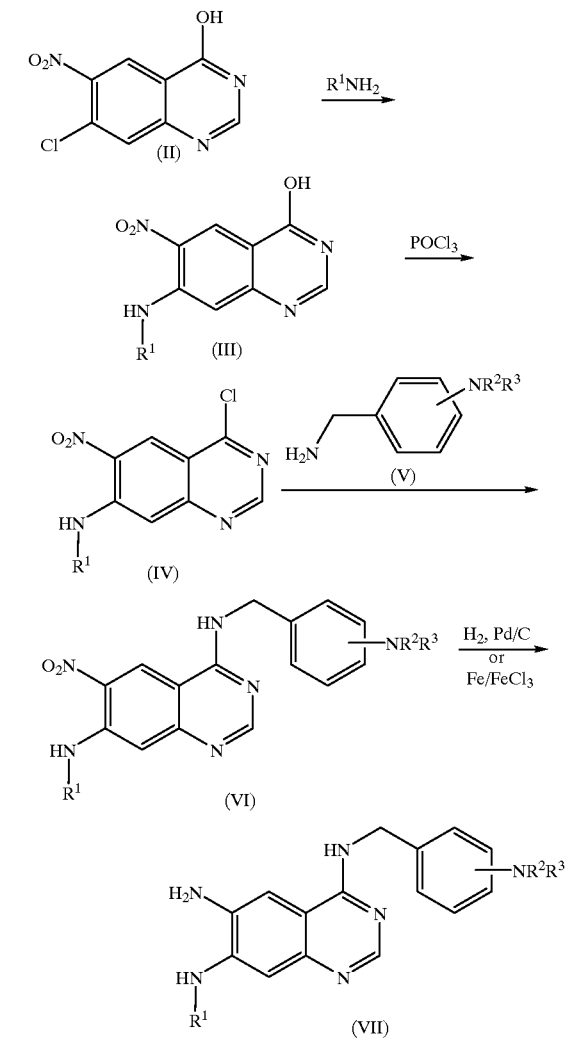

(In the formulae, $R^1$, $R^2$ and $R^3$ have the same meanings as defined above.)

Starting Compound (II) can be obtained according to the known process [J. Org. Chem., 40, 356 (1975), etc.].

Compound (III) can be obtained by reacting Compound (II) with one equivalent to an excess amount of an amine represented by the formula $R^1NH_2$ (wherein $R^1$ has the same meaning as defined above) or an aqeous solution thereof in a solvent such as ethanol, butanol or dimethylsulfoxide, if necessary using a sealed container (in a sealed tube), at room temperature to 150° C. for 1 to 24 hours.

Compound (IV) can be obtained by reacting Compound (III) with a chlorinating agent such as phosphorus oxychloride, thionyl chloride or phosphorus pentachloride, if necessary in the presence of a base such as triethylamine, N,N-diisopropylethylamine or pyridine without a solvent or in a solvent such as dichloromethane or 1,2-dichloroethane optionally containing N,N-dimethylformamide, at room temperature to the boiling point of the employed solvent in the presence of the solvent or at room temperature to the boiling point of the employed chlorinating agent in the absence of the solvent for 1 to 24 hours.

Compound (VI) can be obtained by reacting Compound (IV) with one equivalent to an excess amount of Compound (V) (wherein $R^2$ and $R^3$ have the same meanings as defined above), if necessary in the presence of 3 to 10 equivalents of a base such as triethylamine, in a solvent such as tetrahydrofuran, at room temperature to the boiling point of the solvent employed for 30 minutes to 24 hours. Starting Compound (V) can be obtained according to the processes described in Reference Examples or similar methods thereto. Compound (VI) can be subjected to the following reduction reaction after its $NR^2R^3$ was protected with a suitable protective group.

Compound (VII) can be obtained by catalytic reduction of Compound (VI) in the presence of a catalyst for catalytic reduction, such as palladium on carbon in an amount of 1/100 to 1/10 based on the weight of the substrate, in a solvent such as water, tetrahydrofuran, methanol, ethanol or N,N-dimethylformamide, in a hydrogen atmosphere or in a hydrogen stream, at room temperature to the boiling point of the solvent employed for 3 to 24 hours under stirring, or by reduction thereof in the presence of a reducing agent such as iron/ferric chloride or the like (ferric chloride is added in an amount of 1/100 to 1/10 based on the weight of the substrate, every 1 to 4 equivalents of reduced iron), in a solvent such as water-containing ethanol, water or the like at room temperature to the boiling point of the solvent employed for 1 to 10 hours under stirring.

Process 1-2

Compound (Ia) wherein X is O (oxygen) can be prepared from Compound (VII) as the starting material according to the following reaction step.

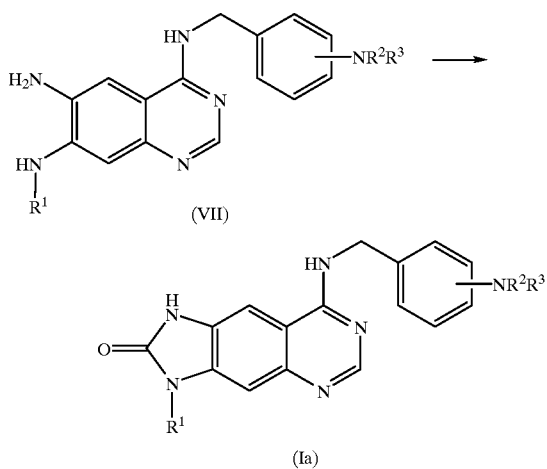

(In the formulae, $R^1$, $R^2$ and $R^3$ have the same meanings as defined above.)

Compound (Ia) can be obtained by cyclization of Compound (VII) with 1 to 10 equivalents of a carbonylation reagent such as N,N'-carbonyldiimidazole, phosgene, urea, alkyl chlorocarbonate, aryl chlorocarbonate or the like, if necessary in the presence of 1 to 10 equivalents of a base in an inert solvent. Examples of such bases are triethylamine, pyridine, and the like. Examples of inert solvents are water, alcohols (methanol, ethanol and the like), non-polar solvents (ethyl acetate, ether and the like), aprotic polar solvents (acetonitrile, N,N-dimethylformamide, N,N-dimethylacetamide, dimethyl sulfoxide, tetrahydrofuran, dioxane and the like) and halogenated hydrocarbons (dichloromethane, chloroform and the like). The reaction is carried out at a temperature between 0° C. and the boiling point of the solvent employed and is completed in 10 minutes to 48 hours.

In the case of Compound (VI) wherein $NR^2R^3$ has been protected with a suitable protective group, the desired compound can also be obtained by removal of the protective group after reduction reaction in Process 1-1 and carbonylation reaction in Process 1-2.

Process 1-3

Compound (Ib) wherein X is S (sulfur) can be prepared from Compound (VII) as the starting material according to the following reaction step:

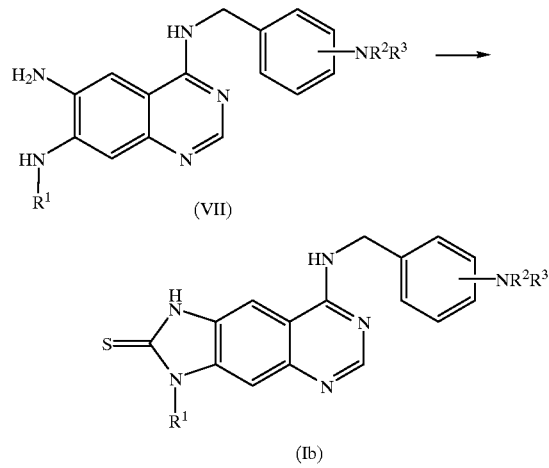

(In the formulae, $R^1$, $R^2$ and $R^3$ have the same meanings as defined above.)

Compound (Ib) can be obtained by cyclization of Compound (VII) with a thiocarbonylation reagent such as 1 to 10 equivalents of N,N'-thiocarbonyldiimidazole, thiophosgene, or 10 to 200 equivalents of carbon disulfide or the like, if necessary in the presence of 1 to 10 equivalents of a base in an inert solvent. Examples of such bases and inert solvents are the same as those described in Process 1-2 for preparation of Compound (Ia). The reaction is carried out at a temperature between 0° C. and the boiling point of the solvent employed and is completed in 10 minutes to 48 hours.

In the case of Compound (VI) wherein $NR^2R^3$ has been protected with a suitable protective group, the desired compound can also be obtained by removal of the protective group after reduction reaction in Process 1-1 and thiocarbonylation reaction in Process 1-3.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without purification.

Among Compounds (I), some may have configurational isomers, geometrical isomers, optical isomers or tautomers. The present invention includes all such possible isomers and mixtures thereof.

In the case where a salt of Compound (I) is desired and it is produced in the form of the desired salt, it can be subjected to purification as such. In the case where Compound (I) is produced in the free form and its salt is desired, Compound (I) is dissolved or suspended in a suitable solvent, followed by addition of an acid to form a salt which may be isolated and purified.

Compounds (I) and pharmaceutically acceptable salts thereof may be in the form of adducts with water or various solvents, which are also within the scope of the present invention.

Examples of Compound (I) obtained in the present invention are shown in Table 1.

TABLE 1-1

| Compd. No. | X | $R^1$ | Position of substitution (2, 3, 4) | $R^2$ | $R^3$ |
|---|---|---|---|---|---|
| 1 | O | $CH_2CH_3$ | 2 | H | $CH_3$ |
| 2 | O | $CH_2CH_3$ | 4 | H | $CH_3$ |
| 3 | O | $CH_2CH_3$ | 4 | H | $CH_2$-phenyl |
| 4 | O | $CH_2CH_3$ | 4 | H | $CH(CH_3)_2$ |
| 5 | O | $CH_2CH_3$ | 4 | H | $CH_2CH_2CH_3$ |
| 6 | O | $CH_2CH_3$ | 4 | H | $CH_2CH_3$ |
| 7 | O | $CH_2CH_3$ | 2 | H | $CH_2CH_2$-morpholino |
| 8 | O | $CH_2CH_3$ | 2 | H | $CH_2CH_2CH_2$-morpholino |
| 9 | O | $CH_2CH_3$ | 2 | H | $CH_2CH_2OH$ |
| 10 | O | $CH_2CH_3$ | 2 | H | $CH_2CH_2OCH_3$ |

TABLE 1-2

| Compd. No. | X | $R^1$ | Position of substitution (2, 3, 4) | $R^2$ | $R^3$ |
|---|---|---|---|---|---|
| 11 | O | $CH_2CH_3$ | 2 | \multicolumn{2}{l}{$-CH_2CH_2-O-CH_2CH_2-$} |
| 12 | O | $CH_2CH_3$ | 2 | \multicolumn{2}{l}{$-CH_2CH_2-CH(CH_2OH)-CH_2CH_2-$} |
| 13 | O | $CH_2CH_3$ | 2 | \multicolumn{2}{l}{$-CH_2CH_2-CH_2-CH_2CH_2-$} |
| 14 | O | $CH_2CH_3$ | 2 | \multicolumn{2}{l}{$-CH_2CH_2-N(CH_3)-CH_2CH_2-$} |
| 15 | O | $CH_2CH_3$ | 2 | \multicolumn{2}{l}{$-CH_2CH_2-S-CH_2CH_2-$} |
| 16 | O | $CH_2CH_3$ | 3 | \multicolumn{2}{l}{$-CH_2CH_2-O-CH_2CH_2-$} |
| 17 | O | $CH_2CH_3$ | 3 | \multicolumn{2}{l}{$-CH_2CH_2-CH_2-CH_2CH_2-$} |
| 18 | O | $CH_2CH_3$ | 3 | \multicolumn{2}{l}{$-CH_2CH_2-N(CH_3)-CH_2CH_2-$} |
| 19 | O | $CH_2CH_3$ | 4 | \multicolumn{2}{l}{$-CH_2CH_2-CH_2-CH_2CH_2-$} |
| 20 | O | $CH_2CH_3$ | 4 | \multicolumn{2}{l}{$-CH_2CH_2-N(CH_3)-CH_2CH_2-$} |

TABLE 1-3
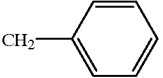
| Compd. No. | X | R¹ | Position of substitution (2, 3, 4) | R² | R³ |
|---|---|---|---|---|---|
| 21 | O | CH₂CH₃ | 4 | | —CH₂CH₂—S—CH₂CH₂— |
| 22 | S | CH₂CH₃ | 2 | H | CH₃ |
| 23 | S | CH₂CH₃ | 4 | H | CH₃ |
| 24 | S | CH₂CH₃ | 4 | H | CH₂—C₆H₅ |
| 25 | S | CH₂CH₃ | 4 | H | CH(CH₃)₂ |
| 26 | S | CH₂CH₃ | 4 | H | CH₂CH₂CH₃ |
| 27 | S | CH₂CH₃ | 4 | H | CH₂CH₃ |
| 28 | S | CH₂CH₃ | 2 | H | CH₂CH₂—morpholino |
| 29 | S | CH₂CH₃ | 2 | H | CH₂CH₂CH₂—morpholino |
| 30 | S | CH₂CH₃ | 2 | H | CH₂CH₂OH |

TABLE 1-4

| Compd. No. | X | R¹ | Position of substitution (2, 3, 4) | R² | R³ |
|---|---|---|---|---|---|
| 31 | S | CH₂CH₃ | 4 | H | CH₂CH₂OH |
| 32 | S | CH₂CH₃ | 2 | H | CH₂CH₂OCH₃ |
| 33 | S | CH₂CH₃ | 2 | —CH₂CH₂—O—CH₂CH₂— | |
| 34 | S | CH₂CH₃ | 2 | —CH₂CH₂—CH(CH₂OH)—CH₂CH₂— | |
| 35 | S | CH₂CH₃ | 2 | —CH₂CH₂—CH₂—CH₂CH₂— | |
| 36 | S | CH₂CH₃ | 2 | —CH₂CH₂—N(CH₃)—CH₂CH₂— | |
| 37 | S | CH₂CH₃ | 2 | —CH₂CH₂—S—CH₂CH₂— | |
| 38 | S | CH₂CH₃ | 3 | —CH₂CH₂—O—CH₂CH₂— | |
| 39 | S | CH₂CH₃ | 3 | —CH₂CH₂—CH₂—CH₂CH₂— | |
| 40 | S | CH₂CH₃ | 3 | —CH₂CH₂—N(CH₃)—CH₂CH₂— | |

TABLE 1-5

| Compd. No. | X | R¹ | Position of substitution (2, 3, 4) | R² | R³ |
|---|---|---|---|---|---|
| 41 | S | CH₂CH₃ | 4 | —CH₂CH₂—O—CH₂CH₂— | |
| 42 | S | CH₂CH₃ | 4 | —CH₂CH₂—CH₂—CH₂CH₂— | |
| 43 | S | CH₂CH₃ | 4 | —CH₂CH₂—N(CH₃)—CH₂CH₂— | |
| 44 | S | CH₂CH₃ | 4 | —CH₂CH₂—CH₂CH₂— | |
| 45 | S | CH₂CH₃ | 4 | —CH₂CH₂—S—CH₂CH₂— | |
| 46 | S | CH₂CH₃ | 2 | CH₃ | CH₂CH₂OH |
| 47 | S | CH₂CH₃ | 4 | —CH₂—CH(CH₂OH)—CH₂CH₂CH₂— | |

TABLE 1-5-continued

| Compd. No. | X | R¹ | Position of substitution (2, 3, 4) | R² | R³ |
|---|---|---|---|---|---|
| 48 | O | CH₂CH₃ | 4 | —CH₂CH₂—O—CH₂CH₂— | |
| 49 | O | CH₂CH₃ | 4 | H | CH₂CH₂OH |
| 50 | O | CH₂CH₃ | 2 | —CH=CH—N=CH— | |

TABLE 1-6

[Structure: imidazoquinazoline core with X=, R¹, HN-CH₂-phenyl(NR²R³) substituent with positions 2,3,4]

| Compd. No. | X | R¹ | Position of substitution (2, 3, 4) | R² | R³ |
|---|---|---|---|---|---|
| 51 | S | CH₂CH₃ | 2 | —CH=CH—N=CH— | |
| 52 | O | CH₂CH₃ | 2 | —CH₂CH₂—CH₂CH₂CH₂—CH₂CH₂— | |
| 53 | S | CH₂CH₃ | 2 | —CH₂CH₂—CH₂CH₂CH₂—CH₂CH₂— | |
| 54 | O | CH₂CH₃ | 2 | H | CH₂CH₂CH₃ |
| 55 | S | CH₂CH₃ | 2 | H | CH₂CH₂CH₃ |
| 56 | S | CH₂CH₃ | 2 | H | CH(CH₃)₂ |
| 57 | O | CH₂CH₃ | 2 | —CH₂—CH(CH₂OH)—CH₂CH₂CH₂— | |
| 58 | S | CH₂CH₃ | 3 | —CH₂CH₂CH(CH₂OH)CH₂CH₂— | |
| 59 | S | CH₂CH₃ | 2 | —CH₂CH₂CH(CH₂CH₂OH)CH₂CH₂— | |
| 60 | O | CH₂CH₃ | 2 | H | CH(CH₃)₂ |

TABLE 1-7

[Same structure as above]

| Compd. No. | X | R¹ | Position of substitution (2, 3, 4) | R² | R³ |
|---|---|---|---|---|---|
| 61 | O | CH₂CH₃ | 2 | H | CH₂CH₃ |
| 62 | S | CH₂CH₃ | 2 | H | CH₂CH₃ |
| 63 | S | CH₂CH₃ | 2 | —CH₂CH(CH₂OH)CH₂CH₂CH₂— | |
| 64 | S | CH₂CH₃ | 2 | H | cyclopentyl |
| 65 | S | CH₂CH₃ | 2 | H | CH₂CH₂CH₂CH₃ |
| 66 | O | CH₂CH₃ | 2 | —CH₂CH₂CH₂CH₂— | |
| 67 | O | CH₂CH₃ | 2 | H | CH₂CH₂CH₃ |
| 68 | S | CH₂CH₃ | 2 | H | cyclohexyl |
| 69 | O | CH₂CH₃ | 2 | H | cyclohexyl |
| 70 | S | CH₂CH₃ | 2 | —CH₂CH₂CH₂CH₂— | |

TABLE 1-8

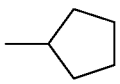

| Compd. No. | X | R¹ | Position of substitution (2, 3, 4) | R² | R³ |
|---|---|---|---|---|---|
| 71 | O | CH₂CH₃ | 2 | —CH₂CH₂—N(CH₂CH₃)—CH₂CH₂— | |
| 72 | O | CH₂CH₃ | 2 | H | CH₂CH(CH₃)₂ |
| 73 | S | CH₂CH₃ | 2 | —CH₂CH₂CH₂CH₂CH₂CH₂— | |
| 74 | O | CH₂CH₃ | 2 | H | cyclopentylmethyl |
| 75 | S | CH₂CH₃ | 2 | H | 1-adamantylmethyl |
| 76 | O | CH₂CH₃ | 2 | —CH₂—CH₂—CH(CH₂OH)—CH₂—CH₂— | |
| 77 | S | CH₂CH₃ | 2 | —CH₂CH₂—N(CH₂CH₃)—CH₂CH₂— | |
| 78 | S | CH₂CH₃ | 2 | H | CH₂CH(CH₃)₂ |
| 79 | S | CH₂CH₃ | 2 | H | CH₂CH₂CH₂CH₂OH |
| 80 | S | CH₂CH₂CH₃ | 2 | —CH₂—CH₂—CH(CH₂OH)—CH₂—CH₂— | |

TABLE 1-9

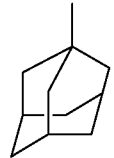

| Compd. No. | X | R¹ | Position of substitution (2, 3, 4) | R² | R³ |
|---|---|---|---|---|---|
| 81 | O | CH₂CH₃ | 2 | —CH₂CH₂—CH₂—CH₂—CH₂CH₂— | |
| 82 | S | CH₂CH₃ | 2 | —CH₂CH₂—N(CH₃)—CH₂—CH₂—CH₂— | |
| 83 | S | CH₂CH₃ | 2 | H | —CH₂CH₂OCH₂CH₂OH |
| 84 | O | CH₂CH₃ | 2 | —CH₂CH₂—N(CH₃)—CH₂—CH₂—CH₂— | |
| 85 | S | CH₃ | 2 | —CH₂—CH₂—CH(CH₂OH)—CH₂—CH₂— | |

TABLE 1-9-continued
| Compd. No. | X | R¹ | Position of substitution (2, 3, 4) | R² | R³ |
|---|---|---|---|---|---|
| 86 | S | CH₂CH₃ | 2 | H | 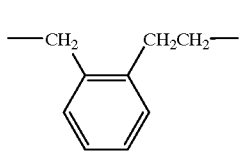 |
| 87 | S | CH₂CH₃ | 2 | —CH₂ | 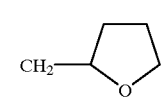 CH₂CH₂— |
| 88 | S | CH₂CH₃ | 2 | H | 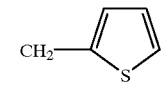 |
| 89 | S | CH₂CH₃ | 2 | H | 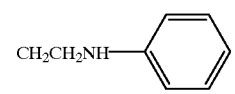 |
| 90 | S | CH₂CH₃ | 2 | H | CH₂CH₂NH— |
TABLE 1-10
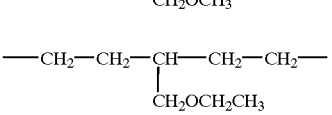
| Compd. No. | X | R¹ | Position of substitution (2, 3, 4) | R² | R³ |
|---|---|---|---|---|---|
| 91 | S | CH₂CH₃ | 2 | —CH₂—CH₂—CH—CH₂—CH₂—<br>　　　　　　　　　CH₂OCH₃ | |
| 92 | S | CH₂CH₃ | 2 | —CH₂—CH₂—CH—CH₂—CH₂—<br>　　　　　　　　　CH₂OCH₂CH₃ | |
| 93 | S | CH₂CH₃ | 2 | H | H |

TABLE 1-10-continued

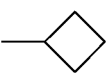

| Compd. No. | X | R¹ | Position of substitution (2, 3, 4) | R² | R³ |
|---|---|---|---|---|---|
| 94 | S | CH$_2$CH$_3$ | 2 | H | 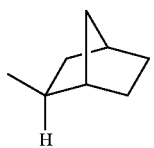 |
| 95 | S | CH$_2$CH$_3$ | 2 | H | |
| 96 | S | CH$_2$CH$_3$ | 2 | —CH$_2$—CH$_2$—N(CO$_2$CH$_2$CH$_3$)—CH$_2$—CH$_2$— | |

BEST MODE FOR CARRYING OUT THE INVENTION

Hereinafter, PDE inhibitory activity and pharmacological activity of the representative Compounds (I) are described in more detail by Test Examples. Test Example 1. The inhibitory activity on PDE derived from canine tracheal smooth muscle (1) Purification of an Enzyme According to the method of Torphy et al. [Mol. Pharmacol., 37, 206 (1990)], PDE V (cGMP-specific PDE) was purified from canine tracheal smooth muscle.

(2) Measurement of PDE Activity

The activity was measured based on the method of Kincaid et-al. [J. D. Corbin et al., Methods Enzymol., 159, 457(1988), Academic Press, New York]. The measurement was carried out using, as a substrate, 1.0 μM [³H]cGMP, and the reaction was carried out in a buffer having the following composition:

50 mM N,N-bis(2-hydroxyethyl)-2-aminoethanesulfonic acid (pH 7.2), 1 mM MgCl$_2$, 0.1 mg/ml soybean trypsin inhibitor.

The reaction was started by addition of the enzyme and stopped by addition of hydrochloric acid after reacting for 10 to 30 minutes at 30° C. Thereafter, sodium hydroxide was added for neutralization and 5'-GMP was converted into guanosine using 5'-nucleotidase. The reaction solution was subjected to DEAE-Sephadex A-25 column. [³H]Guano sine was eluted with distilled water and the radioactivity was measured with a liquid scintillation counter. The inhibitor was dissolved in 1.7% DMSO.

The results on the PDE inhibitory activity are shown in Table 2.

TABLE 2

| | PDE V inhibitory activity |
|---|---|
| Compound No. | Inhibition rate (%) Compound conc.:1 nM |
| 3 | 62 |
| 6 | 37 |
| 22 | 91 |
| 24 | 88 |
| 27 | 97 |
| 30 | 97 |
| 33 | 98 |
| 34 | 95 |
| 35 | 95 |

Test Example 2. The Hypotensive Effect in Rats

After a male Spraque-Dawley rat (two mice/group) anesthetized with urethane was fixed in the supine position, a cannula was inserted into trachea and the rat was artificially ventilated under the conditions of a tidal volume of 10 mg/kg and 60 breathes/min. The carotid artery and the duodenum were cannulated for measuring blood pressure and administering a drug, respectively. The drug was dissolved in distilled water and administered duodenally using the above cannula. Mean blood pressure (mBP) until -30 minutes after the drug-administration was measured and the maximum lowering rate (%) from the value before the drug-administration (100%) was determined. No change of mBP was observed during 30 minutes in case of administrating distilled water.

The results are shown in Table 3.

TABLE 3

Hypotensive activity

| Compound No. | Maximum lowering rate (%) rat, 10 mg/kg, i.d. N = 2 |
|---|---|
| 2 | 19.7 |
| 15 | 19.8 |
| 36 | 17.6 |
| 40 | 16.1 |

Test Example 3. Effect of Developed Cavernous Pressure and Duration of Tumescence in Rats A male Sprague-Dawley rat was anesthetized with urethane (1.3 g/kg) subcutaneously injected into the back of the neck. The perineal incision was performed and the right crus of the penis was exposed. For measurement of cavernous pressure, a needle (25G) attached to a polyethylene tube (PE50) filled with a heparin solution was inserted into the right crus. The polyethylene tube was connected to a pressure transducer (MPC-500, Millar Instruments) and cavernous pressure was amplified with an amplifier (AP-621G, Nihon Kohden) and then recorded on a pen recorder (LR4220, Yokokawa Denki). The abdomen was incised and cavernous nerves on the prostate was exposed. The nerve was placed on a bipolar tungsten electrode and stimulated by current pulses(frequency; 20 Hz, duration; 0.2 ms, strength; 3 to 5 V) for 50 seconds with an electric stimulator (SEN-3201, Nihon Koden) to induce increases in cavernous pressure. The test compounds were dissolved in distilled water (DW) or 0.01 N hydrochloric acid at a concentration of 1 mg/ml and injected into the cavernous body(0.02 ml/rat) with a needle (27G). Before(Pre) and six minutes after administration (6-min). of distilled water (DW) or the test compounds, the nerve was stimulated, and developed cavernous pressure (DCP) and the duration of tumescence (DT) were measured. DT was defined as the time from the start of stimulation to 50% of the peak cavernous pressure after the end of stimulation.

The results are shown in Table 4.

TABLE 4

Effects on developed cavernous pressure and duration of tumescence in rats

| Compound No. | DCP (mmHg) | | DT (sec) | | |
|---|---|---|---|---|---|
| | Pre | 6-min | Pre | 6-min | |
| 34 (20 μg/rat) | 23.9 ± 2.0 | 31.1 ± 4.7 | 3.3 ± 0.9 | 16.9 ± 2.4 | N = 5 |
| control (DW) | 25.9 ± 3.9 | 26.8 ± 4.4 | 2.8 ± 0.3 | 3.0 ± 0.7 | N = 5 |
| 26 (20 μg/rat) | 21.5 | 27.7 | 3.8 | 22.9 | N = 2 |
| 35 (20 μg/rat) | 22.6 | 21.2 | 1.6 | 8.1 | N = 2 |
| conrol (0.01 N HCl) | 20.2 | 19.2 | 3.2 | 3.3 | N = 2 |

Compound (I) or pharmaceutically acceptable salts thereof can be formulated into the normally employed forms, for example, tablets, capsules, injections, drops, syrups, sublingual tablets, various cream agents, suppositories or the like, and the resulting preparations can be administered orally or parenterally, for example, intramuscularly, intravenously, intra-arterialy, by instillation or application, or rectally by suppositories. Formulation into those oral or parenteral preparations normally uses the known methods. Preparations may contain various excipients, lubricants, binders, disintegrating agents, suspending agents, isotonizing agents, emulsifiers, and the like.

Examples of carriers used for preparations are water, distilled water for injection, physiological saline, glucose, sucrose, mannitol, lactose, starch, cellulose, methylcellulose, carboxymethyl cellulose, hydroxypropyl cellulose, alginate, talc, sodium citrate, calcium carbonate, calcium hydrogenphosphate, magnesium stearate, urea, silicone resin, sorbitan fatty acid ester, glyceric acid ester, and the like.

The dose and frequency of administration varies depending upon the mode of administration, the age, weight and conditions of patients, and the like. Normally, the oral dose of 0.05 to 5 g/60 kg/day is suitable. In the case of instillation, the dose is preferably in the range of 0.01 to 5 mg/kg/min. and preferably does not exceed the limit of the oral dose per day.

Certain embodiments of the present invention are illustrated in the following Examples and Reference Examples.

The measurement of proton nuclear magnetic resonance spectrum (NMR) used in Examples and Reference Examples was carried out at 270 MHz. Peak positions are expressed as units of 1/million (ppm) downfield from tetramethylsilane. Peak shapes are expressed as follows: s: singlet, d: doublet, t: triplet, m: multiplet, br: broad.

REFERENCE EXAMPLE 1

2-Methylaminobenzonitrile

2-Fluorobenzonitrile (10.0 g, 82.8 mmol) was dissolved in acetonitrile (100 ml), and 40% aqueous methylamine solution (200 ml) was added thereto, followed by stirring at 60° C. overnight. 40% aqueous methylamine solution (100 ml) was further added thereto, followed by stirring at 60° C. for 9 hours. The reaction mixture was concentrated under reduced pressure, then water was added to the resulting residue, the mixture was extracted with chloroform. After the organic layer was dried (over anhydrous magnesium sulfate), the drying agent was filtered off, and the organic layer was concentrated under reduced pressure. The resulting oily substances were purified by silica gel column chromatography (the substances were eluted with an increasing concentration of chloroform from chloroform/hexane=1/2 to chloroform/hexane=1/1) to give the title compound (5.38 g, 49%).

$^1$H-NMR (CDCl$_3$) δ (ppm): 2.87(3H, d, J=5.0 Hz), 4.70 (1H, q, J=5.0 Hz), 6.61–6.69(2H, m), 7.35–7.43(2H, m).

REFERENCE EXAMPLE 2

4-Methylaminobenzonitrile

According to a similar manner to that in Reference Example 1, the title compound was synthesized from 4-fluorobenzonitrile and 40% aqueous methylamine solution.

$^1$H-NMR (CDCl$_3$) δ (ppm): 2.87(3H, d, J=5.0 Hz), 4.39 (1H, br), 6.55(2H, d, J=8.8 Hz), 7.42(2H, d, J=8.8 Hz).

REFERENCE EXAMPLE 3

4-Benzylaminobenzonitrile

4-Fluorobenzonitrile (6.0 g, 49.5 mmol) was dissolved in acetonitrile (60 ml), and benzylamine (10.6 g, 98.9 mmol) was added thereto, followed by stirring at 100° C. for 3 days. To complete the reaction, benzylamine (21.2 g, 198 mmol) was further added thereto, followed by stirring at 100° C. for 1 day. The solvent was removed under reduced pressure, water was added to the resulting residue, and the mixture was extracted with chloroform. After the organic layer was dried (over anhydrous magnesium sulfate), the drying agent was filtered off, and the filtrate was concentrated under reduced pressure. The resulting oily substances were purified by silica gel column chromatography (the substances were eluted with an increasing concentration of chloroform from chloroform/hexane=1/2 to chloroform/hexane=1/1) to give the title compound (7.42 g, 72%) as oily substances.

$^1$H-NMR (CDCl$_3$) δ (ppm): 4.32(2H, d, J=4.7 Hz), 4.80 (1H, br), 6.55(2H, d, J=8.4 Hz), 7.25–7.37(7H, m).

REFERENCE EXAMPLE 4

4-Isopropylaminobenzonitrile

According to a similar manner to that in Reference Example 3, the title compound was synthesized from 4-fluorobenzonitrile and isopropylamine.

$^1$H-NMR (CDCl$_3$) δ (ppm): 1.23(6H, d, J=6.6 Hz), 3.61–3.69(1H, m), 4.22(1H, br), 6.53(2H, d, J=8.9 Hz), 7.38(2H, d, J=8.9 Hz).

REFERENCE EXAMPLE 5

4-Propylaminobenzonitrile

According to a similar manner to that in Reference Example 3, the title compound was synthesized from 4-fluorobenzonitrile and n-propylamine.

$^1$H-NMR (CDCl$_3$) δ (ppm): 0.99(3H, t, J=7.4 Hz), 1.57–1.71(2H, m), 3.06–3.34(2H, m), 4.50(1H, br), 6.55 (2H, d, J=8.7 Hz), 7.38(2H, d, J=8.7 Hz).

REFERENCE EXAMPLE 6

4-Ethylaminobenzonitrile

According to a similar manner to that in Reference Example 1, the title compound was synthesized from 4-fluorobenzonitrile and 70% aqueous ethylamine solution.

$^1$H-NMR (CDCl$_3$) δ (ppm): 1.27(3H, t, J=7.3 Hz), 3.13–3.23(2H, m), 4.22(1H, br), 6.54(2H, d, J=8.6 Hz), 7.40(2H, d, J=8.6 Hz).

REFERENCE EXAMPLE 7

2-(2-Morpholinoethylamino)benzonitrile

According to a similar manner to that in Reference Example 3, the title compound was synthesized from 2-fluorobenzonitrile and 4-(2-aminoethyl)morpholine.

$^1$H-NMR (CDCl$_3$) δ (ppm): 2.48–2.56(4H, m), 2.68(2H, t, J=6.2 Hz), 3.20–3.27(2H, m), 3.73–3.80(4H, m), 5.36(1H, br), 6.62–6.70(2H, m), 7.35–7.41(2H, m).

REFERENCE EXAMPLE 8

2-(3-Morpholinopropylamino)benzonitrile

According to a similar manner to that in Reference Example 3, the title compound was synthesized from 2-fluorobenzonitrile and 4-(3-aminopropyl)morpholine.

$^1$H-NMR (CDCl$_3$) δ (ppm): 1.79–1.92(2H, m), 2.46–2.55 (6H, m), 3.22–3.35(2H, m), 3.75–3.86(4H, m), 5.67(1H, br), 6.61–6.70(2H, m), 7.34–7.39(2H, m).

REFERENCE EXAMPLE 9

2-(2-Hydroxyethylamino)benzonitrile

According to a similar manner to that in Reference Example 3, the title compound was synthesized from 2-fluorobenzonitrile and ethanolamine.

$^1$H-NMR (CDCl$_3$) δ (ppm): 3.30–3.36(2H, m), 3.43(1H, br), 3.80–3.85(2H, m), 5.02(1H, t, J=5.0 Hz), 6.60–6.67(2H, m), 7.31–7.36(2H, m)

REFERENCE EXAMPLE 10

4-(2-Hydroxyethylamino)benzonitrile

According to a similar manner to that in Reference Example 3, the title compound was synthesized from 4-fluorobenzonitrile and ethanolamine.

$^1$H-NMR(CDCl$_3$-CD$_3$OD) δ (ppm): 3.26–3.32(2H, m), 3.78–3.82(2H, m), 6.58(2H, d, J=8.9 Hz), 7.39(2H, d, J=8.9 Hz).

REFERENCE EXAMPLE 11

2-(2-Methoxyethylamino)benzonitrile

According to a similar manner to that in Reference Example 3, the title compound was synthesized from 2-fluorobenzonitrile and 2-methoxyethylamine.

$^1$H-NMR (CDCl$_3$) δ (ppm): 3.38(2H, t, J=5.4 Hz), 3.41 (3H, s), 3.62(2H, t, J=5.4 Hz), 4.86(1H, br), 6.65–6.70(2H, m), 7.35–7.40(2H, m).

REFERENCE EXAMPLE 12

2-Morpholinobenzonitrile

2-Fluorobenzonitrile (1.21 g, 1.00 mmol) was dissolved in acetonitrile (50 ml), and morpholine (33 ml, 377 mmol) was added thereto followed by stirring at 110° C. for 2 nights. After the reaction was completed, the reaction mixture was concentrated to give oily substances which were then purified by silica gel chromatography (eluent: chloroform) to give the title compound (1.80 g, 95%) as oily substances.

$^1$H-NMR (CDCl$_3$) δ (ppm): 3.15–3.23(4H, m), 3.83–3.97 (4H, m), 7.01–7.10(2H, m), 7.48–7.60(2H, m).

REFERENCE EXAMPLE 13

2-(4-Ethoxycarbonylpiperidino)benzonitrile

According to a similar manner to that in Reference Example 12, the title compound was synthesized from 2-fluorobenzonitrile and ethyl isonipecotate.

$^1$H-NMR (CDCl$_3$) δ (ppm): 1.28(3H, t, J=7.1 Hz), 1.92–2.10(4H, m), 2.41–2.51(1H, m), 2.84–2.94(2H, m), 3.51–3.58(2H, m), 4.17(2H, q, J=7.1 Hz), 6.96–7.02(2H, m), 7.44–7.56(2H, m).

REFERENCE EXAMPLE 14

2-Piperidinobenzonitrile

According to a similar manner to that in Reference Example 12, the title compound was synthesized from 2-fluorobenzonitrile and piperidine.

$^1$H-NMR (CDCl$_3$) δ (ppm): 1.54–1.62(2H, m), 1.70–1.79 (4H, m), 3.11–3.16(4H, m), 6.90–6.99(2H, m), 7.40–7.51 (2H, m).

REFERENCE EXAMPLE 15

2-(4-Methyl-1-piperazinyl)benzonitrile

According to a similar manner to that in Reference Example 12, the title compound was synthesized from 2-fluorobenzonitrile and 1-methylpiperazine.

$^1$H-NMR (CDCl$_3$) δ (ppm): 2.36(3H, s), 2.60–2.65(4H, m), 3.21–3.26(4H, m), 6.97–7.03(2H, m), 7.45–7.56(2H, m).

REFERENCE EXAMPLE 16

2-Thiomorpholinobenzonitrile

According to a similar manner to that in Reference Example 12, the title compound was synthesized from 2-fluorobenzonitrile and thiomorpholine.

$^1$H-NMR (CDCl$_3$) δ (ppm): 2.84–2.88(4H, m), 3.42–3.47 (4H, m), 7.00–7.06(2H, m), 7.55(1H, dd, J=6.9 Hz, 6.9 Hz), 7.58(1H, d, J=6.9 Hz).

REFERENCE EXAMPLE 17

3-Morpholinobenzonitrile

3-Fluorobenzonitrile (4.35 g, 36.0 mmol) was dissolved in acetonitrile (40 ml), and morpholine (110 ml, 1.25 mol) was added thereto followed by stirring at 110° C. for 3 days and nights. The reaction mixture was concentrated to give oily substances which were then purified by silica gel chromatography (eluent: chloroform) to give the title compound (1.80 g, 27%) as oily substances.

$^1$H-NMR (CDCl$_3$) δ (ppm): 3.15–3.19(4H, m), 3.83–3.88 (4H, m), 7.09–7.18(3H, m), 7.34(1H, dd, J=7.6 Hz, 7.6 Hz).

REFERENCE EXAMPLE 18

3-Morpholinobenzonitrile

3-Cyanophenol (1.77 g, 14.9mmol) and triethylamine (6.30 ml, 45.2 mmol) were dissolved in methylene chloride (75 ml) and stirred at −10° C. in an argon gas atmosphere. A solution of trifluoroacetic anhydride (3.79 ml, 22.5 mmol) dissolved in methylene chloride (15 ml) was added dropwise thereto, and after the addition was completed, the mixture was stirred for 1.5 hours. After the reaction was completed, the solvent was removed under reduced pressure, and an aqueous solution of sodium hydrogen carbonate was added to the resulting concentrated residue and the mixture was extracted with methylene chloride. The organic layer was washed with a saturated aqueous sodium chloride solution and dried over sodium sulfate. The drying agent was filtered off and the filtrate was concentrated. The resulting concentrated residue was purified by silica gel column chromatography (chloroform/methanol=100) to give oily substances. The resulting oily substances were dissolved in acetonitrile (40 ml). Morpholine (33.0 ml, 378 mmol) was added thereto and the mixture was stirred for 3 days under heating at reflux. The solvent and unreacted reagents were distilled off under reduced pressure, water was added to the concentrated residue, and the mixture was extracted with chloroform. The organic layer was dried (over sodium sulfate), the drying agent was filtered off, and the filtrate was concentrated. The resulting concentrated filtrate was purified by silica gel column chromatography (eluent: chloroform/hexane=1/2) to give the title compound (0.74 g, 26%) as oily substances.

$^1$H-NMR (CDCl$_3$) δ (ppm): 3.15–3.19(4H, m), 3.83–3.88 (4H, m), 7.09–7.18(3H, m), 7.34(1H, dd, J=7.6 Hz, 7.6 Hz).

REFERENCE EXAMPLE 19

3-Piperidinobenzonitrile

According to a similar manner to that in Reference Example 17, the title compound was synthesized from 3-fluorobenzonitrile and piperidine.

$^1$H-NMR (CDCl$_3$) δ (ppm): 1.55–1.73(6H, m), 3.17–3.23 (4H, m), 7.03(1H, d, J=7.6 Hz), 7.08–7.12(2H, m), 7.24–7.29(1H, m).

REFERENCE EXAMPLE 20

3-(4-Methyl-1-piperazinyl)benzonitrile

According to a similar manner to that in Reference Example 17, the title compound was synthesized from 3-fluorobenzonitrile and 1-methylpiperazine.

$^1$H-NMR (CDCl$_3$) δ (ppm): 2.35(3H, s), 2.55–2.60(4H, m), 3.21–3.25(4H, m), 7.06–7.13(3H, m), 7.28–7.31(1H, m).

REFERENCE EXAMPLE 21

4-Morpholinobenzonitrile

According to a similar manner to that in Reference Example 12, the title compound was synthesized from 4-fluorobenzonitrile and morpholine.

$^1$H-NMR (CDCl$_3$) δ (ppm): 3.26–3.30(4H, m), 3.83–3.87 (4H, m), 6.86(2H, d, J=8.9 Hz), 7.51(2H, d, J=8.9 Hz).

REFERENCE EXAMPLE 22

4-Piperidinobenzonitrile

According to a similar manner to that in Reference Example 12, the title compound was synthesized from 4-fluorobenzonitrile and piperidine.

$^1$H-NMR (CDCl$_3$) δ (ppm): 1.60–1.75(6H, m), 3.30–3.38 (4H, m), 6.83(2H, d, J=8.9 Hz), 7.45(2H, d, J=8.9 Hz).

REFERENCE EXAMPLE 23

4-(4-Methyl-1-piperazinyl)benzonitrile

According to a similar manner to that in Reference Example 12, the title compound was synthesized from 4-fluorobenzonitrile and 1-methylpiperazine.

$^1$H-NMR (CDCl$_3$) δ (ppm): 2.35(3H, s), 2.52–2.59(4H, m), 3.31–3.39(4H, m), 6.86(2H, d, J=8.9 Hz), 7.49(2H, d, J=8.9 Hz).

REFERENCE EXAMPLE 24

4-(1-Pyrrolidinyl)benzonitrile

According to a similar manner to that in Reference Example 12, the title compound was synthesized from 4-fluorobenzonitrile and pyrrolidine.

$^1$H-NMR (CDCl$_3$) δ (ppm): 2.01–2.09(4H, m), 3.29–3.34 (4H, m), 6.49(2H, d, J=8.9 Hz), 7.43(2H, d, J=8.9 Hz).

REFERENCE EXAMPLE 25

4-Thiomorpholinobenzonitrile

According to a similar manner to that in Reference Example 12, the title compound was synthesized from 4-fluorobenzonitrile and thiomorpholine.

$^1$H-NMR (CDCl$_3$) δ (ppm): 2.62–2.75(4H, m), 3.74–3.80 (4H. m), 6.81(2H. d, J=8.9 Hz), 7.49(2H, d, J=8.9 Hz).

REFERENCE EXAMPLE 26

7-Ethylamino-6-nitro-4 (3H)-quinazolinone (a compound described in WO95/06649)

7-Chloro-6-nitro-4(3H)-quinazolinone (20.0 g, 88.7 mmol) was suspended in n-butanol (150 ml), 70% aqueous ethylamine solution (120 ml) was added thereto, and the mixture was stirred for 15 minutes to give a clear solution which was then heated for 9 hours in a sealed tube in an oil bath (oil bath temperature set at 100° C. ). After the reaction was completed, the reaction mixture was left and cooled to precipitate yellow solids (first crystal) which were then filtered off. The first crystal was washed with methanol and ether and dried to give the desired title compound (8.27 g, 40%). The filtrate obtained at the time of acquisition of the first crystal was concentrated to precipitate crystal which was then filtered off and subjected to the same procedures as above to give second crystal as the desired title compound (5.84 g, 24%).

REFERENCE EXAMPLE 27

4-Chloro-7-ethylamino-6-nitroquinazoline

7-Ethylamino-6-nitro-4(3H)-quinazolinone (30.0 g, 128 mmol) was suspended in phosphorus oxychloride (270 ml, 2.90 mol) and the mixture was heated at 110° C. for 2 hours under an argon gas atmosphere (to form a clear solution). After it was confirmed that the starting material disappeared, unreacted phosphorus oxychloride was removed under reduced pressure. After the residue was subjected to azeotrope with toluene, the resulting oily substances were dissolved in the necessary minimum amount of tetrahydrofuran. The tetrahydrofuran solution obtained was poured onto ice-cold water by adding a sufficient amount of sodium hydrogen carbonate, followed by extraction with ethyl acetate. The organic layer was dried (over anhydrous magnesium sulfate), and the drying agent was filtered off. The filtrate was concentrated under reduced pressure to give the title compound (33.4 g).

$^1$H-NMR (CDCl$_3$) δ (ppm): 1.45(3H, t, J=7.3 Hz), 3.42–3.47(2H, m), 7.18(1H, s), 7.79(1H, br), 8.84(1H, s), 9.11(1H, s).

REFERENCE EXAMPLE 28

7-Ethylamino-4-(2-methyaminobenzylamino)-6-nitroquinazoline

Lithium aluminum hydride (3.28 g, 86.4 mmol) was suspended in tetrahydrofuran (100 ml), followed by stirring under ice-cooling in an argon gas atmosphere. A solution of 2-methylaminobenzonitrile (3.80 g, 28.8 mmol) obtained in Reference Example 1, dissolved in tetrahydrofuran (30 ml), was added dropwise and portionwise thereto. After the addition was completed, the solution was stirred for 3 hours under heating at reflux. After the reaction was completded, the reaction solution was cooled and sodium sulfate decahydrate was portionwise added thereto until foaming ceased. Thereafter, the insolubles were filtered off and the filtrate was concentrated under reduced pressure to give oily 2-methylaminobenzylamine.

The resulting substance and triethylamine (20.0 ml, 143 mmol) were dissolved in tetrahydrofuran (100 ml), and 4-chloro-7-ethylamino-6-nitroquinazoline (the compound obtained in Reference Example 27, 6.47 g, 25.6 mmol) was added thereto, followed by stirring at room temperature overnight. After the reaction was completed, the solvent was removed under reduced pressure, water was added to the resulting residue, and the precipitated solids were filtered off. Further, they were washed with ether-methanol to give the title compound (6.88 g, 76%).

$^1$H-NMR (DMSO-d$_6$) δ (ppm): 1.30(3H, t, J=7.2 Hz), 2.76(3H, d, J=4.5 Hz), 3.36–3.43(2H, m), 4.60(2H, d, J=5.4 Hz), 5.73(1H, q, J=4.5 Hz), 6.50–6.59(2H, m), 6.85(1H, s), 7.08–7.16(2H, m), 7.74(1H, t, J=5.4 Hz), 8.36(1H, s), 9.05 (1H, t, J=5.7 Hz), 9.26(1H, s).

REFERENCE EXAMPLE 29

7-Ethylamino-4-(4-methylaminobenzylamino)-6-nitroquinazoline

According to a similar manner to that in Reference Example 28, the title compound was obtained from 4-chloro-7-ethylamino-6-nitroquinazoline and a compound obtained after the compound in Reference Example 2 was reduced by lithium aluminum hydride.

$^1$H-NMR (DMSO-d$_6$) δ (ppm): 1.31(3H, t, J=7.1 lHz), 2.84(3H, d, J=5.3 Hz), 3.35(2H, q, J=7.1 lHz), 4.62(2H, d, J=5.3 Hz), 5.45–5.60(1H, br), 6.64(2H, d, J=8.6 Hz), 6.83 (1H, s), 7.19(2H, d, J=8.6 Hz), 7.71(1H, t, J=5.3 Hz), 8.32(1H, s), 9.06(1H, t, J=5.3 Hz), 9.28(1H, s).

REFERENCE EXAMPLE 30

4-(4-Benzylaminobenzylamino)-7-ethylamino-6-nitroquinazoline

According to a similar manner to that in Reference Example 28, the title compound was obtained from 4-chloro-7-ethylamino-6-nitroquinazoline and a compound obtained after the compound in Reference Example 3 was reduced by lithium aluminum hydride.

$^1$H-NMR (DMSO-d$_6$) δ (ppm): 1.27(3H, t, J=7.2 Hz), 3.33–3.41(2H, m), 4.24(2H, d, J=4.5 Hz), 4.56(2H, d, J=5.4 Hz), 6.20(1H, br), 6.53(2H, d, J=8.4 Hz), 6.83(1H, s), 7.06(2H, d, J=8.4 Hz), 7.16–7.35(5H, m), 7.71(1H, t, J=5.2 Hz), 8.32(1H, s), 9.03(1H, t, J=5.4 Hz), 9.25(1H, s).

REFERENCE EXAMPLE 31

7-Ethylamino-4-(4-isopropylaminobenzylamino)-6-nitroquinazoline

According to a similar manner to that in Reference Example 28, the title compound was obtained from 4-chloro-7-ethylamino-6-nitroquinazoline and a compound obtained after the compound in Reference Example 4 was reduced by lithium aluminum hydride.

$^1$H-NMR (CDCl$_3$) δ (ppm): 1.22(6H, d, J=6.3 Hz), 1.40 (3H, t, J=7.3 Hz), 3.32–3.42(2H, m), 3.58–3.66(1H, m), 4.68(2H, d, J=5.0 Hz), 6.03(1H, br), 6.58(2H, d, J=8.6 Hz), 6.98(1H, s), 7.20(2H, d, J=8.6 Hz), 7.68(1H, t, J=4.6 Hz), 8.54(1H, s), 8.66(1H, s), 9.40(1H, br).

REFERENCE EXAMPLE 32

7-Ethylamino-6-nitro-4-(4-propylaminobenzylamino)quinazoline

According to a similar manner to that in Reference Example 28, the title compound was obtained from 4-chloro-7-ethylamino-6-nitroquinazoline and a compound obtained after the compound in Reference Example 5 was reduced by lithium aluminum hydride.

$^1$H-NMR (DMSO-d$_6$) δ (ppm): 0.91(3H, t, J=7.4 Hz), 1.27(3H, t, J=7.2 Hz), 1.50–1.60(2H, m), 2.90–2.96(2H, m), 3.32–3.40(2H, m), 4.57(2H, d, J=5.9 Hz), 5.48(1H, br), 6.51(2H, d, J=8.4 Hz), 6.85(1H, s), 7.09(2H, d, J=8.4 Hz), 7.72(1H, t, J=5.9 Hz), 8.33(1H, s), 9.07(1H, br), 9.27(1H, s).

REFERENCE EXAMPLE 33

7-Ethylamino-4-(4-ethylaminobenzylamino)-6-nitroquinazoline

According to a similar manner to that in Reference Example 28, the title compound was obtained from 4-chloro-7-ethylamino-6-nitroquinazoline and a compound obtained after the compound in Reference Example 6 was reduced by lithium aluminum hydride.

$^1$H-NMR (DMSO-d$_6$) δ (ppm): 1.14(3H, t, J=7.3 Hz), 1.28(3H, t, J=7.1 Hz), 3.00(2H, q, J=7.3 Hz), 3.38(2H, q, J=7.1 Hz), 4.58(2H, d, J=5.6 Hz), 5.40(1H, br), 6.50(2H, d, J=8.6 Hz), 6.83(1H, s), 7.09(2H, d, J=8.6 Hz), 7.74(1H, t, J=5.6 Hz), 8.33(1H, s), 9.09(1H, t, J=5.6 Hz), 9.28(1H, s).

REFERENCE EXAMPLE 34

7-Ethylamino-4-[2-(2-morpholinoethylamino)benzylamino]-6-nitroquinazoline

According to a similar manner to that in Reference Example 28, the title compound was obtained from 4-chloro-7-ethylamino-6-nitroquinazoline and a compound obtained after the compound in Reference Example 7 was reduced by lithium aluminum hydride.

$^1$H-NMR (CDCl$_3$) δ (ppm): 1.40(3H, t, J=7.2 Hz), 2.37–2.55(4H, m), 2.58(2H, t, J=6.2 Hz), 3.20–3.25(2H, m), 3.31–3.41(2H, m), 3.44–3.53(4H, m), 4.80(2H, d, J=5.5 Hz), 5.12(1H, br), 6.32(1H, t, J=5.2 Hz), 6.65–6.74(2H, m), 6.98(1H, s), 7.21–7.29(2H, m), 7.68(1H, t, J=4.7 Hz), 8.55 (1H, s), 8.70(1H, s).

REFERENCE EXAMPLE 35

7-Ethylamino-4-[2-(3-morpholinopropylamino) benzylamino]-6-nitroquinazoline

According to a similar manner to that in Reference Example 28, the title compound was obtained from 4-chloro-7-ethylamino-6-nitroquinazoline and a compound obtained after the compound in Reference Example 8 was reduced by lithium aluminum hydride.

$^1$H-NMR (CDCl$_3$) δ (ppm): 1.40(3H, t, J=7.2 Hz), 1.72–1.83(2H, m), 2.32–2.42(6H, m), 3.17(2H, t, J=6.7 Hz), 3.34–3.42(2H, m), 3.64–3.71(4H, m), 4.82(2H, d, J=5.9 Hz), 5.30(1H, br), 6.32(1H, br), 6.67(1H, dd, J=7.4 Hz, 7.9 Hz), 6.71(1H, d, J=7.4 Hz), 6.98(1H, s), 7.20–7.23(2H, m), 7.70(1H, t, J=4.5 Hz), 8.54(1H, s), 8.68(1H, s).

REFERENCE EXAMPLE 36

7-Ethylamino-4-[2-(2-hydroxyethylamino) benzylamino]-6-nitroquinazoline

According to a similar manner to that in Reference Example 28, the title compound was obtained from 4-chloro-7-ethylamino-6-nitroquinazoline and a compound obtained after the compound in Reference Example 9 was reduced by lithium aluminum hydride.

$^1$H-NMR (DMSO-d$_6$) δ (ppm): 1.26(3H, t, J=7.1 Hz), 3.09–3.16(2H, m), 3.58(2H, q, J=7.1 Hz), 3.54–3.62(2H, m), 4.61(2H, d, J=5.3 Hz), 4.72(1H, t, J=5.3 Hz), 5.74(1H, t, J=5.3 Hz), 6.55–6.60(2H, m), 6.86(1H, s), 7.07–7.15(2H, m), 7.77(1H, t, J=5.3 Hz), 8.38(1H, s), 9.09(1H, t, J=5.6 Hz), 9.25(1H, s).

REFERENCE EXAMPLE 37

7-Ethylamino-4-[4-(2-hydroxyethylamino) benzylamino]-6-nitroquinazoline

According to a similar manner to that in Reference Example 28, the title compound was obtained from 4-chloro-7-ethylamino-6-nitroquinazoline and a compound obtained after the compound in Reference Example 10 was reduced by lithium aluminum hydride.

$^1$H-NMR (DMSO-d$_6$) δ (ppm): 1.26(3H, t, J=6.9 Hz), 3.03–3.09(2H, m), 3.38(2H, q, J=6.9 Hz), 3.50–3.56(2H, m), 4.58(2H, d, J=5.0 Hz), 4.65(1H, t, J=5.6 Hz), 5.42(1H, t, J=5.0 Hz), 6.54(2H, d, J=6.6 Hz), 6.85(1H, s), 7.10(2H, d, J=6.6 Hz), 7.71(1H, br), 8.34(1H, s), 9.08(1H, br), 9.27(1H, s).

REFERENCE EXAMPLE 38

7-Ethylamino-4-[2-(2-methoxyethylamino) benzylamino]-6-nitroquinazoline

According to a similar manner to that in Reference Example 28, the title compound was obtained from 4-chloro-7-ethylamino-6-nitroquinazoline and a compound obtained after the compound in Reference Example 11 was reduced by lithium aluminum hydride.

$^1$H-NMR (DMSO-d$_6$) δ (ppm): 1.29(3H, t, J=6.9 Hz), 3.18–3.23(5H, m), 3.39(2H, q, J=6.9 Hz), 3.49(2H, t, J=5.4 Hz), 4.64(2H, d, J=5.9 Hz), 5.73(1H, br), 6.58(1H, d, J=7.9 Hz), 6.60(1H, d, J=6.9 Hz), 6.86(1H, s), 7.07–7.18(2H, m), 7.76(1H, t, J=5.3 Hz), 8.37(1H, s), 9.07(1H, br), 9.25(1H, s).

REFERENCE EXAMPLE 39

7-Ethylamino-4-(2-morpholinobenzylamino)-6-nitroquinazoline

Lithium aluminum hydride (6.36 g, 168mmol) was suspended in dried tetrahydrofuran (200 ml), followed by stirring under ice-cooling in an argon gas atmosphere. A solution of 2-morpholinobenzonitrile (9.56 g, 50.8 mmol) obtained in Reference Example 12, dissolved in tetrahydrofuran (150 ml), was dropwise added thereto over 30 minutes. After the addition was completed, the solution was stirred for 2 hours under heating at reflux. After the reaction was completed, the reaction solution was cooled and sodium sulfate decahyrate was portionwise added thereto until foaming ceased. Thereafter, the insolubles were filtered off and the filtrate was concentrated to give oily 2-morpholinobenzylamine.

The resulting substance and triethylamine (35.4 ml, 253 mmol) were dissolved in tetrahydrofuran (200 ml), and 4-chloro-7-ethylamino-6-nitroquinazoline (7.34 g, 30.6 mmol) was added thereto, followed by stirring at room temperature overnight. After the reaction was completed, the solvent was removed under reduced pressure and the resulting residue was purified by silica gel column chromatography (eluent: chloroform/methanol=100) to give the title compound (7.17 g, 60%).

$^1$H-NMR (CDCl$_3$) δ (ppm): 1.41(3H, t, J=7.3 Hz), 3.04–3.08(4H, m), 3.38(2H, q, J=7.3 Hz), 3.90–3.94(4H, m), 4.97(2H, d, J=4.6 Hz), 7.03(1H, s), 7.12–7.18(1H, m), 7.25(1H, d, J=7.9 Hz), 7.31–7.40(2H, m), 7.74(1H, br), 7.87(1H, s), 8.54(1H, s), 8.72(1H, s).

REFERENCE EXAMPLE 40

7-Ethylamino-4-[2-(4-hydroxymethylpiperidino) benzylamino]-6-nitroquinazoline

According to a similar manner to that in Reference Example 39, the title compound was obtained from 4-chloro-7-ethylamino-6-nitroquinazoline and a compound obtained after the compound in Reference Example 13 was reduced by lithium aluminum hydride.

$^1$H-NMR (DMSO-d$_6$) δ (ppm): 1.30(3H, t, J=7.3 Hz), 1.32–1.50(2H, m), 1.74–1.79(3H, m), 2.62–2.70(2H, m), 3.07–3.12(2H, m), 3.30–3.50(4H, m), 4.45(1H, t, J=5.3 Hz), 4.84(2H, d, J=5.3 Hz), 6.87(1H, s), 6.99(1H, dd, J=6.6 Hz, 6.9 Hz), 7.13(1H, d, J=7.3 Hz), 7.19–7.24(2H, m), 7.74(1H, t, J=5.3 Hz), 8.31(1H, s), 9.06(1H, t, J=5.6 Hz), 9.31(1H, s).

REFERENCE EXAMPLE 41

7-Ethylamino-6-nitro-4-(2-piperidinobenzylamino) quinazoline

According to a similar manner to that in Reference Example 39, the title compound was obtained from 4-chloro-7-ethylamino-6-nitroquinazoline and a compound obtained after the compound in Reference Example 14 was reduced by lithium aluminum hydride.

$^1$H-NMR (CDCl$_3$) δ (ppm): 1.41(3H, t, J=7.3 Hz), 1.61–1.79(2H, m), 1.81–1.88(4H, m), 2.95–3.04(4H, m), 3.38(2H, q, J=7.3 Hz), 4.95(2H, d, J=5.0 Hz), 6.98(1H, s), 7.10(1H, dd, J=7.3 Hz, 8.9 Hz), 7.22–7.36(3H, m), 7.71(1H, t, J=5.0 Hz), 8.37(1H, br), 8.53(1H, s), 8.72(1H, s).

REFERENCE EXAMPLE 42

7-Ethylamino-4-[2-(4-methyl-1-piperazinyl) benzylamino]-6-nitroquinazoline

According to a similar manner to that in Reference Example 39, the title compound was obtained from 4-chloro-7-ethylamino-6-nitroquinazoline and a compound obtained after the compound in Reference Example 15 was reduced by lithium aluminum hydride.

$^1$H-NMR (CDCl$_3$) δ (ppm): 1.41(3H, t, J=7.3 Hz), 2.42 (3H, s), 2.70–2.80(4H, m), 3.05–3.15(4H, m), 3.40(2H, q, J=7.3 Hz), 3.70(1H, br), 4.95(2H, s), 6.94(1H, s), 7.12(1H, dd, J=7.3 Hz, 7.3 Hz), 7.23–7.36(3H, m), 7.73(1H, br), 8.44(1H, br), 8.89(1H, s).

REFERENCE EXAMPLE 43

7-Ethylamino-6-nitro-4-(2thiomorpholinobenzylamino)quinazoline

According to a similar manner to that in Reference Example 39, the title compound was obtained from 4-chloro- 7-ethylamino-6-nitroquinazoline and a compound obtained after the compound in Reference Example 16 was reduced by lithium aluminum hydride.

$^1$H-NMR (DMSO-$d_6$) δ (ppm): 1.31(3H, t, J=7.1 Hz), 2.70–2.80(4H, m), 3.10–3.18(4H, m), 3.35–3.44(2H, m), 4.83(2H, d, J=5.3 Hz), 6.86(1H, s), 7.04(1H, dd, J=7.3 Hz, 7.6 Hz), 7.15(1H, d, J=7.9 Hz), 7.21–7.27(2H, m), 7.73(1H, t, J=5.3 Hz), 8.32(1H, s), 9.03(1H, t, J=5.4 Hz), 9.32(1H, s).

REFERENCE EXAMPLE 44

7-Ethylamino-4-(3-morpholinobenzylamino)-6-nitroquinazoline

According to a similar manner to that in Reference Example 39, the title compound was obtained from 4-chloro-7-ethylamino-6-nitroquinazoline and a compound obtained after the compound in Reference Example 17 or 18 was reduced by lithium aluminum hydride.

$^1$H-NMR (DMSO-$d_6$) δ (ppm): 1.30(3H, t, J=7.1 Hz), 3.06–3.15(4H, m), 3.32–3.39(2H, m), 3.71–3.78(4H, m), 4.70(2H, d, J=5.3 Hz), 6.79–6.85(3H, m), 6.96(1H, s), 7.17(1H, dd, J=7.9 Hz, 7.9 Hz), 7.71(1H, t, J=5.3 Hz), 8.32(1H, s), 9.13(1H, t, J=5.6 Hz), 9.28(1H, s).

REFERENCE EXAMPLE 45

7-Ethylamino-6-nitro-4-(3-piperidinobenzylamino) quinazoline

According to a similar manner to that in Reference Example 39, the title compound was obtained from 4-chloro-7-ethylamino-6-nitroquinazoline and a compound obtained after the compound in Reference Example 19 was reduced by lithium aluminum hydride.

$^1$H-NMR (CDCl$_3$) δ (ppm): 1.40(3H, t, J=7.3 Hz), 1.53–1.73(6H, m), 3.13–3.18(4H, m), 3.32–3.40(2H, m), 4.77(2H, d, J=5.0 Hz), 6.29(1H, br), 6.80–6.90(2H, m), 6.96(1H, s), 6.98(1H, s), 7.17–7.27(1H, m), 7.67(1H, t, J=4.6 Hz), 8.54(1H, s), 8.71(1H, s).

REFERENCE EXAMPLE 46

7-Ethylamino-4-[3-(4-methyl-1-piperazinyl) benzylamino]-6-nitroquinazoline

According to a similar manner to that in Reference Example 39, the title compound was obtained from 4-chloro-7-ethylamino-6-nitroquinazoline and a compound obtained after the compound in Reference Example 20 was reduced by lithium aluminum hydride.

$^1$H-NMR (CDCl$_3$) δ (ppm): 1.36(3H, t, J=7.3 Hz), 2.31 (3H, s), 2.49–2.58(4H, m), 3.14–3.24(4H, m), 3.29(2H, q, J=7.3 Hz), 4.77(2H, d, J=4.3 Hz), 6.73–6.93(4H, m), 7.16–7.22(2H, m), 7.61(1H, t, J=4.3 Hz), 8.50(1H, s), 8.82 (1H, s).

REFERENCE EXAMPLE 47

7-Ethylamino-4-(4-morpholinobenzylamino)-6-nitroquinazoline

According to a similar manner to that in Reference Example 39, the title compound was obtained from 4-chloro-7-ethylamino-6-nitroquinazoline and a compound obtained after the compound in Reference Example 21 was reduced by lithium aluminum hydride.

$^1$H-NMR (DMSO-$d_6$) δ (ppm): 1.26(3H, t, J=7.1 Hz), 3.30–3.07(4H, m), 3.34(2H, q, J=7.1 Hz), 3.70–3.73(4H, m), 4.64(2H, d, J=5.3 Hz), 6.85(1H, s), 6.90(2H, d, J=8.6 Hz), 7.23(2H, d, J=8.6 Hz), 7.74(1H, br), 8.33(1H, s), 9.15(1H, br), 9.27(1H, s).

REFERENCE EXAMPLE 48

7-Ethylamino-6-nitro-4-(4-piperidinobenzylamino) quinazoline

According to a similar manner to that in Reference Example 39, the title compound was obtained from 4-chloro-7-ethylamino-6-nitroquinazoline and a compound obtained after the compound in Reference Example 22 was reduced by lithium aluminum hydride.

$^1$H-NMR (CDCl$_3$) δ (ppm): 1.41(3H, t, J=7.4 Hz), 1.50–1.80(6H, m), 3.02–3.19(4H, m), 3.33–3.43(2H, m), 4.73(2H, s), 6.20(1H, br), 6.80–7.00(2H, m), 7.21–7.30(3H, m), 7.69(1H, br), 8.54(1H, s), 8.69(1H, s).

REFERENCE EXAMPLE 49

7-Ethylamino-4-[4-(4-methyl-1-piperazinyl) benzylamino]- 6-nitroquinazoline

According to a similar manner to that in Reference Example 39, the title compound was obtained from 4-chloro-7-ethylamino-6-nitroquinazoline and a compound obtained after the compound in Reference Example 23 was reduced by lithium aluminum hydride.

$^1$H-NMR (CDCl$_3$) δ (ppm): 1.39(3H, t, J=7.3 Hz), 2.37 (3H, s), 2.55–2.62(4H, m), 3.18–3.33(4H, m), 3.38(2H, q, J=7.3 Hz), 4.74(2H, d, J=5.0 Hz), 6.15(1H, br), 6.93(2H, d, J=8.6 Hz), 6.99(1H, s), 7.31(2H, d, J=8.6 Hz), 7.69(1H, br), 8.55(1H, s), 8.69(1H, s).

REFERENCE EXAMPLE 50

7-Ethylamino-6-nitro-4-[4-(1-pyrrolidinyl) benzylamino)quinazoline

According to a similar manner to that in Reference Example 39, the title compound was obtained from 4-chloro-7-ethylamino-6-nitroquinazoline and a compound obtained after the compound in Reference Example 24 was reduced by lithium aluminum hydride.

$^1$H-NMR (DMSO-$d_6$) δ (ppm): 1.30(3H, t, J=7.1 Hz), 1.91–2.00(4H, m), 3.17–3.22(4H, m), 3.32–3.41(3H, m), 4.62(2H, d, J=5.6 Hz), 6.48(2H, d, J=8.6 Hz), 6.84(1H, s), 7.19(2H, d, J=8.6 Hz), 7.73(1H, t, J=5.6 Hz), 8.27(1H, s), 8.32(1H, s).

REFERENCE EXAMPLE 51

7-Ethylamino-6-nitro-4-(4-thiomorpholinobenzylamino)quinazoline

According to a similar manner to that in Reference Example 39, the title compound was obtained from 4-chloro-7-ethylamino-6-nitroquinazoline and a compound obtained after the compound in Reference Example 25 was reduced by lithium aluminum hydride.

$^1$H-NMR (CDCl$_3$) δ (ppm): 1.41(3H, t, J=7.2 Hz), 2.72–2.77(4H, m), 3.36–3.43(2H, m), 3.55–3.61(4H, m), 4.74(2H, d, J=4.9 Hz), 5.96(1H, br), 6.90(2H, d, J=8.9 Hz), 7.00(1H, s), 7.30(2H, d, J=8.9 Hz), 7.69(1H, br), 8.56(1H, s), 8.65(1H, s).

REFERENCE EXAMPLE 52

2-[N-(2-hydroxyethyl)methylamino]benzonitrile

According to a similar manner to that in Reference Example 3, the title compound was synthesized from 2-fluorobenzonitrile and N-methylethanolamine.

$^1$H-NMR (CDCl$_3$) δ (ppm): 2.60(1H, br), 3.02(3H, s), 3.49(2H, t, J=5.8 Hz), 3.87(2H, t, J=5.8 Hz), 6.89(1H, dd, J=7.3 Hz, 7.6 Hz), 7.01(1H, d, J=8.6 Hz), 7.39–7.52(2H, m).

REFERENCE EXAMPLE 53

7-Ethylamino-4-{2-[N-(2-hydroxyethyl)methylamino]benzylamino}-6-nitroquinazoline According to a similar manner to that in Reference Example 39, the title compound was obtained from 4-chloro-7-ethylamino-6-nitroquinazoline and a compound obtained after the compound in Reference Example 52 was reduced by lithium aluminum hydride.

$^1$H-NMR (CDCl$_3$) δ (ppm): 1.37(3H, t, J=7.1 Hz), 1.95 (1H, br), 2.75(3H, s), 3.19(2H, t, J=5.0 Hz), 3.27–3.38(2H, m), 3.85(2H, t, J=5.0 Hz), 4.95(2H, d, J=5.3 Hz), 6.88(1H, s), 7.14(1H, dd, J=7.3 Hz, 7.3 Hz), 7.23–7.32(2H, m), 7.46(1H, d, J=7.3 Hz), 7.63(1H, br), 8.20(1H, br), 8.45(1H, s), 8.96(1H, s).

REFERENCE EXAMPLE 54

4-(3-Hydroxymethylpiperidino)benzonitrile

According to a similar manner to that in Reference Example 3, the title compound was synthesized from 4-fluorobenzonitrile and 3-hydroxymethylpiperidine.

$^1$H-NMR (CDCl$_3$) δ (ppm): 1.20–1.32(1H, m), 1.56–1.73 (1H, m), 1.74–1.95(4H, m), 2.72–2.80(1H, m), 2.87–2.98 (1H, m), 3.47–3.76(3H, m), 3.86–3.92(1H, m), 6.87(2H, d, J=8.9 Hz), 7.44(2H, d, J=8.9 Hz).

REFERENCE EXAMPLE 55

7-Ethylamino-4-[4-(3-hydroxymethylpiperidino)benzylamino]-6-nitroquinazoline

According to a similar manner to that in Reference Example 39, the title compound was obtained from 4-chloro-7-ethylamino-6-nitroquinazoline and a compound obtained after the compound in Reference Example 54 was reduced by lithium aluminum hydride.

$^1$H-NMR (DMSO-d$_6$) δ (ppm): 1.00–1.15(1H, m), 1.30 (3H, t, J=7.2 Hz), 1.36–1.72(4H, m), 2.34–2.39(1H, m), 2.57–2.66(1H, m), 3.18–3.40(4H, m), 3.50–3.56(1H, m), 3.62–3.66(1H, m), 4.45–4.49(1H, m), 4.64(2H, d, J=5.4 Hz), 6.85(1H, s), 6.86(2H, d, J=8.9 Hz), 7.21(2H, d, J=8.9 Hz), 7.71(1H, br), 8.32(1H, s), 9.09(1H, t, J=5.4 Hz), 9.27(1H, s).

REFERENCE EXAMPLE 56

2-(1-Imidazolyl)benzonitrile

2-Fluorobenzonitrile (0.70 g, 5.78 mmol) was dissolved in acetonitrile (1 ml), and a sodium salt of imidazole (1.34 g, 14.8 mmol) was added thereto, followed by stirring at 100° C. for 1.5 hours. The reaction mixture was concentrated under reduced pressure and the resulting residue was purified by silica gel column chromatography (the sample was eluted with an increasing concentration of chloroform from chloroform/hexane=1/2 to 100% chloroform) to give the title compound (0.96 g, 98%).

$^1$H-NMR (CDCl$_3$) δ (ppm): 7.26(1H, s), 7.37(1H, s), 7.41–7.57(2H, m), 7.72–7.87(3H, m).

REFERENCE EXAMPLE 57

7-Ethylamino-4-[2-(1-imidazolyl)benzylamino]-6-nitroquinazoline

According to a similar manner to that in Reference Example 39, the title compound was obtained from 4-chloro-7-ethylamino-6-nitroquinazoline and a compound obtained after the compound in Reference Example 56 was reduced by lithium aluminum hydride.

$^1$H-NMR (DMSO-d$_6$) δ (ppm): 1.28(3H, t, J=7.1 Hz), 3.35–3.40(2H, m), 4.56(2H, d, J=5.3 Hz), 6.86(1H, s), 7.09(1H, s), 7.34–7.55(5H, m), 7.76(1H, t, J=5.3 Hz), 7.92 (1H, s), 8.27(1H, s), 9.13(1H, t, J=5.2 Hz), 9.28(1H, s).

REFERENCE EXAMPLE 58

2-(1-Perhydroazocinyl)benzonitrile

According to a similar manner to that in Reference Example 12, the title compound was obtained from 2-fluorobenzonitrile and heptamethyleneimine.

$^1$H-NMR (CDCl$_3$) δ (ppm): 1.55–1.65(6H, m), 1.76–1.82 (4H, m), 3.66–3.71(4H, m), 6.64(1H, dd, J=6.9 Hz, 7.9 Hz), 6.80(1H, d, J=8.6 Hz), 7.25–7.34(1H, m), 7.43(1H, d, J=7.9 Hz).

REFERENCE EXAMPLE 59

4-[2-(1-Perhydroazocinyl)benzylamino]-7-ethylamino-6-nitroquinazoline

According to a similar manner to that in Reference Example 39, the title compound was obtained from 4-chloro-7-ethylamino-6-nitroquinazoline and a compound obtained after the compound in Reference Example 58 was reduced by lithium aluminum hydride.

$^1$H-NMR (CDCl$_3$) δ (ppm): 1.36(3H, t, J=7.1 Hz), 1.68–1.72(10H, m), 3.14–3.15(4H, m), 3.27–3.32(2H, m), 4.96(2H, d, J=5.3 Hz), 6.92(1H, s), 7.00–7.06(1H, m), 7.24–7.33(3H, m), 7.48(1H, br), 7.64(1H, br), 8.48(1H, s), 8.77(1H, s).

REFERENCE EXAMPLE 60

2-Propylaminobenzonitrile

According to a similar manner to that in Reference Example 3, the title compound was synthesized from 2-fluorobenzonitrile and n-propylamine.

$^1$H-NMR (CDCl$_3$) δ (ppm): 1.00(3H, t, J=7.3 Hz), 1.58–1.72(2H, m), 3.10–3.15(2H, m), 4.55(1H, br), 6.58–6.65(2H, m), 7.32–7.38(2H, m).

REFERENCE EXAMPLE 61

7-Ethylamino-6-nitro-4-(2-propylaminobenzylamino)quinazoline

According to a similar manner to that in Reference Example 28, the title compound was obtained from 4-chloro-7-ethylamino-6-nitroquinazoline and a compound obtained after the compound in Reference Example 60 was reduced by lithium aluminum hydride.

$^1$H-NMR (DMSO-d$_6$) δ (ppm): 0.88(3H, t, J=7.3 Hz), 1.28(3H, t, J=7.1 Hz), 1.51–1.59(2H, m), 2.98–3.02(2H, m), 3.33–3.41(2H, m), 4.64(2H, d, J=5.6 Hz), 5.61(1H, br), 6.51–6.58(2H, m), 6.86(1H, s), 7.06–7.15(2H, m), 7.78(1H, t, J=5.3 Hz), 8.35(1H, s), 9.10(1H, t, J=5.6 Hz), 9.25(1H, s).

REFERENCE EXAMPLE 62

2-Isopropylaminobenzonitrile

According to a similar manner to that in Reference Example 3, the title compound was synthesized from 2-fluorobenzonitrile and isopropylamine.

¹H-NMR (CDCl₃) δ (ppm): 1.23(6H, d, J=6.3 Hz), 3.61–3.75(1H, m), 4.40(1H, br), 6.57–6.66(2H, m), 7.30–7.37(2H, m).

REFERENCE EXAMPLE 63

7-Ethylamino-4-(2-isopropylaminobenzylamino)-6-nitroquinazoline

According to a similar manner to that in Reference Example 28, the title compound was obtained from 4-chloro-7-ethylamino-6-nitroquinazoline and a compound obtained after the compound in Reference Example 62 was reduced by lithium aluminum hydride.

¹H-NMR (DMSO-d₆) δ (ppm): 1.08(6H, d, J=6.3 Hz), 1.28(3H, t, J=7.3 Hz), 3.34–3.40(2H, m), 3.43–3.59(1H, m), 4.64(2H, d, J=5.6 Hz), 5.51(1H, br), 6.51–6.58(2H, m), 6.86(1H, s), 7.06–7.17(2H, m), 7.77(1H, t, J=5.3 Hz), 8.37 (1H, s), 9.07(1H, t, J=5.6 Hz), 9.24(1H, s).

REFERENCE EXAMPLE 64

2-(3-Hydroxymethylpiperidino)benzonitrile

According to a similar manner to that in Reference Example 12, the title compound was synthesized from 2-fluorobenzonitrile and 3-(hydroxymethyl)piperidine.

¹H-NMR (CDCl₃) δ (ppm): 1.23–1.33(1H, m), 1.72–1.85 (3H, m), 1.97–2.17(2H, m), 2.80–2.94(2H, m), 3.35–3.52 (2H, m), 3.59–3.74(2H, m), 6.90–7.05(2H, m), 7.43–7.56 (2H, m).

REFERENCE EXAMPLE 65

7-Ethylamino-4-[2-(3-hydroxymethylpiperidino)benzylamino]-6-nitroquinazoline

According to a similar manner to that in Reference Example 39, the title compound was obtained from 4-chloro-7-ethylamino-6-nitroquinazoline and a compound obtained after the compound in Reference Example 64 was reduced by lithium aluminum hydride.

¹H-NMR (DMSO-d₆) δ (ppm): 1.07–1.12(1H, m), 1.30 (3H, t, J=7.1 Hz), 1.64–1.90(4H, m), 2.42–2.51(1H, m), 2.60–2.68(1H, m), 2.99–3.04(1H, m), 3.06–3.20(1H, m), 3.31–3.45(4H, m), 4.48(1H, t, J=5.3 Hz), 4.85(2H, d, J=5.3 Hz), 6.87(1H, s), 6.99(1H, dd, J=7.3 Hz, 7.3 Hz), 7.11(1H, d, J=6.9 Hz), 7.17–7.24(2H, m), 7.75(1H, t, J=5.3 Hz), 8.32(1H, s), 9.11(1H, t, J=5.6 Hz), 9.32(1H, s).

REFERENCE EXAMPLE 66

3-(4-Ethoxycarbonylpiperidino)benzonitrile

According to a similar manner to that in Reference Example 17, the title compound was synthesized from 3-fluorobenzonitrile and ethyl isonipecotate.

¹H-NMR (CDCl₃) δ (ppm): 1.28(3H, t, J=7.3 Hz), 1.77–1.92(2H, m), 1.95–2.07(2H, m), 2.42–2.54(1H, m), 2.81–2.91(2H, m), 3.62–3.70(2H, m), 4.15(2H, q, J=7.3 Hz), 7.05–7.14(3H, m), 7.27–7.34(1H, m).

REFERENCE EXAMPLE 67

7-Ethylamino-4-[3-(4-hydroxymethylpiperidino)benzylamino]-6-nitroquinazoline

According to a similar manner to that in Reference Example 39, the title compound was obtained from 4-chloro-7-ethylamino-6-nitroquinazoline and a compound obtained after the compound in Reference Example 66 was reduced by lithium aluminum hydride.

¹H-NMR (DMSO-d₆) δ (ppm): 1.20–1.50(5H, m), 1.71–1.77(2H, m), 2.58–2.66(2H, m), 3.26–3.43(5H, m), 3.64–3.69(2H, m), 4.45(1H, t, J=5.3 Hz), 4.69(2H, d, J=5.6 Hz), 6.72–6.86(3H, m), 6.95(1H, s), 7.13(1H, dd, J=7.9 Hz, 7.9 Hz), 7.75(1H, t, J=5.6 Hz), 8.32(1H, s), 9.17(1H, t, J=5.8 Hz), 9.30(1H, s).

REFERENCE EXAMPLE 68

2-[4-(2-Hydroxyethyl)piperidino]benzonitrile

According to a similar manner to that in Reference Example 12, the title compound was obtained from 2-fluorobenzonitrile and 4-(2-hydroxyethyl)piperidine.

¹H-NMR (CDCl₃) δ (ppm): 1.49–1.62(6H, m), 1.82–1.87 (2H, m), 2.75–2.83(2H, m), 3.56–3.61(2H, m), 3.72–3.77 (2H, m), 6.93–7.01(2H, m), 7.42–7.56(2H, m).

REFERENCE EXAMPLE 69

7-Ethylamino-4-{2-[4-(2-hydroxyethyl)piperidino]benzylamino}-6-nitroquinazoline

The title compound was obtained from 4-chloro-7-ethylamino-6-nitroquinazoline and a compound obtained after the compound in Reference Example 68 was reduced by lithium aluminum hydride.

¹H-NMR (DMSO-d₆) δ (ppm): 1.26–1.60(7H, m), 1.74–1.79(2H, m), 2.62–2.70(2H, m), 3.05–3.13(2H, m), 3.32–3.52(5H, m), 4.33(1H, t, J=5.2 Hz), 4.84(2H, d, J=5.4 Hz), 6.87(1H, s), 6.93–7.02(1H, m), 7.12(1H, d, J=7.4 Hz), 7.19–7.28(2H, m), 7.74(1H, t, J=5.2 Hz), 8.32(1H, s), 9.07 (1H, t, J=5.4 Hz), 9.31(1H, s).

REFERENCE EXAMPLE 70

2-(4-Ethoxycarbonyl-1-piperazinyl)benzaldehyde

2-Fluorobenzaldehyde (3.0 g, 24.2 mmol), 1-(ethoxycarbonyl)piperazine (4.2 ml, 28.7 ml), and calcium carbonate (2.46 g, 24.6 mmol) were reacted at 120° C. for 7.5 hours in dimethylsulfoxide (12 ml). After the reaction was completed, the insolubles were filtered off and the resulting filtrate was extracted by adding water and ethyl acetate thereto. The organic layer was dried over anhydrous magnesium sulfate and concentrated to give oily substances. The resulting oily substances were purified by silica gel column chromatography (eluent: from hexane/ethyl acetate= 4/1 to hexane/ethyl acetate=1/1) to give the title compound (4.29 g, 68%).

¹H-NMR (CDCl₃) δ (ppm): 1.29(3H, t, J=7.3 Hz), 3.03–3.07(4H, m), 3.67–3.71(4H, m), 4.14(2H, q, J=7.3 Hz), 7.10–7.19(2H, m), 7.52(1H, dd, J=7.6 Hz, 7.9 Hz), 7.83(1H, d, J=7.6 Hz), 10.35(1H, s).

REFERENCE EXAMPLE 71

4-[2-(4-Ethoxycarbonyl-1-piperazinyl)benzylamino]-7-ethylamino-6-nitroquinazoline The compound (2.5 g, 9.54 mmol) obtained in Reference Example 70 was dissolved in ethanol (25 ml), and hydroxylamine hydrochloride (0.862 g, 12.4 mmol) and sodium carbonate (1.32 g, 12.5 mmol) were added thereto, followed by stirring at room temperature overnight. After the reaction was completed, the insolubles were filtered off and filtrate was concentrated whereby oily substances were obtained. 10% palladium on carbon catalyst (2.30 g) was added to the resulting oily substances in methanol (100 ml) and the mixture was stirred at room temperature overnight in a hydrogen atmosphere. After the reaction was completed, the catalyst was filtered off with a filter aid. The compound (2.1 g) obtained by concentrating the resulting filtrate, 4-chloro-7-ethylamino-6-nitroquinazoline (2.00 g, 7.92 mmol) and triethylamine (5.50 ml, 40.3 mmol) were stirred overnight in tetrahydrofuran (50 ml). After the reaction was completed, the reaction solution was concentrated and the resulting oily substances were purified by silica gel column chromatography (eluent: chloroform/methanol=30/1) to give the title compound (1.53 g, 40%).

$^1$H-NMR (DMSO-d$_6$) δ (ppm): 1.21(3H, t, J=7.1 Hz), 1.29(3H, t, J=7.1 Hz), 2.85–2.89 (4H, m), 3.38(2H, q, J=7.1 Hz), 3.43–3.57(4H, m), 4.07(2H, q, J=7.1 Hz), 4.87(2H, d, J=5.3 Hz), 6.87(1H, s), 7.05(1H, dd, J=6.9 Hz, 7.9 Hz), 7.16 (1H, d, J=7.9 Hz), 7.22–7.28(2H, m), 7.77(1H, t, J=5.3 Hz), 8.33(1H, s), 9.14(1H, t, J=5.3 Hz), 9.32(1H, s).

REFERENCE EXAMPLE 72

2-Ethylaminobenzonitrile

According to a similar manner to that in Reference Example 12, the title compound was obtained from 2-fluorobenzonitrile and 70% aqueous ethylamine solution.

$^1$H-NMR (CDCl$_3$) δ (ppm): 1.25(3H, t, J=7.3 Hz), 3.13–3.21(2H, m), 4.55(1H, br), 6.58–6.64(2H, m), 7.28–7.37(2H, m).

REFERENCE EXAMPLE 73

7-Ethylamino-4-(2-ethylaminobenzylamino)-6-nitroquinazoline

The title compound was obtained from 4-chloro-7-ethylamino-6-nitroquinazoline and a compound obtained after the compound in Reference Example 72 was reduced by lithium aluminum hydride.

$^1$H-NMR (DMSO-d$_6$) δ (ppm): 1.17(3H, t, J=7.1 Hz), 1.28(3H, t, J=7.3 Hz), 3.04–3.17(2H, m), 3.33–3.43(2H, m), 4.64(2H, d, J=5.9 Hz), 5.62(1H, br), 6.52–6.59(2H, m), 6.87(1H, s), 7.07–7.15(2H, m), 7.78(1H, t, J=5.3 Hz), 8.36 (1H, s), 9.11(1H, t, J=5.9 Hz), 9.25(1H, s).

REFERENCE EXAMPLE 74

2-Cyclopentylaminobenzonitrile

According to a similar manner to that in Reference Example 12, the title compound was synthesized from 2-fluorobenzonitrile and cyclopentylamine.

$^1$H-NMR (CDCl$_3$) δ (ppm): 1.45–1.81(6H, m), 1.98–2.15 (2H, m), 3.78–3.87(1H, m), 4.52(1H, br), 6.59–6.69(2H, m), 7.27–7.38(2H, m).

REFERENCE EXAMPLE 75

4-(2-Cyclopentylaminobenzylamino)-7-ethylamino-6-nitroquinazoline

The title compound was obtained from 4-chloro-7-ethylamino-6-nitroquinazoline and a compound obtained after the compound in Reference Example 74 was reduced by lithium aluminum hydride.

$^1$H-NMR (DMSO-d$_6$) δ (ppm): 1.28(3H, t, J=7.1 Hz), 1.39–1.65(6H, m), 1.85–1.90(2H, m), 3.33–3.43(2H, m), 3.72–3.80(1H, m), 4.65(2H, d, J=5.9 Hz), 5.60(1H, d, J=5.9 Hz), 6.52–6.58(2H, m), 6.86(1H, s), 7.07–7.17(2H, m), 7.76(1H, t. J=5.3 Hz), 8.35(1H, s), 9.06(1H, t, J=5.9 Hz), 9.24(1H, s).

REFERENCE EXAMPLE 76

2-Butylaminobenzonitrile

According to a similar manner to that in Reference Example 12, the title compound was synthesized from 2-fluorobenzonitrile and butylamine.

$^1$H-NMR (CDCl$_3$) δ (ppm): 0.95(3H, t, J=7.3 Hz), 1.35–1.48(2H, m), 1.56–1.67(2H, m), 3.13–3.18(2H, m), 4.52(1H, br), 6.59–6.64(2H, m), 7.31–7.38(2H, m).

REFERENCE EXAMPLE 77

4-(2-Butylaminobenzylamino)-7-ethylamino-6-nitroquinazoline

The title compound was obtained from 4-chloro-7-ethylamino-6-nitroquinazoline and a compound obtained after the compound in Reference Example 76 was reduced by lithium aluminum hydride.

$^1$H-NMR (DMSO-d$_6$) δ (ppm): 0.85(3H, t, J=7.3 Hz), 1.25–1.37(5H, m), 1.46–1.57(2H, m), 2.95–3.05(2H, m), 3.38(2H, q, J=6.9 Hz), 4.64(2H, d, J=5.9 Hz), 5.53(1H, br), 6.51–6.59(2H, m), 6.87(1H, s), 7.06–7.15(2H, m), 7.77(1H, t, J=5.3 Hz), 8.35(1H, s), 9.08(1H, t, J=5.9 Hz), 9.25(1H, s).

REFERENCE EXAMPLE 78

2-(1-Pyrrolidinyl)benzonitrile

According to a similar manner to that in Reference Example 12, the title compound was synthesized from 2-fluorobenzonitrile and pyrrolidine.

$^1$H-NMR (CDCl$_3$) δ (ppm): 1.95–2.02(4H, m), 3.35–3.61 (4H, m), 6.56–6.66(2H, m), 7.28–7.34(1H, m), 7.40–7.44 (1H, m).

REFERENCE EXAMPLE 79

7-Ethylamino-6-nitro-4-[2-(1-pyrrolidinyl)benzylamino]quinazoline

The title compound was obtained from 4-chloro-7-ethylamino-6-nitroquinazoline and a compound obtained after the compound in Reference Example 78 was reduced by lithium aluminum hydride.

$^1$H-NMR (DMSO-d$_6$) δ (ppm): 1.29(3H, t, J=7.1 Hz), 1.87–1.92(4H, m), 3.13–3.18(4H, m), 3.34–3.44(2H, m), 4.76(2H, d, J=5.3 Hz), 6.82–6.87(2H, m), 6.98(1H, d, J=7.6 Hz), 7.12–7.18(2H, m), 7.75(1H, t, J=5.4 Hz), 8.32(1H, s), 9.11(1H, t, J=5.3 Hz), 9.33(1H, s).

REFERENCE EXAMPLE 80

2-Cyclohexylaminobenzonitrile

According to a similar manner to that in Reference Example 12, the title compound was synthesized from 2-fluorobenzonitrile and cyclohexylamine.

$^1$H-NMR (CDCl$_3$) δ (ppm): 1.16–1.45(5H, m), 1.62–1.67 (1H, m), 1.75–1.82(2H, m), 1.99–2.04(2H, m), 3.30–3.37 (1H, m), 4.45(1H, m), 6.57–6.67(2H, m), 7.30–7.39(2H, m).

REFERENCE EXAMPLE 81

4-(2-Cyclohexylaminobenzylamino)-7-ethylamino-6-nitroquinazoline

The title compound was obtained from 4-chloro-7-ethylamino-6-nitroquinazoline and a compound obtained after the compound in Reference Example 80 was reduced by lithium aluminum hydride.

$^1$H-NMR (DMSO-d$_6$) δ (ppm): 1.05–1.18(3H, m), 1.20–1.37(5H, m), 1.55–1.69(3H, m), 1.85–1.89(2H, m), 3.15–3.24(1H, m), 3.33–3.43(2H, m), 4.64(2H,d, J=5.6 Hz), 5.50(1H, d, J=7.3 Hz), 6.50–6.58(2H, m), 6.87(1H, s), 7.05–7.18(2H, m), 7.77(1H, t, J=5.1 Hz), 8.37(1H, s), 9.06 (1H, t, J=5.6 Hz), 9.24(1H, s).

REFERENCE EXAMPLE 82

2-(4-Ethyl-1-piperazinyl)benzonitrile

According to a similar manner to that in Reference Example 12, the title compound was synthesized from 2-fluorobenzonitrile and 4-ethylpiperazine.

¹H-NMR (CDCl₃) δ (ppm): 1.13(3H, t, J=7.3 Hz), 2.50 (2H, q, J=7.3 Hz), 2.66–2.70(4H, m), 3.24–3.28(4H, m), 6.96–7.03(2H, m), 7.45–7.60(2H, m).

REFERENCE EXAMPLE 83

7-Ethylamino-4-[2-(4-ethyl-1-piperazinyl)benzylamino]-6-nitroquinazoline

The title compound was obtained from 4-chloro-7-ethylamino-6-nitroquinazoline and a compound obtained after the compound in Reference Example 82 was reduced by lithium aluminum hydride.

¹H-NMR (DMSO-d₆) δ (ppm): 1.03(3H, t, J=7.3 Hz.), 1.28(3H, t, J=7.1 Hz), 2.39(2H, q, J=7.3 Hz), 2.50–2.60(4H, m), 2.85–2.93(4H, m), 3.36–3.44(2H, m), 4.84(2H, d, J=5.3 Hz), 6.87(1H, s), 7.02(1H, dd, J=6.6 Hz, 6.9 Hz), 7.15(1H, d, J=6.9 Hz), 7.16–7.24(2H, m), 7.75(1H, t, J=5.3 Hz), 8.32(1H, s), 9.08(1H, br), 9.31(1H, s).

REFERENCE EXAMPLE 84

2-(2-Methylpropylamino)benzonitrile

According to a similar manner to that in Reference Example 12, the title compound was synthesized from 2-fluorobenzonitrile and isobutylamine.

¹H-NMR (CDCl₃) δ (ppm): 0.99(6H, d, J=7.6 Hz), 1.80–1.97(1H, m), 2.97–3.00(2H, m), 4.61(1H, br), 6.58–6.64(2H, m), 7.31–7.37(2H, m).

REFERENCE EXAMPLE 85

7-Ethylamino-4-[2-(2-methylpropylamino)benzylamino]-6-nitroquinazoline

The title compound was obtained from 4-chloro-7-ethylamino-6-nitroquinazoline and a compound obtained after the compound in Reference Example 84 was reduced by lithium aluminum hydride.

¹H-NMR (DMSO-d₆) δ (ppm): 0.86(6H, d, J=6.6 Hz), 1.28(3H, t, J=7.1 Hz), 1.75–1.86(1H, m), 2.86–2.88(2H, m), 3.34–3.43(2H, m), 4.66(2H, d, J=5.9 Hz), 5.63(1H, t, J=5.1 Hz), 6.49–6.55(2H, m), 6.85(1H, s), 7.05–7.17(2H, m), 7.76(1H, t, J=5.3 Hz), 8.35(1H, s), 9.07(1H, t, J=5.9 Hz), 9.24(1H, s).

REFERENCE EXAMPLE 86

2-(1-Perbenzoazepinyl)benzonitrile

According to a similar manner to that in Reference Example 12, the title compound was synthesized from 2-fluorobenzonitrile and hexamethyleneimine.

¹H-NMR (CDCl₃) δ (ppm): 1.59–1.64(4H, m), 1.86–1.87 (4H, m), 3.52–3.65(4H, m), 6.61–6.72(1H, m), 6.84(1H, d, J=8.6 Hz), 7.29–7.36(1H, m), 7.45(1H, d, J=7.9 Hz).

REFERENCE EXAMPLE 87

4-[2-(1-Perhydroazepinyl)benzylamino]-7-ethylamino-6-nitroquinazoline

The title compound was obtained from 4-chloro-7-ethylamino-6-nitroquinazoline and a compound obtained after the compound in Reference Example 86 was reduced by lithium aluminum hydride.

¹H-NMR (DMSO-d₆) δ (ppm): 1.29(3H, t, J=7.2 Hz), 1.61–1.90(8H, m), 3.06–3.14(4H, m), 3.33–3.44(2H, m), 4.85(2H, d, J=5.4 Hz), 6.87(1H, s), 6.93–6.99(1H, m), 7.09–7.22(3H, m), 7.74(1H, t, J=5.4 Hz), 8.32(1H, s), 9.06 (1H, t, J=5.4 Hz), 9.32(1H, s).

REFERENCE EXAMPLE 88

2-(1-Tricyclo[3.3.1.1$^{3.7}$]decyl)aminobenzonitrile

According to a similar manner to that in Reference Example 12, the title compound was obtained from 2-fluorobenzonitrile and 1-adamantanamine.

¹H-NMR (CDCl₃) δ (ppm): 1.67–1.76(7H, m), 1.99–2.01 (6H, m), 2.15–2.22(2H, m), 4.38(1H, br), 6.64(1H, dd, J=7.6 Hz, 7.6 Hz), 7.01(1H, d, J=8.6 Hz), 7.26–7.38(2H, m).

REFERENCE EXAMPLE 89

7-Ethylamino-6-nitro-4-[2-(1-tricyclo[3.3.1.1$^{3.7}$]decyl)aminobenzylamino]quinazoline The title compound was obtained from 4-chloro-7-ethylamino-6-nitroquinazoline and a compound obtained after the compound in Reference Example 88 was reduced by lithium aluminum hydride.

¹H-NMR (DMSO-d₆) δ (ppm): 1.27(3H, t, J=7.3 Hz), 1.56–1.70(6H, m), 1.80–1.90(6H, m), 2.00–2.09(3H, m), 3.32–3.43(2H, m), 4.68(2H, d, J=5.9 Hz), 4.95(1H, br), 6.62(1H, dd, J=7.3 Hz, 7.6 Hz), 6.87(1H, s), 6.92(1H, d, J=7.6 Hz), 7.07(1H, dd, J=7.3 Hz, 7.6 Hz), 7.19(1H, d, J=7.6 Hz), 7.77(1H, t, J=5.3 Hz), 8.36(1H, s), 9.04(1H, t, J=5.9 Hz), 9.26(1H, s).

REFERENCE EXAMPLE 90

2-(4-Hydroxybutylamino)benzonitrile

According to a similar manner to that in Reference Example 12, the title compound was synthesized from 2-fluorobenzonitrile and 4-hydroxybutylamine.

¹H-NMR (CDCl₃-CD₃OD) δ (ppm): 1.62–1.79(4H, m), 3.20–3.25(2H, m), 3.67–3.72(2H, m), 6.61–6.67(2H, m), 7.33–7.40(2H, m).

REFERENCE EXAMPLE 91

7-Ethylamino-4-[2-(4-hydroxybutylamino)benzylamino]-6-nitroquinazoline

The title compound was obtained from 4-chloro-7-ethylamino-6-nitroquinazoline and a compound obtained after the compound in Reference Example 90 was reduced by lithium aluminum hydride.

¹H-NMR (DMSO-d₆) δ (ppm): 1.27(3H, t, J=6.9 Hz), 1.45–1.64(4H, m), 3.00–3.08(2H, m), 3.33–3.47(4H, m), 4.40(1H, t, J=5.0 Hz), 4.63(2H, d, J=5.6 Hz), 5.62(1H, br), 6.52–6.55(2H, m), 6.85(1H, s), 7.06–7.15(2H, m), 7.76(1H, t, J=5.3 Hz), 8.36(1H, s), 9.08(1H, t, J=5.6 Hz), 9.24(1H, s).

REFERENCE EXAMPLE 92

6-Nitro-7-propyl-4(3H)-quinazoline

7-Chloro-6-nitro-4(3H)-quinazoline (5 g, 22.2 mmol) was heated at 140° C. in dimethylsulfoxide (15 ml). n-Propylamine (5 ml, 60.8 mmol) was added thereto at the same temperature and the mixture was stirred for 30 minutes. After the reaction was completed, the reaction mixture was cooled, and the crystal thus precipitated was collected, washed with methanol and dried to give the title compound.

¹H-NMR (DMSO-d₆) δ (ppm): 0.98(3H, t, J=7.4 Hz), 1.63–1.74(2H, m), 3.31–3.39(2H, m), 6.91(1H, s), 8.08(1H, s), 8.15(1H, t, J=5.3 Hz), 8.73(1H, s), 12.00(1H, br).

REFERENCE EXAMPLE 93

4-[2-(4-Hydroxymethylpiperidino)benzylamino]-6-nitro-7-propylaminoquinazoline

The compound (1.2 g, 4.84 mmol) obtained in Reference Example 92 was suspended in phosphorus oxychloride (11 ml, 118 mmol) and the mixture was heated at 110° C. for 2 hours under an argon gas atmosphere to form a clear solution. After it was confirmed that the starting material disappeared, unreacted phosphorus oxychloride was removed under reduced pressure. After the residue was subjected to azeotrope with toluene, the resulting oily substances were dissolved in the necessary minimum amount of tetrahydrofuran. The tetrahydrofuran solution obtained was poured onto ice-cold water with a sufficient amount of sodium hydrogen carbonate, followed by extraction with ethyl acetate. The organic layer was dried (over anhydrous magnesium sulfate), and the drying agent was filtered off. The filtrate was concentrated under reduced pressure to give orange solids (1.39 g).

The title compound was obtained from the above orange solids (1.39 g) and a compound obtained after the compound in Reference Example 13 was reduced by lithium aluminum hydride.

$^1$H-NMR (DMSO-d$_6$) δ (ppm): 1.00(3H, t, J=7.3 Hz), 1.26–1.63(3H, m), 1.66–1.79(4H, m), 2.62–2.70(2H. m), 3.06–3.15(2H, m), 3.29–3.36(4H, m), 4.47(1H, t, J=5.1 Hz), 4.84(2H, d, J=5.3 Hz), 6.87(1H, s), 6.96–7.09(1H, m), 7.11–7.25(3H, m), 7.83(1H, t, J=5.4 Hz), 8.33(1H, s), 9.11 (1H, t. J=5.3 Hz), 9.32(1H, s).

REFERENCE EXAMPLE 94

2-(4-Methyl-1-homopiperazinyl)benzonitrile

According to a similar manner to that in Reference Example 12, the title compound was synthesized from 2-fluorobenzonitrile and 4-methylhomopiperazine.

$^1$H-NMR (CDCl$_3$) δ (ppm): 2.01–2.10(2H, m), 2.41(3H, s), 2.63–2.67(2H, m), 2.80–2.84(2H, m), 3.59–3.68(2H, m), 3.69–3.71(2H, m), 6.71–6.78(1H, m), 6.85(1H, d, J=8.6 Hz), 7.33–7.45(1H, m), 7.47(1H, d, J=7.9 Hz).

REFERENCE EXAMPLE 95

7-Ethylamino-4-[2-(4-methyl-1-homopiperazinyl) benzylamino]-6-nitroquinazoline

The title compound was obtained from 4-chloro-7-ethylamino-6-nitroquinazoline and a compound obtained after the compound in Reference Example 94 was reduced by lithium aluminum hydride.

$^1$H-NMR (DMSO-d$_6$) δ (ppm): 1.31(3H, t, J=7.1 Hz), 2.10–2.27(2H, m), 2.81(3H, s), 3.09–3.18(2H, m), 3.20–3.42(8H, m), 4.87(2H, d, J=4.3 Hz), 6.87(1H, s), 7.04–7.10(1H, m), 7.21–7.30(3H, m), 7.76(1H, t, J=5.1 Hz), 8.33(1H, s), 9.17(1H, t, J=4.3 Hz), 9.36(1H, s).

REFERENCE EXAMPLE 96

2-[2-(2-Hydroxyethoxy)ethylamino]benzonitrile

According to a similar manner to that in Reference Example 12, the title compound was synthesized from 2-fluorobenzonitrile and 2-(2-aminoethoxy)ethanol.

$^1$H-NMR (CDCl$_3$) δ (ppm): 2.50(1H, br), 3.34–3.47(3H, m), 3.60–3.69(2H, m), 3.70–3.80(4H, m), 6.67–6.70(2H, m), 7.35–7.42(2H, m).

REFERENCE EXAMPLE 97

7-Ethylamino-4-{2-[2-(2-hydroxyethoxy) ethylamino]benzylamino}-6-nitroquinazoline The title compound was obtained from 4-chloro-7-ethylamino-6-nitroquinazoline and a compound obtained after the compound in Reference Example 96 was reduced by lithium aluminum hydride.

$^1$H-NMR (DMSO-d$_6$) δ (ppm): 1.27(3H, t, J=7.1 Hz), 3.21–3.30(2H, m), 3.36–3.45(6H, m), 3.58(2H, t, J=5.8 Hz), 4.56(1H, br), 4.63(2H, d, J=5.9 Hz), 5.67(1H, br), 6.55–6.61 (2H, m), 6.87(1H, s), 7.08–7.16(2H, m), 7.77(1H, t, J=5.3 Hz), 8.38(1H, s), 9.10(1H, t, J=5.9 Hz), 9.26(1H, s).

REFERENCE EXAMPLE 98

7-Methylamino-6-nitro-4(3H)-quinazoline

7-Chloro-6-nitro-4(3H)-quinazoline (6.06 g, 26.9 mmol) was heated at 110° C. in dimethylsulfoxide (20 ml). 40% aqueous methylamine solution (80 ml) was intermittently added thereto at the same temperature and the mixture was stirred for 30 minutes. After the reaction was completed, the reaction mixture was cooled, and the crystal thus precipitated was collected, washed with methanol and dried (5.38 g).

$^1$H-NMR (DMSO-d$_6$) δ (ppm): 3.04(3H, d, J=4.0 Hz), 6.90(1H, s), 8.24(1H, s), 8.28(1H, br), 8.81(1H, s), 12.00 (1H, br).

REFERENCE EXAMPLE 99

4-[2-(4-Hydroxymethylpiperidino)benzylamino]-7-methylamino-6-nitroquinazoline

The compound (7.0 g, 31.8 mmol) obtained in Reference Example 98 and N,N-diisopropylethylamine (10 ml, 57.4 mmol) were suspended in phosphorus oxychloride (80 ml, 858 mmol) and the mixture was heated at 110° C. for 2 hours under an argon gas atmosphere to form a clear solution. After it was confirmed that the starting material disappeared, unreacted phosphorus oxychloride was removed under reduced pressure. After the residue was subjected to azeotrope with toluene, the resulting oily substances were dissolved in the necessary minimum amount of tetrahydrofuran. The tetrahydrofuran solution obtained was poured into ice-cold water with a sufficient amount of sodium hydrogen carbonate, followed by extraction with ethyl acetate. The organic layer was dried (over anhydrous magnesium sulfate), and the drying agent was filtered off. The filtrate was concentrated under reduced pressure to give orange solids.

The title compound was obtained from the above orange solids and a compound obtained after the compound in Reference Example 13 was reduced by lithium aluminum hydride.

$^1$H-NMR (DMSO-d$_6$) δ (ppm): 1.28–1.56 (3H, m), 1.71–1.80 (2H, m), 2.52–2.73(2H, m), 2.99(3H, d, J=4.6 Hz), 3.01–3.12(2H, m), 3.23–3.42(2H, m), 4.47(1H, br), 4.84(2H, d, J=5.3 Hz), 6.82(1H, s), 6.96–7.02(1H, m), 7.11–7.25(3H, m), 7.93(1H, br), 8.28(1H, s), 9.08(1H, t, J=5.3 Hz), 9.31(1H, s).

REFERENCE EXAMPLE 100

2-(2-Furylmethylamino)benzonitrile

According to a similar manner to that in Reference Example 12, the title compound was synthesized from 2-fluorobenzonitrile and 2-(aminomethyl)furan.

$^1$H-NMR (CDCl$_3$) δ (ppm): 4.41(2H, s), 4.60(1H, br), 6.25–6.27(1H, m), 6.32–6.34(1H, m), 6.68–6.77(2H, m), 7.35–7.41(3H, m).

REFERENCE EXAMPLE 101

7-Ethylamino-4-[2-(2-furylmethylamino) benzylamino]- 6-nitroquinazoline

The title compound was obtained from 4-chloro-7-ethylamino-6-nitroquinazoline and a compound obtained after the compound in Reference Example 100 was reduced by lithium aluminum hydride.

$^1$H-NMR (CDCl$_3$) δ (ppm): 1.39(3H, t, J=7.1 Hz), 3.31–3.41(2H, m), 4.28(2H, s), 4.84(2H, s), 6.18–6.20(1H, m), 6.29–6.32(1H, m), 6.68–6.74(2H, m), 7.03(1H, s), 7.19–7.31(4H, m), 7.73(1H, br), 8.24(1H, s), 8.78(1H, s), 9.26(1H, s).

REFERENCE EXAMPLE 102

2-(1,2,3,4-Tetrahydroisoquinoline-2-yl)benzonitrile

According to a similar manner to that in Reference Example 12, the title compound was synthesized from 2-fluorobenzonitrile and 1,2,3,4-tetrahydroisoquinoline.

$^1$H-NMR (CDCl$_3$) δ (ppm): 3.07–3.11(2H, m), 3.65–3.69 (2H, m), 4.41(2H, s), 6.93–6.99(1H, m), 7.05–7.21(5H, m), 7.43–7.50(1H, m), 7.58(1H, dd, J=1.7 Hz, 7.6 Hz).

REFERENCE EXAMPLE 103

7-Ethylamino-6-nitro-4-(2-(1,2,3,4-tetrahydroisoquinoline-2-yl)benzylamino]quinazoline The title compound was obtained from 4-chloro-7-ethylamino-6-nitroquinazoline and a compound obtained after the compound in Reference Example 102 was reduced by lithium aluminum hydride.

$^1$H-NMR (CDCl$_3$) δ (ppm): 1.38(3H, t, J=7.3 Hz), 3.10–3.15(2H, m), 3.31–3.42(4H, m), 4.21(2H, s), 5.01(2H, d, J=4.0 Hz), 6.98(1H, s), 7.00–7.20(5H, m), 7.25–7.39(3H, m), 7.65(1H, br), 8.11(1H, t, J=4.0 Hz), 8.41(1H, s), 8.47 (1H, s).

REFERENCE EXAMPLE 104

2-(2-Tetrahydrofurylmethylamino)benzonitrile

According to a similar manner to that in Reference Example 12, the title compound was synthesized from 2-fluorobenzonitrile and 2-(tetrahydrofuryl)methylamine.

$^1$H-NMR (CDCl$_3$) δ (ppm): 1.60–1.73(1H, m), 1.86–2.11 (3H, m), 3.17–3.24(1H, m), 3.31–3.47(1H, m), 3.75–3.81 (1H, m), 3.83–3.96(1H, m), 4.09–4.19(1H, m), 4.39(1H, br), 6.63–6.72(2H, m), 7.27–7.40(2H, m).

REFERENCE EXAMPLE 105

7-Ethylamino-6-nitro-4-[2-(2-tetrahydrofurylmethylamino)benzylamino]quinazoline

The title compound was obtained from 4-chloro-7-ethylamino-6-nitroquinazoline and a compound obtained after the compound in Reference Example 104 was reduced by lithium aluminum hydride.

$^1$H-NMR (CDCl$_3$) δ (ppm): 1.40(3H, t, J=7.3 Hz), 1.53–1.63(1H, m), 1.80–2.01(3H, m), 3.03–3.11(1H, m), 3.20–3.26(1H, m), 3.32–3.43(2H, m), 3.64–3.78(2H, m), 4.02–4.09(1H, m), 4.83(2H, br), 5.20(1H, s), 6.66–6.73(2H, m), 6.80(1H, s), 7.02(1H, s), 7.19–7.26(2H, m), 7.72(1H, br), 8.53(1H, s), 8.79(1H, s).

REFERENCE EXAMPLE 106

2-(2-Thienylmethylamino)benzonitrile

According to a similar manner to that in Reference Example 12, the title compound was synthesized from 2-fluorobenzonitrile and 2-aminomethylthiophene.

$^1$H-NMR (CDCl$_3$) δ (ppm): 4.61(2H, s), 5.60(1H, br), 6.69–6.75(2H, m), 6.95–7.03(2H, m), 7.24(1H, d, J=7.6 Hz), 7.34–7.43(2H, m).

REFERENCE EXAMPLE 107

7-Ethylamino-6-nitro-4-[2-(2-thienylmethylamino) benzylamino]quinazoline

The title compound was obtained from 4-chloro-7-ethylamino-6-nitroquinazoline and a compound obtained after the compound in Reference Example 106 was reduced by lithium aluminum hydride.

$^1$H-NMR (CDCl$_3$) δ (ppm): 1.39(3H, t, J=7.3 Hz), 3.29–3.39(2H, m), 4.47(2H, d, J=4.3 Hz), 4.83(2H, d, J=5.9 Hz), 6.08(1H, br), 6.40(1H, t, J=4.3 Hz), 6.69–6.75(2H, m), 6.91–6.95(3H, m), 7.17–7.26(3H, m), 7.68(1H, t, J=5.9 Hz), 8.11(1H, s), 8.79(1H, s).

REFERENCE EXAMPLE 108

2-(2-Phenylaminoethylamino)benzonitrile

According to a similar manner to that in Reference Example 12, the title compound was synthesized from 2-fluorobenzonitrile and N-phenylethylenediamine.

$^1$H-NMR (CDCl$_3$) δ (ppm): 3.41–3.65(4H, m), 3.80(1H, br), 4.79(1H, br), 6.67–6.80(5H, m), 7.16–7.24(2H, m), 7.34–7.41(2H, m).

REFERENCE EXAMPLE 109

7-Ethylamino-6-nitro-4-[2-(2-phenylaminoethylamino)benzylamino]quinazoline

The title compound was obtained from 4-chloro-7-ethylamino-6-nitroquinazoline and a compound obtained after the compound in Reference Example 108 was reduced by lithium aluminum hydride.

$^1$H-NMR (CDCl$_3$) δ (ppm): 1.36(3H, t, J=7.3 Hz), 3.23–3.43(7H, m), 4.80(2H, d, J=4.6 Hz), 5.60(1H, br), 6.45–6.49(2H, m), 6.59–6.69(3H, m), 6.80–6.92(2H, m), 7.02–7.09(2H, m), 7.17–7.25(2H, m), 7.65(1H, t, J=4.6 Hz), 8.35(1H, s), 8.70(1H, s).

REFERENCE EXAMPLE 110

2-(4-Hydroxymethypiperidino)benzonitrile

Lithium aluminum hydride (0.90 g, 23.7 mmol) was suspended in tetrahydrofuran (20 ml), followed by stirring under ice-cooling in an argon gas atmosphere. A solution of 2-(4-ethoxycarbonylpiperidino)benzonitrile (6.00 g, 23.3 mmol) obtained in Reference Example 13, dissolved in tetrahydrofuran (50 ml), was dropwise and portionwise added thereto. After the addition was completed, the solution was stirred for 1 hour at the same temperature. After the reaction was completed, the reaction mixture was cooled and sodium sulfate decahydrate was portionwise added thereto until foaming ceased. Thereafter, the insolubles were filtered off and the filtrate was concentrated to give the title compound (5.0 g).

$^1$H-NMR (CDCl$_3$) δ (ppm): 1.43–1.74(4H, m), 1.83–1.92 (2H, m), 2.77–2.93(2H, m), 3.53–3.69(4H, m), 6.94–7.04 (2H, m), 7.43–7.53(1H. m), 7.55(1H, d, J=7.9 Hz).

REFERENCE EXAMPLE 111

2-(4-Methoxymethylpiperidino )benzonitrile

The compound (2.94 g, 13.6 mmol) obtained in Reference Example 110 was dissolved in N,N-dimethylformamide (14 ml) under cooling on ice and sodium hydride (40% in oil, 0.83 g, 21 mmol) was added thereto, the mixture was stirred for 2 hours at the same temperature, and methyl iodide (1.3 ml, 20.9 mmol) was added thereto. Thereafter, the mixture was stirred at 60° C. for 20 minutes. After the reaction was completed, the reaction mixture was poured into ice-cold water and extracted with ether, and the organic layer was dried (over anhydrous magnesium sulfate) and the organic layer was concentrated and purified by column chromatography (chloroform/ethyl acetate=10/1) to give the title compound (3.01 g, 96%).

$^1$H-NMR (CDCl$_3$) δ (ppm): 1.43–1.58(2H, m), 1.68–1.79 (1H, m), 1.80–1.90(2H, m), 2.75–2.84(2H, m), 3.29(2H, d, J=6.3 Hz), 3.36(3H, s), 3.53–3.62(2H, m), 6.93–7.12(2H, m), 7.41–7.50(1H, m), 7.53(1H, d, J=7.6 Hz).

REFERENCE EXAMPLE 112

7-Ethylamino-4-[2-(4-methoxymethylpiperidino) benzylamino]-6-nitroquinazoline

The title compound was obtained from 4-chloro-7-ethylamino-6-nitroquinazoline and a compound obtained after the compound in Reference Example 111 was reduced by lithium aluminum hydride.

$^1$H-NMR (DMSO-d$_6$) δ (ppm): 1.29(3H, t, J=7.1 Hz), 1.31–1.42(2H, m), 1.67–1.77(3H, m), 2.62–2.72(2H, m), 3.05–3.10(2H, m), 3.18(2H, d, J=4.3 Hz), 3.25(3H, s), 3.34–3.44(2H, m), 4.83(2H, d, J=5.3 Hz), 6.87(1H, s), 7.00(1H, dd, J=7.3 Hz, 7.3 Hz), 7.13(1H, d, J=7.9 Hz), 7.19–7.25(2H, m), 7.76(1H, t, J=5.4 Hz), 8.33(1H, s), 9.10 (1H, t, J=5.3 Hz), 9.31(1H, s).

REFERENCE EXAMPLE 113

2-(4-Ethoxymethylpiperidino)benzonitrile

According to a similar manner to that in Reference Example 111, the title compound was obtained from the compound obtained in Reference Example 110 and ethyl iodide.

$^1$H-NMR (CDCl$_3$) δ (ppm): 1.18(3H, t, J=7.1 Hz), 1.43–1.57(2H, m), 1.70–1.81(1H, m), 1.86–1.92(2H, m), 2.74–2.84(2H, m), 3.33(2H, d, J=6.6 Hz), 3.49(2H, q, J=7.1 Hz), 3.57–3.76(2H, m), 6.92–7.02(2H, m), 7.44(1H, dd, J=7.3 Hz, 8.6 Hz), 7.53(1H, d, J=7.6 Hz).

REFERENCE EXAMPLE 114

4-[2-(4-Ethoxymethylpiperidino)benzylamino]-7-ethylamino-6-nitroquinazoline

The title compound was obtained from 4-chloro-7-ethylamino-6-nitroquinazoline and a compound obtained after the compound in Reference Example 113 was reduced by lithium aluminum hydride.

$^1$H-NMR (DMSO-d$_6$) δ (ppm): 1.12(3H, t, J=6.9 Hz), 1.26–1.42(5H, m), 1.60–1.79(3H, m), 2.62–2.72(2H, m), 3.06–3.15(2H, m), 3.27(2H, d, J=5.9 Hz), 3.34–3.46(4H, m), 4.84(2H, d, J=5.0 Hz), 6.87(1H, s), 7.00(1H, dd, J=7.3 Hz, 7.6 Hz), 7.13(1H, d, J=7.9 Hz), 7.19–7.25(2H, m), 7.75(1H, t, J=5.3 Hz), 8.33(1H, s), 9.09(1H, t, J=5.0 Hz), 9.31(1H, s).

REFERENCE EXAMPLE 115

4-(2-Aminobenzylamino)-7-ethylamino-6-nitroquinazoline

4-Chloro-7-ethylamino-6-nitroquinazoline (5.00 g, 19.8 mmol), triethylamine (8.3 ml, 60.9 mmol), and 2-aminobenzylamino (2.9 g, 23.8 mmol) were stirred at room temperature overnight in tetrahydrofuran. After the reaction was completed, the solution was concentrated under reduced pressure, and the resulting solids were washed with methanol to give the title compound (5.23 g, 78%).

$^1$H-NMR (DMSO-d$_6$) δ (ppm): 1.28(3H, t, J=7.1 Hz), 3.33–3.45(4H, m), 4.59(2H, br), 5.27(1H, br), 6.52(1H, dd, J=7.3 Hz, 7.6 Hz), 6.64(1H, d, J=7.9 Hz), 6.85(1H, s), 6.96(1H, dd, J=7.3 Hz, 7.9 Hz), 7.08(1H, d, J=7.6 Hz), 7.77(1H, t, J=5.3 Hz), 8.34(1H, s), 9.27(1H, s).

REFERENCE EXAMPLE 116

4-[2-(tert-Butoxycarbonylamino)benzylamino]-7-ethylamino-6-nitroquinazoline

The compound (2.50 g, 7.40 mmol) obtained in Reference Example 115 was suspended in tetrahydrofuran (150 ml), and di-tert-butyl dicarbonate (7.2 ml, 31.3 mmol) and triethylamine (3.80 ml, 27.3 mmol) were added thereto, followed by stirring at room temperature overnight. After the reaction was completed, the reaction solution was concentrated under reduced pressure and the resulting solids were purified by column chromatography (chloroform/ethyl acetate=5/1) to give the title compound (2.80 g, 87%).

$^1$H-NMR (CDCl$_3$) δ (ppm): 1.37(3H, t, J=7.3 Hz), 1.56 (9H, s), 3.31–3.39(2H, m), 4.81(2H, d, J=5.6 Hz), 5.62(1H, br), 6.95–7.10(2H, m), 7.15–7.30(2H, m), 7.38(1H, d, J=7.3 Hz), 7.73–7.88(2H, m), 8.57(1H, s), 8.93(1H, s).

REFERENCE EXAMPLE 117

8-[2-(tert-Butoxycarbonylamino)benzylamino]-3-ethyl-2,3-dihydro-1H-imidazo[4,5-g]quinazoline-2-thione The compound (1.50 g, 3.42 mmol) obtained in Reference Example 116 was suspended in a mixed solvent of methanol (50 ml) and tetrahydrofuran (75 ml), 10% palladium on carbon catalyst (0.2 g) was added thereto, and the mixture was stirred overnight in a hydrogen gas atmosphere. After the reaction was completed, the catalyst was filtered off with a filter aid, then carbon disulfide (10 ml, 166 mmol) and triethylamine (10.0 ml, 71.8 mmol) were added to the filtrate, and the mixture was stirred at room temperature overnight. After the reaction was completed, the reaction mixture was concentrated under reduced pressure and the resulting solids were washed with methanol and purified by recrystallization (N,N-dimethylformamide/water) to give the title compound (1.04 g, 68%).

$^1$H-NMR (DMSO-d$_6$) δ (ppm): 1.30(3H, t, J=6.9 Hz), 1.50(9H, s), 4.35(2H, d, J=6.9 Hz), 4.69(2H, d, J=5.9 Hz), 7.03(1H, dd, J=7.3 Hz, 7.6 Hz), 7.23(1H, dd, J=7.3 Hz, 8.2 Hz), 7.37(1H, d, J=7.6 Hz), 7.62(1H, s), 7.73(1H, d, J=8.2 Hz), 8.01(1H, s), 8.44(1H, s), 8.98(1H, t, J=5.9 Hz), 10.28 (1H, br), 13.30(1H, s).

REFERENCE EXAMPLE 118

2-Cyclobutylaminobenzonitrile

According to a similar manner to that in Reference Example 12, the title compound was synthesized from 2-fluorobenzonitrile and cyclobutylamine.

$^1$H-NMR (CDCl$_3$) δ (ppm): 1.75–1.99(4H, m), 2.40–2.50 (2H, m), 3.91–4.01(1H, m), 4.50(1H, br), 6.57(1H, d, J=8.6 Hz), 6.65(1H, dd, J=7.3 Hz, 7.9 Hz), 7.32–7.40(2H, m).

REFERENCE EXAMPLE 119

4-(2-Cyclobutylaminobenzylamino)-7-ethylamino-6-nitroquinazoline

The title compound was obtained from 4-chloro-7-ethylamino-6-nitroquinazoline and a compound obtained after the compound in Reference Example 118 was reduced by lithium aluminum hydride.

¹H-NMR (CDCl₃) δ (ppm): 1.38(3H, t, J=7.3 Hz), 1.71–1.89(4H, m), 2.30–2.41(2H, m), 3.33–3.38(2H, m), 3.81–3.89(1H, m), 4.84(2H, br), 5.65(1H, br), 6.51(1H, d, J=7.9 Hz), 6.65(1H, dd, J=7.3 Hz, 7.6 Hz), 6.80(1H, br), 7.01(1H, s), 7.15–7.24(2H, m), 7.73(1H, t, J=4.8 Hz), 8.53 (1H, s), 8.80(1H, s).

REFERENCE EXAMPLE 120

2-(exo-2-Bicyclo[2.2.1]heptylamino)benzonitrile

According to a similar manner to that in Reference Example 12, the title compound was synthesized from 2-fluorobenzonitrile and exo-2-aminonorbornane.

¹H-NMR (CDCl₃) δ (ppm): 1.13–1.32(4H, m), 1.46–1.61 (3H, m), 1.81–1.90(1H, m), 2.26–2.38(2H, m), 3.26–3.30 (1H, m), 4.39(1H, br), 6.60–6.67(2H, m), 7.28–7.39(2H, m).

REFERENCE EXAMPLE 121

4-[2-(exo-2-Bicyclo[2.2.1]heptylamino) benzylamino]-7-ethylamino-6-nitroquinazoline The title compound was obtained from 4-chloro-7-ethylamino-6-nitroquinazoline and a compound obtained after the compound in Reference Example 120 was reduced by lithium aluminum hydride.

¹H-NMR (CDCl₃) δ (ppm): 1.04–1.27(5H, m), 1.34–1.55 (5H, m), 1.71–1.78(1H, m), 2.17–2.23(2H, m), 2.40(1H, br), 3.19–3.21(1H, m), 3.28–3.35(2H, m), 4.73–4.91(2H, m), 6.55–6.64(2H, m), 6.85(1H, br), 6.96(1H, s), 7.16–7.21(2H, m), 7.70(1H, t, J=4.6 Hz), 8.49(1H, s), 8.78(1H, s).

EXAMPLE 1

3-Ethyl-8-(2-methylaminobenzylamino)-2,3-dihydro-1H-imidazo[4,5-g]quinazoline-2-one 2 hydrochloride (Compound 1)

7-Ethylamino-4-(2-methyaminobenzylamino)-6-nitroquinazoline (4.00 g, 11.4 mmol) obtained in Reference Example 28 was suspended in a mixed solvent of methanol (100 ml) and tetrahydrofuran (150 ml). 10% palladium on carbon catalyst (0.40 g) was added to this suspension, and the mixture was stirred overnight in a hydrogen gas atmosphere. After the reaction was completed, the catalyst was filtered off with a filter aid and the resulting filtrate was divided into equal halves. One of the equal halves was concentrated under reduced pressure, then the resulting concentrated residue was dissolved in acetonitrile (100 ml), and N,N'-carbonyldiimidazole (2.80 g, 17.3 mmol) was added thereto, followed by stirring for 5 hours under heating at reflux. After the reaction was completed, the solvent was removed under reduced pressure and the resulting residue was purified by silica gel column chromatography (eluent: chloroform/methanol=100) to give a free base (1.31 g) of the title compound. The resulting free base was suspended in methanol (50 ml), and an excess amount of 4 N hydrochloric acid-ethyl acetate was added thereto under cooling on ice. The solution was concentrated to one half and the thus precipitated crystal was washed with ether-ethanol to give the title compound (1.48 g, 62%).

¹H-NMR (DMSO-d₆) δ (ppm): 1.28(3H, t, J=7.2 Hz), 2.92(3H, s), 3.95(2H, q, J=7.2 Hz), 4,60(1H, br), 4.90(2H, d, J=4.0 Hz), 6.94–7.05(2H, m), 7.26–7.35(2H, m), 7.49(1H, s), 8.22(1H, s), 8.84(1H, s), 10.61(1H, t, J=4.0 Hz), 11.98 (1H, s).

EXAMPLE 2

3-Ethyl-8-(4-methylaminobenzylamino)-2,3-dihydro-1H-imidazo[4,5-g]quinazoline-2-one 2 hydrochloride (Compound 2)

According to a similar manner to that in Example 1, the title compound was obtained from the compound as the starting material obtained in Reference Example 29.

¹H-NMR (DMSO-d₆) δ (ppm): 1.24(3H, t, J=7.3 Hz), 2.80(3H, s), 3.60(1H, br), 3.91(2H, q, J=7.3 Hz), 4.88(2H, d, J=5.6 Hz), 7.29(2H, d, J=8.3 Hz), 7.45(2H, d, J=8.3 Hz), 7.50(1H, s), 8.19(1H, s), 8.78(1H, s), 10.62(1H, t, J=5.6 Hz), 12.02(1H, s).

EXAMPLE 3

8-(4-Benzylaminobenzylamino)-3-ethyl-2,3-dihydro-1H-imidazo[4,5-g]quinazoline-2-one 2 hydrochloride (Compound 3)

According to a similar manner to that in Example 1, the title compound was obtained from the compound as the starting material obtained in Reference Example 30.

¹H-NMR (DMSO-d₆) δ (ppm): 1.27(3H, t, J=7.2 Hz), 3.94(2H, q, J=7.2 Hz), 4.37(2H, s), 4.83(2H, d, J=5.4 Hz), 6.90–7.00(2H, m), 7.20–7.45(8H, m), 7.48(1H, s), 8.15(1H, s), 8.78(1H, s), 10.46(1H, t, J=5.4 Hz), 11.98(1H, s).

EXAMPLE 4

3-Ethyl-8-(4-isopropylaminobenzylamino)-2,3-dihydro-1H-imidazo[4,5-g]quinazoline-2-one 2 hydrochloride (Compound 4)

According to a similar manner to that in Example 1, the title compound was obtained from the compound as the starting material obtained in Reference Example 31.

¹H-NMR (DMSO-d₆) δ (ppm): 1.23–1.31(9H, m), 3.61–3.66(2H, m), 3.95(2H, q, J=7.3 Hz), 4.94(2H, d, J=5.6 Hz), 7.41–7.53(5H, m), 8.17(1H, s), 8.81(1H, s), 10.53(1H, t, J=5.6 Hz), 11.99(1H, s).

EXAMPLE 5

3-Ethyl-8-(4-propylaminobenzylamino)-2,3-dihydro-1H-imidazo[4,5-g]quinazoline-2-one 2 hydrochloride (Compound 5)

According to a similar manner to that in Example 1, the title compound was obtained from the compound as the starting material obtained in Reference Example 32.

¹H-NMR (DMSO-d₆) δ (ppm): 0.93(3H, t, J=7.4 Hz), 1.27(3H, t, J=7.1 Hz), 1.58–1.71(2H, m), 3.10–3.16(2H, m), 3.60(1H, br), 3.94(2H, q, J=7.1 Hz), 4.90(2H, d, J=5.6 Hz), 7.29–7.35(2H, m), 7.43–7.48(3H, m), 8.17(1H, s), 8.81(1H, s), 10.54(1H, t, J=5.6 Hz), 12.01(1H, s).

EXAMPLE 6

3-Ethyl-8-(4-ethylaminobenzylamino)-2,3-dihydro-1H-imidazo[4,5-g]quinazoline-2-one 2 hydrochloride (Compound 6)

According to a similar manner to that in Example 1, the title compound was obtained from the compound as the starting material obtained in Reference Example 33.

¹H-NMR (DMSO-d₆) δ (ppm): 1.20–1.30(6H, m), 3.23 (2H, q, J=6.9 Hz), 3.61(1H, br), 3.95(2H, q, J=7.3 Hz), 4.91(2H, d, J=5.6 Hz), 7.29–7.40(2H, m), 7.44–7.50(3H, m), 8.15(1H, s), 8.81(1H, s), 10.49(1H, t, J=5.6 Hz), 11.99(1H, s).

EXAMPLE 7

3-Ethyl-8-[2-(2-morpholinoethylamino) benzylamino]-2,3-dihydro-1H-imidazo[4,5-g] quinazoline-2-one 3 hydrochloride (Compound 7)

According to a similar manner to that in Example 1, the title compound was obtained from the compound obtained in Reference Example 34.

¹H-NMR (DMSO-d₆) δ (ppm): 1.27(3H, t, J=6.9 Hz), 3.10–3.30(2H, m), 3.35–3.60(6H, m), 3.80–4.00(6H, m), 4.81(2H, d, J=5.4 Hz), 5.70(1H, br), 6.63(1H, dd, J=7.4 Hz, 7.4 Hz), 6.74(1H, d, J=7.9 Hz), 7.14(1H, dd, J=7.4 Hz, 7.9 Hz), 7.22(1H, d, J=7.4 Hz), 7.51(1H, s), 8.31(1H, s), 8.83 (1H, s), 10.65(1H, t, J=5.4 Hz), 12.00(1H, s).

EXAMPLE 8

3-Ethyl-8-[2-(3-morpholinopropylamino) benzylamino]-2,3-dihydro-1H-imidazo[4,5-g] quinazoline-2-one 3 hydrochloride (Compound 8)

According to a similar manner to that in Example 1, the title compound was obtained from the compound obtained in Reference Example 35.

¹H-NMR (DMSO-d₆) δ (ppm): 1.29(3H, t, J=7.2 Hz), 2.20–2.28(2H, m), 3.05–3.20(2H, m), 3.27–3.51(6H, m), 3.85–4.00(6H, m), 4.89(2H, d, J=5.4 Hz), 5.70(1H, br), 6.82(1H, dd, J=6.9 Hz, 6.9 Hz), 6.94(1H, d, J=7.9 Hz), 7.21(1H, dd, J=6.9 Hz, 7.9 Hz), 7.35(1H, d, J=6.9 Hz), 7.51(1H, s), 8.30(1H, s), 8.90(1H, s), 10.74(1H, t, J=5.4 Hz), 11.97(1H, s).

EXAMPLE 9

3-Ethyl-8-[2-(2-hydroxyethylamino)benzylamino]-2, 3-dihydro-1H-imidazo[4,5-g]quinazoline-2-one 2 hydrochloride (Compound 9)

The compound (0.91 g, 2.38 mmol) obtained in Reference Example 36 was suspended in a mixed solvent of methanol (90 ml) and tetrahydrofuran (72 ml), 10% palladium on carbon (50% water content, 0.50 g) was added thereto, and the mixture was stirred overnight in a hydrogen gas atmosphere. After the reaction was completed, the catalyst was filtered off with a filter aid and the resulting filtrate was concentrated under reduced pressure. The resulting concentrated residue was dissolved in N,N-dimethylacetamide (37 ml), and urea (1.21 g, 20.1 mmol) was added thereto, followed by stirring at 120° C. for 4 hours and then at 160° C. for 6 hours. After the reaction was completed, the solvent was removed under reduced pressure and the resulting residue was purified by silica gel column chromatography (eluent: chloroform/methanol=20) to give a free base (0.45 g) of the title compound. The resulting free base was suspended in methanol (10 ml), and an excess amount of 4 N hydrochloric acid-ethyl acetate was added thereto under cooling on ice. The solution was concentrated to one half and the precipitated crystal was washed with ether-methanol to give the title compound (0.28 g, 26%).

¹H-NMR (DMSO-d₆) δ (ppm): 1.27(3H, t, J=7.2 Hz), 3.37–3.42(2H, m), 3.74–3.78(2H, m), 3.93(2H, q, J=7.2 Hz), 4.91(2H, d, J=5.0 Hz), 4.98(1H, br), 6.30–6.70(1H, br), 7.05(1H, dd, J=6.9 Hz, 7.3 Hz), 7.18(1H, d, J=7.6 Hz), 7.31(1H, dd, J=7.3 Hz, 7.6 Hz), 7.44(1H, d, J=6.9 Hz), 7.53(1H, s), 8.25(1H, s), 8.85(1H, s), 10.83(1H, br), 12.04 (1H, s).

EXAMPLE 10

3-Ethyl-8-[2-(2-methoxyethylamino)benzylamino]-2,3-dihydro-1H-imidazo[4,5-g]quinazoline-2-one 2 hydrochloride (Compound 10)

According to a similar manner to that in Example 1, the title compound was obtained from the compound as the starting material obtained in Reference Example 38.

¹H-NMR (DMSO-d₆) δ (ppm): 1.28(3H, t, J=7.2 Hz), 3.27(3H, s), 3.42–3.49(2H, m), 3.63(2H, t, J=5.4 Hz), 3.94 (2H, q, J=7.2 Hz), 4.88(2H, d, J=5.4 Hz), 6.00–6.40(1H, m), 6.93(1H, dd, J=7.4 Hz, 7.4 Hz), 7.03(1H, d, J=7.9 Hz), 7.26(1H, dd, J=7.4 Hz, 7.9 Hz), 7.38(1H, d, J=7.4 Hz), 7.54(1H, s), 8.23(1H, s), 8.82(1H, s), 10.68(1H, br), 12.00 (1H, s).

EXAMPLE 11

3-Ethyl-8-(2-morpholinobenzylamino)-2,3-dihydro-1H-imidazo[4,5-g]quinazoline-2-one 1 hydrochloride (Compound 11)

7-Ethylamino-4-(2-morpholinobenzylamino)-6-nitroquinazoline (3.10 g, 7.60 mmol) obtained in Reference Example 39 was suspended in a mixed solvent of methanol (100 ml) and tetrahydrofuran (150 ml). 10% palladium on carbon catalyst (0.31 g) was added to this suspension, and the mixture was stirred for 8 hours at room temperature in a hydrogen gas atmosphere. After the reaction was completed, the catalyst was filtered of f with a filter aid and the resulting filtrate was divided into equal halves. One of the equal halves was concentrated under reduced pressure, then the resulting concentrated residue was dissolved in acetonitrile (100 ml), and N,N'-carbonyldiimidazole (1.80 g, 11.1 mmol) was added thereto, followed by stirring for 6 hours under heating at reflux. After the reaction was completed, the solvent was removed under reduced pressure and the resulting solids were collected and washed with water and methanol. The solids were further dried to give a free base (1.27 g) of the title compound. The resulting free base was suspended in methanol (50 ml), and an excess amount of 4 N hydrochloric acid-ethyl acetate was added thereto under cooling on ice. The solution was concentrated to one half and the precipitated crystal was washed with ether-ethanol to give the title compound (1.50 g, 89%).

¹H-NMR (DMSO-d₆) δ (ppm): 1.28(3H, t, J=7.1 Hz), 2.89–2.92(4H, m), 3.73–3.77(4H, m), 3.96(2H, q, J=7.1 Hz), 5.05(2H, d, J=5.3 Hz), 7.15(1H, dd, J=7.3 Hz, 7.9 Hz), 7.31–7.43(3H, m), 7.58(1H, s), 8.26(1H, s), 8.91(1H, s), 10.37(1H, br), 12.06(1H, s).

EXAMPLE 12

3-Ethyl-8-[2-(4-hydroxymethylpiperidino) benzylamino]-2,3-dihydro-1H-imidazo[4,5-g] quinazoline-2-one 2 hydrochloride (Compound 12)

According to a similar manner to that in Example 9, the title compound was obtained from the compound obtained in Reference Example 40.

¹H-NMR (DMSO-d₆) δ (ppm): 1.30(3H, t, J=7.2 Hz), 1.70–2.05(5H, m), 3.20–3.60(6H, m), 3.94(2H, q, J=7.2 Hz), 4.90(1H, br), 5.12(2H, s), 7.27–7.60(4H, m), 7.56(1H, s), 8.21(1H, s), 8.81(1H, s), 11.70(1H, br), 11.98(1H, s).

EXAMPLE 13

3-Ethyl-8-(2-piperidinobenzylamino)-2,3-dihydro-1H-imidazo[4,5-g]quinazoline-2-one 2 hydrochloride (Compound 13)

According to a similar manner to that in Example 11, the title compound was obtained from the compound obtained in Reference Example 41.

¹H-NMR (DMSO-d₆) δ (ppm): 1.28(3H, t, J=7.1 Hz), 1.62–1.75(2H, m), 1.80–1.98(4H, m), 4.00(2H, q, J=7.1 Hz), 4.20–4.43(4H, m), 5.08(2H, d, J=5.3 Hz), 7.23–7.34(1H, m), 7.36–7.58(3H, m), 7.62(1H, s), 8.28(1H, s), 8.92(1H, s), 10.60(1H, br), 12.08(1H, s).

EXAMPLE 14

3-Ethyl-8-[2-(4-methyl-1-piperazinyl)benzylamino]-2,3-dihydro-1H-imidazo[4,5-g]quinazoline-2-one 3 hydrochloride (Compound 14)

According to a similar manner to that in Example 11, the title compound was obtained from the compound obtained in Reference Example 42.

¹H-NMR (DMSO-d₆) δ (ppm): 1.28(3H, t, J=7.1 Hz), 2.85(3H, s), 3.23–3.44(6H, m), 3.50–3.54(2H, m), 3.95(2H, q, J=7.1 Hz), 5.03(2H, d, J=5.3 Hz), 7.10(1H, dd, J=6.6 Hz, 6.9 Hz), 7.22(1H, d, J=7.6 Hz), 7.27–7.33(2H, m), 7.57(1H, s), 8.27(1H, s), 8.79(1H, s), 10.51(1H, t, J=5.3 Hz), 12.04 (1H, s).

EXAMPLE 15

3-Ethyl-8-(2-thiomorpholinobenzylamino)-2,3-dihydro-1H-imidazo[4,5-g]quinazoline-2-one 1 hydrochloride (Compound 15)

According to a similar manner to that in Example 11, the title compound was obtained from the compound obtained in Reference Example 43.

¹H-NMR (DMSO-d₆) δ (ppm): 1.30(3H, t, J=7.2 Hz), 2.80–2.95(4H, m), 3.15–3.28(4H, m), 3.93(2H, q, J=7.2 Hz), 5.02(2H, d, J=5.4 Hz), 7.07(1H, dd, J=6.9 Hz, 7.4 Hz), 7.21–7.32(3H, m), 7.56(1H, s), 8.21(1H, s), 8.77(1H, s), 10.36(1H, t, J=5.4 Hz), 11.97(1H, s).

EXAMPLE 16

3-Ethyl-8-(3-morpholinobenzylamino)-2,3-dihydro-1H-imidazo[4,5-g]quinazoline-2-one 2 hydrochloride (Compound 16)

According to a similar manner to that in Example 11, the title compound was obtained from the compound obtained in Reference Example 44.

¹H-NMR (DMSO-d₆) δ (ppm): 1.29(3H, t, J=7.2 Hz), 3.23–3.31(4H, m), 3.85–4.00(6H, m), 4.93(2H, d, J=5.4 Hz), 7.11(1H, d, J=7.4 Hz), 7.23(1H, d, J=7.4 Hz), 7.32(1H, dd, J=7.4 Hz, 7.4 Hz), 7.42(1H, s), 7.53(1H, s), 8.21(1H, s), 8.79(1H, s), 10.57(1H, t, J=5.4 Hz), 11.98(1H, s).

EXAMPLE 17

3-Ethyl-8-(3-piperidinobenzylamino)-2,3-dihydro-1H-imidazo[4,5-g]quinazoline-2-one 2 hydrochloride (Compound 17)

According to a similar manner to that in Example 11, the title compound was obtained from the compound obtained in Reference Example 45.

¹H-NMR (DMSO-d₆) δ (ppm): 1.29(3H, t, J=7.1 Hz), 1.66–1.70(2H, m), 1.80–2.11(4H, m), 3.35–3.49(4H, m), 3.96(2H, q, J=7.1 Hz), 4.96(2H, d, J=5.3 Hz), 7.45–7.55(3H, m), 7.66–7.75(1H, m), 7.87–7.90(1H, m), 8.18(1H, s), 8.82 (1H, s), 10.57(1H, br), 12.00(1H, s).

EXAMPLE 18

3-Ethyl-8-[3-(4-methyl-1-piperazinyl)benzylamino]-2,3-dihydro-1H-imidazo[4,5-g]quinazoline-2-one 3 hydrochloride (Compound 18)

According to a similar manner to that in Example 11, the title compound was obtained from the compound obtained in Reference Example 46.

¹H-NMR (DMSO-d₆) δ (ppm): 1.30(3H, t, J=7.1 Hz), 2.82(3H, s), 3.15–3.23(4H, m), 3.43–3.51(2H, m), 3.74–3.82(2H, m), 3.93(2H, q, J=7.1 Hz), 4.90(2H, d, J=5.6 Hz), 6.88–6.95(2H, m), 7.10(1H, s), 7.23(1H, dd, J=7.9 Hz, 7.9 Hz), 7.54(1H, s), 8.24(1H, s), 8.82(1H, s), 10.57(1H, t, J=5.6 Hz), 12.00(1H, s).

EXAMPLE 19

3-Ethyl-8-(4-piperidinobenzylamino)-2,3-dihydro-1H-imidazo[4,5-g]quinazoline-2-one 2 hydrochloride (Compound 19)

According to a similar manner to that in Example 11, the title compound was obtained from the compound obtained in Reference Example 48.

¹H-NMR (DMSO-d₆) δ (ppm): 1.29(3H, t, J=6.9 Hz), 1.60–1.79(2H, m), 1.81–2.11(4H, m), 3.35–3.49(4H, m), 3.96(2H, q, J=6.9 Hz), 4.95(2H, d, J=5.6 Hz), 7.49(1H, s), 7.50–7.55(2H, m), 7.72–7.77(2H, m), 8.18(1H, s), 8.81(1H, s), 10.58(1H, br), 12.00(1H, s).

EXAMPLE 20

3-Ethyl-8-[4-(4-methyl-1-piperazinyl)benzylamino]-2,3-dihydro-1H-imidazo[4,5-g]quinazoline-2-one 3 hydrochloride (Compound 20)

According to a similar manner to that in Example 11, the title compound was obtained from the compound obtained in Reference Example 49.

¹H-NMR (DMSO-d₆) δ (ppm): 1.28(3H, t, J=7.1 Hz), 2.80(3H, s), 3.06–3.21(4H, m), 3.41–3.50(2H, m), 3.75–3.85(2H, m), 3.94(2H, q, J=7.1 Hz), 4.84(2H, d, J=5.6 Hz), 6.97(2H, d, J=8.9 Hz), 7.31(2H, d, J=8.9 Hz), 7.53(1H, s), 8.20(1H, s), 8.80(1H, s), 10.57(1H, t, J=5.6 Hz), 12.00 (1H, s).

EXAMPLE 21

3-Ethyl-8-(4-thiomorpholinobenzylamino)-2,3-dihydro-1H-imidazo[4,5-g]quinazoline-2-one 2 hydrochloride (Compound 21)

According to a similar manner to that in Example 11, the title compound was obtained from the compound obtained in Reference Example 51.

¹H-NMR (DMSO-d₆) δ (ppm): 1.29(3H, t, J=7.2 Hz), 2.90–3.10(4H, m), 3.55–3.70(4H, m), 3.95(2H, q, J=7.2 Hz), 4.90(2H, d, J=5.5 Hz), 7.35–7.47(4H, m), 7.50(1H, s), 8.19(1H, s), 8.79(1H, s), 10.55(1H, t, J=5.5 Hz), 11.98(1H, s).

EXAMPLE 22

3-Ethyl-8-(2-methylaminobenzylamino)-2,3-dihydro-1H-imidazo[4,5-g]quinazoline-2-thione 2 hydrochloride (Compound 22)

7-Ethylamino-4-(2-methylaminobenzylamino)-6-nitroquinazoline (4.00 g, 11.4 mmol) obtained in Reference Example 28 was suspended in a mixed solvent of methanol (100 ml) and tetrahydrofuran (150 ml). 10% palladium on carbon catalyst (0.40 g) was added to this suspension, and the mixture was stirred at room temperature overnight in a hydrogen gas atmosphere. After the reaction was completed, the catalyst was filtered off with a filter aid and the resulting filtrate was divided into equal halves. Triethylamine (1.60 ml, 11.5 mmol) and carbon disulfide (5.10 ml, 84.7 mmol) were added to one of the equal halves (not concentrated) and the mixture was stirred overnight at room temperature. After the reaction was completed, the solvent was removed under reduced pressure, ether was added to the resulting residue, and the precipitated crystal was collected and dried to give a free base (2.40 g) of the title compound. The resulting free base was suspended in methanol (80 ml), and an excess amount of 4 N hydrochloric acid-ethyl acetate was added thereto under cooling on ice. The solution was concentrated to one half and the precipitated crystal was washed with ether-ethanol to give the title compound (2.15 g, 86%).

¹H-NMR (DMSO-d₆) δ (ppm): 1.32(3H, t, J=7.2 Hz), 2.91(3H, s), 4.10(1H, br), 4.36(2H, q, J=7.2 Hz), 4.92(2H, br), 6.91–7.02(2H, m), 7.25–7.33(2H, m), 7.72(1H, s), 8.43 (1H, s), 8.89(1H, s), 10.77(1H, br), 13.73(1H, s).

EXAMPLE 23

3-Ethyl-8-(4-methylaminobenzylamino)-2,3-dihydro-1H-imidazo[4,5-g]quinazoline-2-thione 2 hydrochloride (Compound 23)

The compound (5.40 g, 15.3 mmol) obtained in Reference Example 29 was suspended in a mixed solvent of methanol (700 ml) and tetrahydrofuran (900 ml). 10% palladium on carbon catalyst (0.81 g) was added to this suspension, and the mixture was stirred at room temperature for 3.5 hours in a hydrogen gas atmosphere. After the reaction was completed, the catalyst was filtered off with a filter aid, and triethylamine (13.6 ml, 97.7 mmol) and carbon disulfide (51.0 ml, 847 mmol) were added to ¾ of the resulting filtrate, and the mixture was stirred at room temperature overnight. To complete the reaction, carbon disulfide (50.0 ml, 830 mmol) was added thereto, followed by further stirring at room temperature overnight. After the reaction was completed, the solvent was removed under reduced pressure and the resulting residue was purified by silica gel column chromatography (eluent: chloroform/methanol=80) to give a free base (1.05 g) of the title compound. The resulting free base was suspended in methanol (100 ml), and an excess amount of 4 N hydrochloric acid-ethyl acetate was added thereto under cooling on ice. The solution was concentrated to one half and the precipitated crystal was washed with ether-ethanol to give the title compound (0.780 g, 16%).

$^1$H-NMR (DMSO-d$_6$) δ (ppm): 1.30(3H, t, J=6.9 Hz), 2.82(3H, s), 3.60(1H, br), 4.35(2H, q, J=6.9 Hz), 4.93(2H, d, J=5.6 Hz), 7.32(2H, d, J=8.3 Hz), 7.49(2H, d, J=8.3 Hz), 7.75(1H, s), 8.41(1H, s), 8.86(1H, s), 10.83(1H, t, J=5.6 Hz), 13.79(1H, s).

EXAMPLE 24

8-(4-Benzylaminobenzylamino)-3-ethyl-2,3-dihydro-1H-imidazo[4,5-g]quinazoline-2-thione 2 hydrochloride (Compound 24)

According to a similar manner to that in Example 22, the title compound was obtained from the compound obtained in Reference Example 30.

$^1$H-NMR (DMSO-d$_6$) δ (ppm): 1.32(3H, t, J=7.2 Hz), 4.31–4.37(4H, m), 4.60(1H, br), 4.86(2H, d, J=5.4 Hz), 6.90–7.02(2H, m), 7.20–7.43(7H, m), 7.70(1H, s), 8.36(1H, s), 8.83(1H, s), 10.83(1H, t, J=5.4 Hz), 13.70(1H, s).

EXAMPLE 25

3-Ethyl-8-(4-isopropylaminobenzylamino)-2,3-dihydro-1H-imidazo[4,5-g]quinazoline-2-thione 2 hydrochloride (Compound 25)

According to a similar manner to that in Example 22, the title compound was obtained from the compound obtained in Reference Example 31.

$^1$H-NMR (DMSO-d$_6$) δ (ppm): 1.24–1.34(9H, m), 3.52–3.68(2H, m), 4.36(2H, q, J=7.3 Hz), 4.97(2H, d, J=5.3 Hz), 7.43–7.54(4H, m), 7.73(1H, s), 8.39(1H, s), 8.86(1H, s), 10.78(1H, t, J=5.3 Hz), 13.75(1H, s).

EXAMPLE 26

3-Ethyl-8-(4-propylaminobenzylamino)-2,3-dihydro-1H-imidazo[4,5-g]quinazoline-2-thione 2 hydrochloride (Compound 26)

According to a similar manner to that in Example 22, the title compound was obtained from the compound obtained in Reference Example 32.

$^1$H-NMR (DMSO-d$_6$) δ (ppm): 0.93(3H, t, J=7.3 Hz), 1.32(3H, t, J=6.9 Hz), 1.60–1.70(2H, m), 3.12(2H, t, J=7.4 Hz), 3.80(1H, br), 4.36(2H, q, J=6.9 Hz), 4.92(2H, d, J=5.3 Hz), 7.21–7.24(2H, m), 7.40–7.44(2H, m), 7.68(1H, s), 8.36(1H, s), 8.87(1H, s), 10.68(1H, br), 13.76(1H, s).

FAB-MASS: m/z calculated for $C_{21}H_{24}N_6S$ 392, observed 393(M+1).

EXAMPLE 27

3-Ethyl-8-(4-ethylaminobenzylamino)-2,3-dihydro-1H-imidazo[4,5-g]quinazoline-2-thione 2 hydrochloride (Compound 27)

According to a similar manner to that in Example 22, the title compound was obtained from the compound obtained in Reference Example 33.

$^1$H-NMR (DMSO-d$_6$) δ (ppm): 1.22–1.35(6H, m), 3.25 (2H, q, J=7.3 Hz), 3.60(1H, br), 4.36(2H, q, J=7.3 Hz), 4.95(2H, d, J=5.3 Hz), 7.37–7.40(2H, m), 7.47–7.51(2H, m), 7.70(1H, s), 8.38(1H, s), 8.86(1H, s), 10.74(1H, t, J=5.3 Hz), 13.74(1H, s).

EXAMPLE 28

3-Ethyl-8-[2-(2-morpholinoethylamino) benzylamino]-2,3-dihydro-1H-imidazo[4,5-g] quinazoline-2-thione 3 hydrochloride (Compound 28)

According to a similar manner to that in Example 22, the title compound was obtained from the compound obtained in Reference Example 34.

$^1$H-NMR (DMSO-d$_6$) δ (ppm): 1.32(3H, t, J=7.2 Hz), 3.10–3.30(2H, m), 3.35–3.60(6H, m), 3.85–4.00(4H, m), 4.35(2H, q, J=7.2 Hz), 4.60(1H, br), 4.86(2H, d, J=4.9 Hz), 6.64(1H, dd, J=7.4 Hz, 7.9 Hz), 6.76(1H, d, J=7.9 Hz), 7.15(1H, dd, J=7.4 Hz, 8.4 Hz), 7.24(1H, d, J=8.4 Hz), 7.77(1H, s), 8.53(1H, s), 8.89(1H, s), 10.85(1H, t, J=4.9 Hz), 13.75(1H, s).

EXAMPLE 29

3-Ethyl-8-[2-(3-morpholinopropylamino) benzylamino]-2,3-dihydro-1H-imidazo[4,5-g] quinazoline-2-thione 3 hydrochloride (Compound 29)

According to a similar manner to that in Example 22, the title compound was obtained from the compound obtained in Reference Example 35.

$^1$H-NMR (DMSO-d$_6$) δ (ppm): 1.33(3H, t, J=7.1 Hz), 2.20–2.24(2H, m), 3.00–3.15(2H, m), 3.25–3.48(6H, m), 3.90–3.97(4H, m), 4.35(2H, q, J=7.1 Hz), 4.88(2H, d, J=4.6 Hz), 5.00(1H, br), 6.73(1H, dd, J=7.3 Hz, 7.6 Hz), 6.82(1H, d, J=7.9 Hz), 7.18(1H, dd, J=7.6 Hz, 7.9 Hz), 7.30(1H, d, J=7.3 Hz), 7.74(1H, s), 8.51(1H, s), 8.96(1H, s), 10.89(1H, t, J=4.6 Hz), 13.72(1H, s).

EXAMPLE 30

3-Ethyl-8-[2-(2-hydroxyethylamino)benzylamino]-2,3-dihydro-1H-imidazo[4,5-g]quinazoline-2-thione 2 hydrochloride (Compound 30)

According to a similar manner to that in Example 22, the title compound was obtained from the compound obtained in Reference Example 36.

$^1$H-NMR (DMSO-d$_6$) δ (ppm): 1.32(3H, t, J=6.9 Hz), 3.30–3.42(2H, m), 3.71–3.77(2H, m), 4.35(2H, q, J=6.9 Hz), 4.91(2H, br), 6.50(1H, br), 6.70(1H, br), 6.85–7.02(2H, m), 7.23–7.38(2H, m), 7.71(1H, s), 8.39(1H, s), 8.90(1H, s), 10.75(1H, br), 13.73(1H, s).

EXAMPLE 31

3-Ethyl-8-[4-(2-hydroxyethylamino)benzylamino]-2,3-dihydro-1H-imidazo[4,5-g]quinazoline-2-thione 2 hydrochloride (Compound 31)

According to a similar manner to that in Example 22, the title compound was obtained from the compound obtained in Reference Example 37.

¹H-NMR (DMSO-d₆) δ (ppm): 1.32(3H, t, J=6.9 Hz), 3.25–3.28(2H, m), 3.66(2H, t, J=5.9 Hz), 4.36(2H, q, J=6.9 Hz), 4.94(2H, d, J=5.4 Hz), 5.10(1H, br), 6.70(1H, br), 7.34(2H, d, J=8.4 Hz), 7.47(2H, d, J=8.4 Hz), 7.73(1H, s), 8.40(1H, s), 8.84(1H, s), 10.77(1H, t, J=5.4 Hz), 13.72(1H, s).

EXAMPLE 32

3-Ethyl-8-[2-(2-methoxyethylamino)benzylamino]-2,3-dihydro-1H-imidazo[4,5-g]quinazoline-2-thione 2 hydrochloride (Compound 32)

According to a similar manner to that in Example 22, the title compound was obtained from the compound obtained in Reference Example 38.

¹H-NMR (DMSO-d₆) δ (ppm): 1.32(3H, t, J=7.1 Hz), 3.25(3H, s), 3.38–3.47(2H, m), 3.60(2H, t, J=5.3 Hz), 4.35 (2H, q, J=7.1 Hz), 4.90(2H, d, J=4.6 Hz), 5.80(1H, br), 6.84–6.97(2H, m), 7.22–7.24(2H, m), 7.75(1H, s), 8.41(1H, s), 8.88(1H, s), 10.82(1H, br), 13.20(1H, s).

EXAMPLE 33

3-Ethyl-8-(2-morpholinobenzylamino)-2,3-dihydro-1H-imidazo[4,5-g]quinazoline-2-thione 1 hydrochloride (Compound 33)

7-Ethylamino-4-(2-morpholinobenzylamino)-6-nitroquinazoline (2.00 g, 4.90 mmol) obtained in Reference Example 39 was suspended in a mixed solvent of methanol (100 ml) and tetrahydrofuran (150 ml). 10% palladium on carbon catalyst (0.20 g) was added to this suspension, and the mixture was stirred at room temperature overnight in a hydrogen gas atmosphere. After the reaction was completed, the catalyst was filtered off with a filter aid, and triethylamine (1.40 ml, 10.1 mmol) and carbon disulfide (3.00 ml, 49.9 mmol) were added to the resulting filtrate, and the mixture was stirred at room temperature overnight. To complete the reaction, it was stirred at 50° C. for 2 hours. After the reaction was completed, the solvent was removed under reduced pressure and the resulting solids were collected. The solids were re-crystallized (twice) from N,N-dimethylformamide/water and further purified by silica gel column chromatography (eluent: chloroform/methanol= 100) to give a free base of the title compound. The resulting free base was suspended in methanol (50 ml), and an excess amount of 4 N hydrochloric acid-ethyl acetate was added thereto under cooling on ice. The solution was concentrated to one half and the precipitated crystal was collected to give the title compound (1.66 g, 74%).

¹H-NMR (DMSO-d₆) δ (ppm): 1.32(3H, t, J=6.9 Hz), 2.91–2.94(4H, m), 3.75–3.78(4H, m), 4.36(2H, q, J=6.9 Hz), 5.08(2H, d, J=5.3 Hz), 7.08(1H, dd, J=7.3 Hz, 8.9 Hz), 7.22–7.34(3H, m), 7.77(1H, s), 8.42(1H, s), 8.85(1H, s), 10.58(1H, t, J=5.3 Hz), 13.72(1H, s).

FAB-MASS: m/z calculated for C₂₂H₂₄N₆OS 420, observed 421(M+1).

EXAMPLE 34

3-Ethyl-8-[2-(4-hydroxymethylpiperidino) benzylamino]-2,3-dihydro-1H-imidazo[4,5-g] quinazoline-2-thione 2 hydrochloride (Compound 34)

According to a similar manner to that in Example 33, the title compound was obtained from the compound obtained in Reference Example 40.

¹H-NMR (DMSO-d₆) δ (ppm): 1.33(3H, t, J=6.9 Hz), 1.50–1.94(5H, m), 3.20–3.50(6H, m), 4.33(2H, q, J=6.9 Hz), 4.80(1H, br), 5.16(2H, d, J=4.6 Hz), 7.15–7.60(4H, m), 7.80(1H, s), 8.43(1H, s), 8.87(1H, s), 10.89(1H, br), 13.71 (1H, s).

FAB-MASS: m/z calculated for C₂₄H₂₈N₆OS 448, observed 449(M+1).

EXAMPLE 35

3-Ethyl-8-(2-piperidinobenzylamino)-2,3-dihydro-1H-imidazo[4,5-g]quinazoline-2-thione 2 hydrochloride (Compound 35)

According to a similar manner to that in Example 33, the title compound was obtained from the compound obtained in Reference Example 41.

¹H-NMR (DMSO-d₆) δ (ppm): 1.32(3H, t, J=7.1 Hz), 1.64–1.91(6H, mn), 4.32–4.50(6H, m), 5.12(2H, d, J=4.3 Hz), 7.10–7.35(1H, m), 7.40–7.60(3H, m), 7.77(1H, s), 8.41(1H, s), 8.88(1H, s), 10.76(1H, br), 13.73(1H, s).

FAB-MASS: m/z calculated for C₂₃H₂₆N₆S 418, observed 419(M+1).

EXAMPLE 36

3-Ethyl-8-[2-(4-methyl-1-piperazinyl)benzylamino]-2,3-dihydro-1H-imidazo[4,5-g]quinazoline-2-thione 3 hydrochloride (Compound 36)

According to a similar manner to that in Example 33, the title compound was obtained from the compound obtained in Reference Example 42.

¹H-NMR (DMSO-d₆) δ (ppm): 1.32(3H, t, J=7.1 Hz), 2.85(3H, s), 3.23–3.30(6H, m), 3.46–3.52(2H, m), 4.36(2H, q, J=7.1 Hz), 5.06(2H, d, J=5.3 Hz), 7.11(1H, dd, J=6.9 Hz, 7.9 Hz), 7.23(1H, d, J=7.6 Hz), 7.29–7.35(2H, m), 7.80(1H, s), 8.47(1H, s), 8.85(1H, s), 10.69(1H, t, J=5.3 Hz), 13.75 (1H, s).

EXAMPLE 37

3-Ethyl-8-(2-thiomorpholinobenzylamino)-2,3-dihydro-1H-imidazo[4,5-g]quinazoline-2-thione 1 hydrochloride (Compound 37)

According to a similar manner to that in Example 33, the title compound was obtained from the compound obtained in Reference Example 43.

¹H-NMR (DMSO-d₆) δ (ppm): 1.33(3H, t, J=6.9 Hz), 2.72–2.91(4H, m), 3.15–3.20(4H, m), 4.36(2H, q, J=6.9 Hz), 5.04(2H, d, J=5.4 Hz), 7.07(1H, dd, J=7.4 Hz, 7.4 Hz), 7.21–7.33(3H, m), 7.76(1H, s), 8.42(1H, s), 8.84(1H, s), 10.55(1H, t, J=5.4 Hz), 13.70(1H, s).

EXAMPLE 38

3-Ethyl-8-(3-morpholinobenzylamino)-2,3-dihydro-1H-imidazo[4,5-g]quinazoline-2-thione 2 hydrochloride (Compound 38)

According to a similar manner to that in Example 33, the title compound was obtained from the compound obtained in Reference Example 44.

¹H-NMR (DMSO-d₆) δ (ppm): 1.33(3H, t, J=7.2 Hz), 3.20–3.25(4H, m), 3.80–3.90(4H, m), 4.36(2H, q, J=7.2 Hz), 4.94(2H, d, J=5.4 Hz), 7.01(1H, d, J=7.4 Hz), 7.10(1H, d, J=7.9 Hz), 7.22–7.31(2H, m), 7.73(1H, s), 8.40(1H, s), 8.85(1H, s), 10.70(1H, t, J=5.4 Hz), 13.70(1H, s).

FAB-MASS: m/z calculated for C₂₂H₂₄N₆OS 420, observed 421(M+1).

EXAMPLE 39

3-Ethyl-8-(3-piperidinobenzylamino)-2,3-dihydro-1H-imidazo[4,5-g]quinazoline-2-thione 2 hydrochloride (Compound 39)

According to a similar manner to that in Example 33, the title compound was obtained from the compound obtained in Reference Example 45.

¹H-NMR (DMSO-d₆) δ (ppm): 1.32(3H, t, J=7.1 Hz), 1.66–2.13(6H, m), 3.44–3.62(4H, m), 4.36(2H, q, J=7.1 Hz), 4.98(2H, d, J=5.3 Hz), 7.36–7.50(2H, m), 7.55–7.73(2H, m), 7.78–7.90(1H, m), 8.40(1H, s), 8.88(1H, s), 10.80(1H, br), 13.75(1H, s).

FAB-MASS: m/z calculated for $C_{23}H_{26}N_6S$ 418, observed 419(M+1).

EXAMPLE 40

3-Ethyl-8-[3-(4-methyl-1-piperazinyl)benzylamino]-2,3-dihydro-1H-imidazo[4,5-g]quinazoline-2-thione 3 hydrochloride (Compound 40)

According to a similar manner to that in Example 33, the title compound was obtained from the compound obtained in Reference Example 46.

¹H-NMR (DMSO-d₆) δ (ppm): 1.23(3H, t, J=7.1 Hz), 2.72(3H, s), 3.06–3.13(4H, m), 3.39–3.42(2H, m), 3.68–3.71(2H, m), 4.27(2H, q, J=7.1 Hz), 4.83(2H, d, J=5.3 Hz), 6.79–6.86(2H, m), 7.00(1H, s), 7.14(1H, dd, J=7.9 Hz, 7.9 Hz), 7.65(1H, s), 8.33(1H, s), 8.77(1H, s), 10.65(1H, t, J=5.3 Hz), 13.65(1H, s).

EXAMPLE 41

3-Ethyl-8-(4-morpholinobenzylamino)-2,3-dihydro-1H-imidazo[4,5-g]quinazoline-2-thione 2 hydrochloride (Compound 41)

According to a similar manner to that in Example 33, the title compound was obtained from the compound obtained in Reference Example 47.

¹H-NMR (DMSO-d₆) δ (ppm): 1.30(3H, t, J=7.1 Hz), 3.14–3.16(4H, m), 3.76–3.80(4H, m), 4.34(2H, q, J=7.1 Hz), 4.87(2H, d, J=5.6 Hz), 7.07(2H, d, J=8.4 Hz), 7.34(2H, d, J=8.4 Hz), 7.72(1H, s), 8.38(1H, s), 8.86(1H, s), 10.70(1H, br), 13.76(1H, s).

EXAMPLE 42

3-Ethyl-8-(4-piperidinobenzylamino)-2,3-dihydro-1H-imidazo[4,5-g]quinazoline-2-thione 2 hydrochloride (Compound 42)

According to a similar manner to that in Example 33, the title compound was obtained from the compound obtained in Reference Example 48.

¹H-NMR (DMSO-d₆) δ (ppm): 1.31(3H, t, J=7.1 Hz), 1.50–1.79(2H, m), 1.80–2.10(4H, m), 3.50–3.90(4H, m), 4.36(2H, q, J=7.1 Hz), 4.97(2H, d, J=5.3 Hz), 7.56(2H, d, J=7.9 Hz), 7.70–7.87(3H, m), 8.41(1H, s), 8.86(1H, s), 10.83(1H, br), 13.76(1H, s).

EXAMPLE 43

3-Ethyl-8-[4-(4-methyl-1-piperazinyl)benzylamino]-2,3-dihydro-1H-imidazo[4,5-g]quinazoline-2-thione 3 hydrochloride (Compound 43)

According to a similar manner to that in Example 33, the title compound was obtained from the compound obtained in Reference Example 49.

¹H-NMR (DMSO-d₆) δ (ppm): 1.31(3H, t, J=7.1 Hz), 2.80(3H, s), 3.06–3.21(4H, m), 3.41–3.49(2H, m), 3.75–3.80(2H, m), 4.33(2H, q, J=7.1 Hz), 4.87(2H, d, J=5.6 Hz), 6.97(2H, d, J=8.6 Hz), 7.32(2H, d, J=8.6 Hz), 7.74(1H, s), 8.39(1H, s), 8.86(1H, s), 10.72(1H, t, J=5.6 Hz), 13.75(1H, s).

EXAMPLE 44

3-Ethyl-8-[4-(1-pyrrolidinyl)benzylamino]-2,3-dihydro-1H-imidazo[4,5-g]quinazoline-2-thione 2 hydrochloride (Compound 44)

According to a similar manner to that in Example 33, the title compound was obtained from the compound obtained in Reference Example 50.

¹H-NMR (DMSO-d₆) δ (ppm): 1.31(3H, t, J=7.1 Hz), 1.99–2.05(4H, m), 3.20–3.30(4H, m), 4.34(2H, q, J=7.1 Hz), 4.85(2H, d, J=5.6 Hz), 6.70–6.78(2H, m), 7.29–7.39(2H, m), 7.73(1H, s), 8.38(1H, s), 8.85(1H, s), 10.68(1H, t, J=5.6 Hz), 13.72(1H, s).

EXAMPLE 45

3-Ethyl-8-(4-thiomorpholinobenzylamino)-2,3-dihydro-1H-imidazo[4,5-g]quinazoline-2-thione 2 hydrochloride (Compound 45)

According to a similar manner to that in Example 33, the title compound was obtained from the compound obtained in Reference Example 51.

¹H-NMR (DMSO-d₆) δ (ppm): 1.31(3H, t, J=7.2 Hz), 2.85–3.05(4H, m), 3.55–3.70(4H, m), 4.35(2H, q, J=7.2 Hz), 4.91(2H, d, J=5.4 Hz), 7.30–7.52(4H, m), 7.74(1H, s), 8.39(1H, s), 8.86(1H, s), 10.75(1H, t, J=5.4 Hz), 13.74(1H, s).

EXAMPLE 46

3-Ethyl-8-{2-[N-(2-hydroxyethyl)methylamino]benzylamino}-2,3-dihydro-1H-imidazo[4,5-g]quinazoline-2-thione 2 hydrochloride (Compound 46)

According to a similar manner to that in Example 33, the title compound was obtained from the compound obtained in Reference Example 53.

¹H-NMR (DMSO-d₆) δ (ppm): 1.31(3H, t, J=7.1 Hz), 3.25(3H, s), 3.80–3.90(4H, m), 4.20(1H, br), 4.35(2H, q, J=7.1 Hz), 5.13(2H, br), 7.35–7.60(3H, m), 7.75–7.80(2H, m), 8.45(1H, s), 8.99(1H, s), 11.07(1H, s), 13.70(1H, s).

EXAMPLE 47

3-Ethyl-8-[4-(3-hydroxymethylpiperidino)benzylamino]-2,3-dihydro-1H-imidazo[4,5-g]quinazoline-2-thione 2 hydrochloride (Compound 47)

According to a similar manner to that in Example 33, the title compound was obtained from the compound obtained in Reference Example 55.

¹H-NMR (DMSO-d₆) δ (ppm): 1.31(3H, t, J=7.1 Hz), 1.80–2.15(3H, m), 2.20–2.60(3H, m), 3.40–4.00(6H, m), 4.34(2H, q, J=7.1 Hz), 4.96(2H, d, J=5.6 Hz), 7.53–7.79(5H, m), 8.29(1H, s), 8.87(1H, s), 10.75(1H, br), 13.70(1H, s).

EXAMPLE 48

3-Ethyl-8-(4-morpholinobenzylamino)-2,3-dihydro-1H-imidazo[4,5-g]quinazoline-2-one 2 hydrochloride (Compound 48)

According to a similar manner to that in Example 1, the title compound was obtained from the compound as the starting material obtained in Reference Example 47.

¹H-NMR (DMSO-d₆) δ (ppm): 1.26(3H, t, J=6.9 Hz), 3.17–3.20(4H, m), 3.84–3.97(6H, m), 4.87(2H, d, J=5.3 Hz), 7.24–7.27(2H, m), 7.39–7.43(2H, m), 7.53(1H, s), 8.22(1H, s), 8.79(1H, s), 10.02(1H, br), 12.03(1H, s).

EXAMPLE 49

3-Ethyl-8-[4-(2-hydroxyethylamino)benzylamino]-2,3-dihydro-1H-imidazo[4,5-g]quinazoline-2-one 2 hydrochloride (Compound 49)

According to a similar manner to that in Example 9, the title compound was obtained from the compound as the starting material obtained in Reference Example 37.

¹H-NMR (DMSO-d₆) δ (ppm): 1.26(3H, t, J=7.1 Hz), 3.26–3.30(2H, m), 3.64–3.68(2H, m), 3.93(2H, q, J=7.1 Hz), 4.07(1H, br), 4.91(2H, d, J=5.6 Hz), 6.50(1H, br), 7.38(2H, d, J=8.2 Hz), 7.49(2H, d, J=8.2 Hz), 7.52(1H, s), 8.23(1H, s), 8.80(1H, s), 10.70(1H, br), 12.04(1H, s).

EXAMPLE 50

3-Ethyl-8-[2-(1-imidazolyl)benzylamino]-2,3-dihydro-1H-imidazo[4,5-g]quinazoline-2-one 3 hydrochloride (Compound 50)

According to a similar manner to that in Example 1, the title compound was obtained from the compound as the starting material obtained in Reference Example 57.

¹H-NMR (DMSO-d₆) δ (ppm): 1.26(3H, t, J=7.3 Hz), 3.93(2H, q, J=7.3 Hz), 4.74(2H, d, J=5.3 Hz), 7.54–7.65(4H, m), 7.80(1H, d, J=7.6 Hz), 7.90(1H, s), 8.12(1H, s), 8.25(1H, s), 8.71(1H, s), 9.61(1H, s), 10.86(1H, t, J=5.3 Hz), 12.05(1H, s).

EXAMPLE 51

3-Ethyl-8-[2-(1-imidazolyl)benzylamino]-2,3-dihydro-1H-imidazo[4,5-g]quinazoline-2-thione 3 hydrochloride (Compound 51)

According to a similar manner to that in Example 22, the title compound was obtained from the compound as the starting material obtained in Reference Example 57.

¹H-NMR (DMSO-d₆) δ (ppm): 1.30(3H, t, J=7.1 Hz), 4.34(2H, q, J=7.1 Hz), 4.78(2H, d, J=5.0 Hz), 7.53–7.67(3H, m), 7.77–7.82(2H, m), 7.90(1H, s), 8.10(1H, s), 8.41(1H, s), 8.77(1H, s), 9.60(1H, s), 10.94(1H, br), 13.78(1H, s).

EXAMPLE 52

8-[2-(1-Perhydroazocinyl)benzylamino]-3-ethyl-2,3-dihydro-1H-imidazo[4,5-g]quinazoline-2-one 2 hydrochloride (Compound 52)

According to a similar manner to that in Example 1, the title compound was obtained from the compound as the starting material obtained in Reference Example 59.

¹H-NMR (DMSO-d₆) δ (ppm): 1.28(3H, t, J=7.1 Hz), 1.60–1.90(10H, m), 3.10–3.30(4H, m), 3.96(2H, q, J=7.1 Hz), 5.09(2H, d, J=5.3 Hz), 7.00–7.40(4H, m), 7.56(1H, s), 8.25(1H, s), 8.79(1H, s), 10.54(1H, br), 12.03(1H, s).

EXAMPLE 53

8-[2-(1-Perhydroazocinyl)benzylamino]-3-ethyl-2,3-dihydro-1H-imidazo[4,5-g]quinazoline-2-thione 2 hydrochloride (Compound 53)

According to a similar manner to that in Example 22, the title compound was obtained from the compound as the starting material obtained in Reference Example 59.

¹H-NMR(DMSO-d₆) δ (ppm): 1.31(3H, t, J=7.1 Hz), 1.60–1.90(10H, m), 3.15–3.30(4H, m), 4.35(2H, q, J=7.1 Hz), 5.13(2H, d, J=5.3 Hz), 7.05–7.42(4H, m), 7.82(1H, s), 8.48(1H, s), 8.85(1H, s), 10.81(1H, br), 13.80(1H, s).

EXAMPLE 54

3-Ethyl-8-(2-propylaminobenzylamino)-2,3-dihydro-1H-imidazo[4,5-g]quinazoline-2-one 2 hydrochloride (Compound 54)

According to a similar manner to that in Example 1, the title compound was obtained from the compound obtained in Reference Example 61.

¹H-NMR (DMSO-d₆) δ (ppm): 0.94(3H, t, J=7.4 Hz), 1.25(3H, t, J=7.1 Hz), 1.70–1.78(2H, m), 3.20–3.26(2H, m), 3.91(2H, q, J=7.1 Hz), 4.80(1H, br), 4.93(2H, d, J=4.3 Hz), 6.95–7.05(1H, m), 7.10–7.20(1H, m), 7.29(1H, dd, J=5.9 Hz, 7.3 Hz), 7.39(1H, d, J=7.3 Hz), 7.53(1H, s), 8.23(1H, s), 8.82(1H, s), 10.74(1H, br), 12.01(1H, s).

EXAMPLE 55

3-Ethyl-8-(2-propylaminobenzylamino)-2,3-dihydro-1H-imidazo[4,5-g]quinazoline-2-thione 2 hydrochloride (Compound 55)

According to a similar manner to that in Example 22, the title compound was obtained from the compound obtained in Reference Example 61.

¹H-NMR (DMSO-d₆) δ (ppm): 0.96(3H, t, J=7.4 Hz), 1.30(3H, t, J=7.1 Hz), 1.69–1.78(2H, m), 3.20–3.26(2H, m), 4.34(2H, q, J=7.1 Hz), 4.50(1H, br), 4.96(2H, br), 6.90–7.00(1H, m), 7.01–7.15(1H, m), 7.26–7.38(2H, m), 7.78(1H, s), 8.45(1H, s), 8.90(1H, s), 10.88(1H, br), 13.78(1H, s).

EXAMPLE 56

3-Ethyl-8-(2-isopropylaminobenzylamino)-2,3-dihydro-1H-imidazo[4,5-g]quinazoline-2-thione 2 hydrochloride (Compound 56)

According to a similar manner to that in Example 22, the title compound was obtained from the compound obtained in Reference Example 63.

¹H-NMR (DMSO-d₆) δ (ppm): 1.27–1.35(9H, m), 3.60–4.00(2H, m), 4.35(2H, q, J=7.1 Hz), 5.01(2H, br), 7.10–7.22(1H, m), 7.23–7.48(3H, m), 7.77(1H, s), 8.44(1H, s), 8.91(1H, s), 10.90(1H, br), 13.81(1H, s).

EXAMPLE 57

3-Ethyl-8-[2-(3-hydroxymethylpiperidino)benzylamino]-2,3-dihydro-1H-imidazo[4,5-g]quinazoline-2-one 2 hydrochloride (Compound 57)

According to a similar manner to that in Example 9, the title compound was obtained from the compound as the starting material obtained in Reference Example 65.

¹H-NMR (DMSO-d₆) δ (ppm): 1.27(3H, t, J=6.9 Hz), 1.75–2.20(3H, m), 2.80–3.20(3H, m), 3.30–3.55(4H, m), 3.85–4.20(4H, m), 5.08(2H, br), 7.17–7.50(4H, m), 7.56(1H, s), 8.22(1H, s), 8.81(1H, s), 10.60(1H, br), 12.03(1H, s).

EXAMPLE 58

3-Ethyl-8-[3-(4-hydroxymethylpiperidino)benzylamino]-2,3-dihydro-1H-imidazo[4,5-g]quinazoline-2-thione 2 hydrochloride (Compound 58)

According to a similar manner to that in Example 33, the title compound was obtained from the compound as the starting material obtained in Reference Example 67.

¹H-NMR (DMSO-d₆) δ (ppm): 1.30(3H, t, J=6.9 Hz), 1.70–2.00(4H, m), 3.40–3.80(8H, m), 4.35(2H, q, J=6.9 Hz), 4.98(2H, d, J=5.6 Hz), 7.46–7.49(2H, m), 7.60–7.95(3H, m), 8.43(1H, s), 8.88(1H, s), 10.87(1H, br), 13.79(1H, s).

EXAMPLE 59

3-Ethyl-8-{2-[4-(2-hydroxyethyl)piperidino]benzylamino}-2,3-dihydro-1H-imidazo[4,5-g]quinazoline-2-thione 2 hydrochloride (Compound 59)

According to an almost similar manner to that in Example 22, the title compound was obtained from the compound as the starting material obtained in Reference Example 69.

$^1$H-NMR (DMSO-d$_6$) δ (ppm): 1.31(3H, t, J=6.9 Hz), 1.46–1.56(2H, m), 1.60–2.00(4H, m), 3.10–3.43(5H, m), 3.45–3.52(2H, m), 4.35(2H, q, J=6.9 Hz), 4,50(1H, br), 5.10(2H, br), 7.20–7.52(4H, m), 7.79(1H, s), 8.42(1H, s), 8.88(1H, s), 10.70(1H, br), 13.76(1H, s).

EXAMPLE 60

3-Ethyl-8-(2-isopropylaminobenzylamino)-2,3-dihydro-1H-imidazo[4,5-g]quinazoline-2-one 2 hydrochloride (Compound 60)

According to an almost similar manner to that in Example 1, the title compound was obtained from the compound as the starting material obtained in Reference Example 63.

$^1$H-NMR (DMSO-d$_6$) δ (ppm): 1.25–1.33(9H, m), 3.75–3.90(1H, m), 3.95(2H, q, J=7.2 Hz), 4.27(1H, br), 4.97(2H, br), 7.00–7.48(4H, m), 7.49(1H, s), 8.18(1H, s), 8.86(1H, s), 10.60(1H, br), 12.00(1H, s).

EXAMPLE 61

3-Ethyl-8-(2-ethylaminobenzylamino)-2,3-dihydro-1H-imidazo[4,5-g]quinazoline-2-one 2 hydrochloride (Compound 61)

According to an almost similar manner to that in Example 1, the title compound was obtained from the compound as the starting material obtained in Reference Example 73.

$^1$H-NMR (DMSO-d$_6$) δ (ppm): 1.25–1.37(6H, m), 3.35–3.46(2H, m), 3.95(2H, q, J=7.3 Hz), 4.60(1H, br), 4.98(2H, br), 7.05–7.15(1H, m), 7.15–7.37(2H, m), 7.44 (1H, d, J=7.6 Hz), 7.52(1H, s), 8.23(1H, s), 8.85(1H, s), 10.71(1H, s), 12.01(1H, s).

EXAMPLE 62

3-Ethyl-8-(2-ethylaminobenzylamino)-2,3-dihydro-1H-imidazo[4,5-g]quinazoline-2-thione 2 hydrochloride (Compound 62)

According to an almost similar manner to that in Example 22, the title compound was obtained from the compound as the starting material obtained in Reference Example 73.

$^1$H-NMR (DMSO-d$_6$) δ (ppm): 1.28–1.34(6H, m), 3.18–3.31(2H, m), 4.20(1H, br), 4.36(2H, q, J=7.0 Hz), 4.95(2H, br), 6.85–7.20(2H, m), 7.25–7.40(2H, m), 7.72 (1H, s), 8.41(1H, s), 8.90(1H, s), 10.70(1H, br), 13.76(1H, s).

EXAMPLE 63

3-Ethyl-8-[2-(3-hydroxymethylpiperidino) benzylamino]-2,3-dihydro-1H-imidazo[4,5-g] quinazoline-2-thione 2 hydrochloride (Compound 63)

According to an almost similar manner to that in Example 22, the title compound was obtained from the compound as the starting material obtained in Reference Example 65.

$^1$H-NMR (DMSO-d$_6$) δ (ppm): 1.32(3H, t, J=7.1 Hz), 1.72–2.15(3H, m), 2.70–3.00(2H, m), 3.15–3.46(4H, m), 4.10–4.50(5H, m), 5.11(2H, d, J=5.0 Hz), 7.10–7.50(4H, m), 7.79(1H, s), 8.43(1H, s), 8.87(1H, s), 10.84(1H, br), 13.75 (1H, s).

EXAMPLE 64

8-(2-Cyclopentylaminobenzylamino)-3-ethyl-2,3-dihydro-1H-imidazo[4,5-g]quinazoline-2-thione 2 hydrochloride (Compound 64)

According to an almost similar manner to that in Example 22, the title compound was obtained from the compound as the starting material obtained in Reference Example 75.

$^1$H-NMR (DMSO-d$_6$) δ (ppm): 1.31(3H, t, J=7.1 Hz), 1.51–1.80(6H, m), 1.90–2.05(2H, m), 3.90–4.00(1H, m), 4.36(2H, q, J=7.1 Hz), 4.50(1H, br), 4.98(2H, br), 6.95–7.15 (2H, m), 7.28–7.35(2H, m), 7.74(1H, s), 8.41(1H, s), 8.91 (1H, s), 10.77(1H, s), 13.77(1H, s).

EXAMPLE 65

8-(2-Butylaminobenzylamino)-3-ethyl-2,3-dihydro-1H-imidazo[4,5-g]quinazoline-2-thione 2 hydrochloride (Compound 65)

According to an almost similar manner to that in Example 22, the title compound was obtained from the compound as the starting material obtained in Reference Example 77.

$^1$H-NMR (DMSO-d$_6$) δ (ppm): 0.91(3H, t, J=7.3 Hz), 1.28–1.42(5H, m), 1.64–1.72(2H, m), 3.21–3.27(2H, m), 4.35(2H, q, J=7.1 Hz), 4.50(1H, br), 4.94(2H, br), 6.90–7.05 (2H, m), 7.25–7.35(2H, m), 7.74(1H, s), 8.42(1H, s), 8.90 (1H, s), 10.79(1H, br), 13.78(1H, s).

EXAMPLE 66

3-Ethyl-8-[2-(1-pyrrolidinyl)benzylamino]-2,3-dihydro-1H-imidazo[4,5-g]quinazoline-2-one 2 hydrochloride (Compound 66)

According to an almost similar manner to that in Example 1, the title compound was obtained from the compound as the starting material obtained in Reference Example 79.

$^1$H-NMR (DMSO-d$_6$) δ (ppm): 1.28(3H, t, J=7.1 Hz), 2.05–2.17(4H, m), 3.45–3.60(2H, m), 3.96(2H, q, J=7.1 Hz), 3.96–4.00(2H, m), 5.08(2H, br), 7.07–7.45(4H, m), 7.50 (1H, s), 8.19(1H, s), 8.84(1H, s), 10.60(1H, br), 11.99(1H, s).

EXAMPLE 67

8-(2-Butylaminobenzylamino)-3-ethyl-2,3-dihydro-1H-imidazo[4,5-g]quinazoline-2-one 2 hydrochloride (Compound 67)

According to an almost similar manner to that in Example 1, the title compound was obtained from the compound as the starting material obtained in Reference Example 77.

$^1$H-NMR (DMSO-d$_6$) δ (ppm): 0.92(3H, t, J=7.4 Hz), 1.28(3H, t, J=7.1 Hz), 1.33–1.47(2H, m), 1.68–1.80(2H, m), 3.26–3.33(2H, m), 3.95(2H, q, J=7.1 Hz), 4.60(1H, br), 4.97(2H, d, J=4.3 Hz), 7.00–7.10(1H, m), 7.12–7.20(1H, m), 7.25–7.35(1H, m), 7.42(1H, d, J=7.3 Hz), 7.52(1H, s), 8.22(1H, s), 8.84(1H, s), 10.68(1H, t, J=4.3 Hz), 12.00(1H, s).

EXAMPLE 68

8-(2-Cyclohexylaminobenzylamino)-3-ethyl-2,3-dihydro-1H-imidazo [4,5-g]quinazoline-2-thione 2 hydrochloride (Compound 68)

According to an almost similar manner to that in Example 22, the title compound was obtained from the compound as the starting material obtained in Reference Example 81.

$^1$H-NMR (DMSO-d$_6$) δ (ppm): 1.24–1.46(7H, m), 1.48–1.67(2H, m), 1.70–1.82(2H, m), 2.03–2.08(2H, m), 3.44–3.52(1H, m), 4.20(1H, br), 4.36(2H,q, J=7.3 Hz), 5.02 (2H, s), 7.11–7.33(3H, m), 7.44–7.48(1H, m), 7.74(1H, s), 8.41(1H, s), 8.91(1H, s), 10.80(1H, s), 13.75(1H, s).

EXAMPLE 69

8-(2-Cyclohexylaminobenzylamino)-3-ethyl-2,3-dihydro-1H-imidazo[4,5-g]quinazoline-2-one 2 hydrochloride (Compound 69)

According to an almost similar manner to that in Example 1, the title compound was obtained from the compound as the starting material obtained in Reference Example 81.

¹H-NMR (DMSO-d₆) δ (ppm): 1.24–1.31(6H, m), 1.54–1.63(3H, m), 1.77–1.82(2H, m), 2.05–2.09(2H, m), 3.45–3.60(1H, m), 3.95(2H, q, J=6.9 Hz), 4.45(1H, br), 5.02(2H, d, J=4.6 Hz), 7.21–7.45(3H, m), 7.51–7.54(2H, m), 8.22(1H, s), 8.85(1H, s), 10.72(1H, t, J=4.6 Hz), 12.01(1H, s).

EXAMPLE 70

3-Ethyl-8-[2-(1-pyrrolidinyl)benzylamino]-2,3-dihydro-1H-imidazo[4,5-g]quinazoline-2-thione 2 hydrochloride (Compound 70)

According to an almost similar manner to that in Example 22, the title compound was obtained from the compound as the starting material obtained in Reference Example 79.

¹H-NMR (DMSO-d₆) δ (ppm): 1.31(3H, t, J=7.1 Hz), 2.05–2.25(4H, m), 3.60–3.85(4H, m), 4.36(2H, q, J=7.1 Hz), 5.17(2H, br), 7.27–7.45(1H, m), 7.48–7.65(3H, m), 7.76 (1H, s), 8.43(1H, s), 8.90(1H, s), 10.92(1H, br), 13.86(1H, s).

EXAMPLE 71

3-Ethyl-8-[2-(4-ethyl-1-piperazinyl)benzylamino]-2,3-dihydro-1H-imidazo[4,5-g]quinazoline-2-one 3 hydrochloride (Compound 71)

According to an almost similar manner to that in Example 1, the title compound was obtained from the compound obtained in Reference Example 83.

¹H-NMR (DMSO-d₆) δ (ppm): 1.25–1.36(6H, m), 3.18–3.46(8H, m), 3.54–3.58(2H, m), 3.95(2H, q, J=7.2 Hz), 5.03(2H, d, J=5.6 Hz), 7.10(1H, dd, J=7.6 Hz, 8.2 Hz), 7.22(1H, d, J=6.9 Hz), 7.28–7.34(2H, m), 7.57(1H, s), 8.26(1H, s), 8.80(1H, s), 10.51(1H, t, J=5.6 Hz), 12.05(1H, s).

EXAMPLE 72

3-Ethyl-8-[2-(2-methylpropylamino)benzylamino]-2,3-dihydro-1H-imidazo[4,5-g]quinazoline-2-one 2 hydrochloride (Compound 72)

According to an almost similar manner to that in Example 1, the title compound was obtained from the compound obtained in Reference Example 85.

¹H-NMR (DMSO-d₆) δ (ppm): 0.99(6H, d, J=6.9 Hz), 1.28(3H, t, J=7.1 Hz), 2.04–2.10(1H, m), 3.06–3.09(2H, m), 3.94(2H, q, J=7.1 Hz), 4.90(2H, d, J=5.3 Hz), 6.40(1H , br), 6.88–6.92(1H, m), 6.95–7.02(1H, m), 7.24(1H, dd, J=7.6 Hz, 7.6 Hz), 7.35(1H, d, J=7.3 Hz), 7.54(1H, s), 8.24(1H, s), 8.84(1H, s), 10.70(1H, t, J=5.3 Hz), 12.02(1H, s).

EXAMPLE 73

8-[2-(1-Perhydroazepinyl)benzylamino]-3-ethyl-2,3-dihydro-1H-imidazo[4,5-g]quinazoline-2-thione 2 hydrochloride (Compound 73)

According to an almost similar manner to that in Example 22, the title compound was obtained from the compound obtained in Reference Example 87.

¹H-NMR (DMSO-d₆) δ (ppm): 1.32(3H, t, J=7.1 Hz), 1.75–1.86(4H; m), 1.90–2.15(4H, m), 3.50–3.70(2H, m), 4.35(2H, q, J=7.1 Hz), 4.60–4.85(2H, br), 5.16(2H, br), 7.27–7.50(4H, m), 7.80(1H, s), 8.46(1H, s), 8.87(1H, s), 11.00(1H, s), 13.76(1H, s).

EXAMPLE 74

8-(2-Cyclopentylaminobenzylamino)-3-ethyl-2,3-dihydro-1H-imidazo[4,5-g]quinazoline-2-one 2 hydrochloride (Compound 74)

According to an almost similar manner to that in Example 1, the title compound was obtained from the compound obtained in Reference Example 75.

¹H-NMR (DMSO-d₆) δ (ppm): 1.27(3H, t, J=7.1 Hz), 1.55–1.72(2H, m), 1.75–1.90(4H, m), 1.93–2.00(2H, m), 3.94(2H, q, J=7.1 Hz), 3.95–4.00(1H, m), 5.00(2H, d, J=4.6 Hz), 5.20(1H, br), 7.09–7.20(1H, m), 7.27–7.40(2H, m), 7.42–7.50(1H, m), 7.54(1H, s), 8.23(1H, s), 8.85(1H, s), 10.72(1H, t, J=4.6 Hz), 12.01(1H, s).

EXAMPLE 75

3-Ethyl-8-[2-(1-tricyclo[3.3.1.1$^{3,7}$]decyl)aminobenzylamino]-2,3-dihydro-1H-imidazo[4,5-g]quinazoline-2-thione 2 hydrochloride (Compound 75)

According to an almost similar manner to that in Example 22, the title compound was obtained from the compound obtained in Reference Example 89.

¹H-NMR (DMSO-d₆) δ (ppm): 1.33(3H, t, J=7.1 Hz), 1.66–1.74(6H, m), 2.12–2.52(9H, m), 3.06(1H, br), 4.37 (2H, q, J=7.1 Hz), 5.20(2H, d, J=5.0 Hz), 7.46–7.54(3H, m), 7.65–7.68(1H, m), 7.78(1H, s), 8.41(1H, s), 8.95(1H, s), 10.94(1H, t, J=5.0 Hz), 13.76(1H, s).

EXAMPLE 76

3-Ethyl-8-{2-[4-(2-hydroxyethyl)piperidino]benzylamino}-2,3-dihydro-1H-imidazo[4,5-g]quinazoline-2-one 2 hydrochloride (Compound 76)

According to an almost similar manner to that in Example 9, the title compound was obtained from the compound obtained in Reference Example 69.

H-NMR (DMSO-d₆) δ (ppm): 1.30(3H, t, J=7.1 Hz), 1.46–1.72(4H, m), 1.75–1.90(2H, m), 2.70–3.40(7H, m), 3.97(2H, q, J=7.1 Hz), 5.08(2H, br), 6.40(1H, br), 7.10–7.40 (4H, m), 7.48(1H, s), 8.24(1H, s), 8.81(1H, s), 10.30(1H, br), 11.95(1H, s).

EXAMPLE 77

3-Ethyl-8-[2-[4-ethyl-1-piperazinyl)benzylamino]-2,3-dihydro-1H-imidazo[4,5-g]quinazoline-2-thione 3 hydrochloride (Compound 77)

According to an almost similar manner to that in Example 22, the title compound was obtained from the compound obtained in Reference Example 83.

¹H-NMR (DMSO-d₆) δ (ppm): 1.31–1.39(6H, m), 3.18–3.32(8H, m), 3.50–3.61(2H, m), 4.37(2H, q, J=7.3 Hz), 5.07(2H, d, J=5.6 Hz), 7.12(1H, dd, J=6.9 Hz, 7.9 Hz), 7.23–7.35(3H, m), 7.71(1H, s), 8.42(1H, s), 8.85(1H, s), 10.57(1H, t, J=5.6 Hz), 13.71(1H, s).

EXAMPLE 78

3-Ethyl-8-[2-(2-methylpropylamino)benzylamino]-2,3-dihydro-1H-imidazo[4,5-g]quinazoline-2-thione 2 hydrochloride (Compound 78)

According to an almost similar manner to that in Example 22, the title compound was obtained from the compound obtained in Reference Example 85.

¹H-NMR (DMSO-d₆) δ (ppm): 0.96(6H, d, J=6.6 Hz), 1.32(3H, t, J=7.1 Hz), 1.97–2.02(1H, m), 2.99–3.03(2H, m), 4.36(2H, q, J=7.1 Hz), 4.90(2H, d, J=4.6 Hz), 5.00(1H , br), 6.75–6.84(2H, m), 7.16–7.28(2H, m), 7.72(1H, s), 8.40(1H, s), 8.89(1H, s), 10.69(1H, t, J=4.6 Hz), 13.73(1H, s).

EXAMPLE 79

3-Ethyl-8-[2-(4-hydroxybutylamino)benzylamino]-2,3-dihydro-1H-imidazo[4,5-g]quinazoline-2-thione 2 hydrochloride (Compound 79)

According to an almost similar manner to that in Example 22, the title compound was obtained from the compound obtained in Reference Example 91.

¹H-NMR (DMSO-d₆) δ (ppm): 1.32(3H, t, J=6.9 Hz), 1.50–1.60(2H, m), 1.75–1.86(2H, m), 3.29–3.32(2H, m), 3.41–3.50(2H, m), 4.36(2H, q, J=6.9 Hz), 4.99(2H, br), 5.00(1H, br), 5.30(1H, br), 7.05–7.29(2H, m), 7.32(1H, dd, J=6.9 Hz, 8.6 Hz), 7.41(1H, d, J=7.3 Hz), 7.73(1H, s), 8.41(1H, s), 8.90(1H, s), 10.82(1H, s), 13.74(1H, s).

EXAMPLE 80

8-[2-(4-Hydroxymethylpiperidino)benzylamino]-3-propyl-2,3-dihydro-1H-imidazo[4,5-g]quinazoline-2-thione 2 hydrochloride (Compound 80)

According to an almost similar manner to that in Example 22, the title compound was obtained from the compound obtained in Reference Example 93.

¹H-NMR (DMSO-d₆) δ (ppm): 0.95(3H, t, J=7.4 Hz), 1.50–2.00(7H, m), 3.20–3.70(6H, m), 4.28(2H, t, J=7.1 Hz), 5.15(2H, br), 5.70(1H, br), 7.20–7.55(4H, m), 7.82(1H, s), 8.43(1H, s), 8.88(1H, s), 10.45(1H, br), 13.76(1H, s).

EXAMPLE 81

3-[2-(1-Perhydroazepinyl)benzylamino]-3-ethyl-2,3-dihydro-1H-imidazo[4,5-g]quinazoline-2-one 2 hydrochloride (Compound 81)

According to an almost similar manner to that in Example 1, the title compound was obtained from the compound obtained in Reference Example 87.

¹H-NMR (DMSO-d₆) δ (ppm): 1.30(3H, t, J=7.3 Hz), 1.70–1.90(4H, m), 1.95–2.10(4H, m), 3.50–3.70(4H, m), 3,96(2H, q, J=7.3 Hz), 5.14(2H, br), 7.26–7.80(5H, m), 8.22(1H, s), 8.81(1H, s), 10.60(1H, s), 11.99(1H, s).

EXAMPLE 82

3-Ethyl-8-[2-(4-methyl-1-homopiperazinyl)benzylamino]-2,3-dihydro-1H-imidazo[4,5-g]quinazoline-2-thione 3 hydrochloride (Compound 82)

According to an almost similar manner to that in Example 22, the title compound was obtained from the compound obtained in Reference Example 95.

¹H-NMR (DMSO-d₆) (ppm): 1.34(3H, t, J=7.1 Hz), 2.09–2.15(1H, m), 2.27–2.33(1H, m), 2.88(3H, s), 3.14–3.20(2H, m), 3.29–3.46(2H, m), 3.47–3.59(4H, m), 4.37(2H, q, J=7.1 Hz), 5.09(2H, d, J=5.6 Hz), 7.02–7.09(1H, m), 7.28–7.31(3H, m), 7.74(1H, s), 8.47(1H, s), 8.85(1H, s), 10.65(1H, t, J=5.6 Hz), 13.73(1H, s).

EXAMPLE 83

3-Ethyl-8-{2-[2-(2-hydroxyethoxy)ethylamino]benzylamino}-2,3-dihydro-1H-imidazo[4,5-g]quinazoline-2-thione 2 hydrochloride (Compound 83)

According to an almost similar manner to that in Example 22, the title compound was obtained from the compound obtained in Reference Example 97.

¹H-NMR (DMSO-d₆) δ (ppm): 1.33(3H, t, J=7.3 Hz), 3.41–3.52(6H, m), 3.72(2H, t, J=5.3 Hz), 4.36(2H, q, J=7.3 Hz), 4.91(2H, d, J=5.3 Hz), 5.55(2H, br), 6.86–7.00(2H, m), 7.25(1H, dd, J=7.3 Hz, 7.9 Hz), 7.35(1H, d, J=7.9 Hz), 7.70(1H, s), 8.39(1H, s), 8.92(1H, s), 10.72(1H, t, J=5.3 Hz), 13.72(1H, s).

EXAMPLE 84

3-Ethyl-8-[2-(4-methyl-1-homopiperazinyl)benzylamino]-2,3-dihydro-1H-imidazo[4,5-g]quinazoline-2-one 3 hydrochloride (Compound 84)

According to an almost similar manner to that in Example 1, the title compound was obtained from the compound obtained in Reference Example 95.

¹H-NMR (DMSO-d₆) δ (ppm): 1.28(3H, t, J=7.3 Hz), 2.12–2.17(1H, m), 2.25–2.32(1H, m), 2.84(3H, s), 3.12–3.18(2H, m), 3.31–3.61(6H, m), 3.94(2H, q, J=7.3 Hz), 5.05(2H, d, J=5.6 Hz), 7.04–7.10(1H, m), 7.27–7.33(3H, m), 7.56(1H, s), 8.28(1H, s), 8.79(1H, s), 10.51(1H, t, J=5.6 Hz), 12.02(1H, s).

EXAMPLE 85

8-[2-(4-Hydroxymethylpiperidino)benzylamino]-3-methyl-2,3-dihydro-1H-imidazo[4,5-g]quinazoline-2-thione 2 hydrochloride (Compound 85)

According to an almost similar manner to that in Example 22, the title compound was obtained from the compound obtained in Reference Example 99.

¹H-NMR (DMSO-d₆) δ (ppm): 1.56–1.87(5H, m), 3.00–3.50(7H, m), 3.74(3H, s), 5.10(2H, br), 7.13–7.37(4H, m), 7.69(1H, s), 8.39(1H, s), 8.87(1H, s), 10.60(1H, br), 13.72(1H, s).

EXAMPLE 86

3-Ethyl-8-[2-(2-furylmethylamino)benzylamino]-2,3-dihydro-1H-imidazo[4,5-g]quinazoline-2-thione 2 hydrochloride (Compound 86)

According to an almost similar manner to that in Example 22, the title compound was obtained from the compound obtained in Reference Example 101.

¹H-NMR (DMSO-d₆) δ (ppm): 1.30(3H, t, J=7.1 Hz), 4.30–4.46(4H, m), 4.83(2H, d, J=5.3 Hz), 6.03(1H, br), 6.30–6.37(2H, m), 6.66(1H, dd, J=7.3 Hz, 8.6 Hz), 6.77(1H, d, J=8.2 Hz), 7.12(1H, d, J=8.2 Hz, 8.6 Hz), 7.20(1H, d, J=7.3 Hz), 7.50(1H, s), 7.78(1H, s), 8.44(1H, s), 8.81(1H, s), 10.79(1H, t, J=5.3 Hz), 13.81(1H, s).

EXAMPLE 87

3-Ethyl-8-[2-(1,2,3,4-tetrahydroisoquinoline-2-yl)benzylamino]-2,3-dihydro-1H-imidazo[4,5-g]quinazoline-2-thione 1 hydrochloride (Compound 87)

According to an almost similar manner to that in Example 22, the title compound was obtained from the compound obtained in Reference Example 103.

¹H-NMR (DMSO-d₆) δ (ppm): 1.31(3H, t, J=7.1 Hz), 2.95–3.03(2H, m), 3.25–3.37(2H, m), 4.18(2H, br), 4.34(2H, q, J=7.1 Hz), 5.10(2H, d, J=5.0 Hz), 7.10–7.15(5H, m), 7.32–7.40(3H, m), 7.76(1H, s), 8.42(1H, s), 8.76(1H, s), 10.68(1H, t, J=5.0 Hz), 13.77(1H, s).

EXAMPLE 88

3-Ethyl-8-[2-(2-tetrahydrofurylmethylamino)benzylamino]-2,3-dihydro-1H-imidazo[4,5-g]quinazoline-2-thione 2 hydrochloride (Compound 88)

According to an almost similar manner to that in Example 22, the title compound was obtained from the compound obtained in Reference Example 105.

¹H-NMR (DMSO-d₆) δ (ppm): 1.37(3H, t, J=7.1 Hz), 1.51–1.70(1H, m), 1.75–2.00(3H, m), 3.05–3.35(2H, m), 3.60–3.80(2H, m), 4.02–4.15(1H, m), 4.35(2H, q, J=7.1 Hz), 4.90(2H, br), 5.10(1H, br), 6.70–6.83(2H, m), 7.15–7.25(2H, m), 7.75(1H, s), 8.42(1H, s), 8.82(1H, s), 10.50(1H, s), 13.77(1H, s).

EXAMPLE 89

3-Ethyl-8-[2-(2-thienyl)methylamino)benzylamino]-2,3-dihydro-1H-imidazo[4,5-g]quinazoline-2-thione 2 hydrochloride (Compound 89)

According to an almost similar manner to that in Example 22, the title compound was obtained from the compound obtained in Reference Example 107.

$^1$H-NMR (DMSO-d$_6$) δ (ppm): 1.32(3H, t, J=7.3 Hz), 4.36(2H, q, J=7.3 Hz), 4.57(2H, br), 4.85(2H, d, J=4.6 Hz), 5.60(1H, br), 6.60–6.78(2H, m), 6.91–6.95(1H, m), 7.04–7.50(4H, m), 7.69(1H, s), 8.39(1H, s), 8.74(1H, s), 10.60(1H, t, J=4.6 Hz), 13.73(1H, s).

EXAMPLE 90

3-Ethyl-8-[2-(2-phenylaminoethylamino) benzylamino]-2,3-dihydro-1H-imidazo[4,5-g] quinazoline-2-thione 3 hydrochloride (Compound 90)

According to an almost similar manner to that in Example 22, the title compound was obtained from the compound obtained in Reference Example 109.

$^1$H-NMR (DMSO-d$_6$) δ (ppm): 1.33(3H, t, J=7.0 Hz), 3.45–3.55(4H, m), 4.36(2H, q, J=7.0 Hz), 4.89(2H, d, J=5.3 Hz), 5.20(2H, br), 6.63–6.75(2H, m), 7.12–7.36(7H, m), 7.66(1H, s), 8.46(1H, s), 8.86(1H, s), 10.70(1H, br), 13.71 (1H, s).

EXAMPLE 91

3-Ethyl-8-[2-(4-methoxymethylpiperidino) benzlamino]- 2,3-dihydro-1H-imidazo[4,5-g] quinazoline-2-thione 2 hydrochloride (Compound 91)

According to an almost similar manner to that in Example 22, the title compound was obtained from the compound obtained in Reference Example 112.

$^1$H-NMR (DMSO-d$_6$) δ (ppm): 1.32(3H, t, J=7.1 Hz), 1.50–2.00(5H, m), 2.60–3.20(2H, m), 3.25–3.50(7H, m), 4.35(2H, q, J=7.1 Hz), 5.10(2H, br), 7.05–7.50(4H, m), 7.77(1H, s), 8.41(1H, s), 8.87(1H, s), 10.60(1H, br), 13.76 (1H, s).

EXAMPLE 92

8-[2-(4-Ethoxymethylpiperidino)benzylamino]-3-ethyl-2,3-dihydro-1H-imidazo[4,5-g]quinazoline-2-thione 2 hydrochloride (Compound 92)

According to an almost similar manner to that in Example 22, the title compound was obtained from the compound obtained in Reference Example 114.

$^1$H-NMR (DMSO-d$_6$) δ (ppm): 1.15(3H, t, J=6.9 Hz), 1.33(3H, t, J=7.1 Hz), 1.50–2.00(5H, m), 3.10–3.50(8H, m), 4.36(2H, q, J=7.1 Hz), 5.13(2H, br), 7.19–7.39(4H, m), 7.77(1H, s), 8.42(1H, s), 8.87(1H, s), 10.77(1H, br), 13.73 (1H, s).

EXAMPLE 93

8-(2-Aminobenzylamino)-3-ethyl-2,3-dihydro-1H-imidazo[4,5-g]quinazoline-2-thione 2 hydrochloride (Compound 93)

The compound (0.58 g, 1.29 mmol) obtained in Reference Example 117 was suspended in methanol (40 ml), and 4 N hydrochloric acid-ethyl acetate (10 ml) was added dropwise to the mixture under cooling on ice. After the addition was completed, the temperature of the mixture was gradually raised, and it was stirred at room temperature for 1 hour. After the reaction was completed, the solution was concentrated, and the precipitated solids were filtered off and washed with methanol-ether and dried to give the title compound.

$^1$H-NMR (DMSO-d$_6$) δ (ppm): 1.32(3H, t, J=7.1 Hz), 3.93(2H, br), 4.36(2H, q, J=7.1 Hz), 5.03(2H, s), 7.14–7.19 (1H, m), 7.29–7.41(3H, m), 7.71(1H, s), 8.42(1H, s), 8.91 (1H, s), 10.75(1H, br), 13.76(1H, s).

EXAMPLE 94

8-(2-Cyclobutylaminobenzylamino)-3-ethyl-2,3-dihydro-1H-imidazo[4,5-g]quinazoline-2-thione 2 hydrochloride (Compound 94)

According to an almost similar manner to that in Example 22, the title compound was obtained from the compound obtained in Reference Example 119.

$^1$H-NMR (DMSO-d$_6$) δ (ppm): 1.31(3H, t, J=7.1 Hz), 1.74–1.85(2H, m), 2.16–2.33(4H, m), 4.01–4.08(1H, m), 4.35(2H, q, J=7.1 Hz), 4.95(2H, d, J=4.6 Hz), 5.20 (1H, br), 6.90–7.00(2H, m), 7.24(1H, dd, J=7.6 Hz, 7.9 Hz), 7.32(1H, d, J=7.6 Hz), 7.77(1H, s), 8.45(1H, s), 8.91(1H, s), 10.85 (1H, t, J=4.6 Hz), 13.76(1H, s).

EXAMPLE 95

8-[2-exo-(2-Bicyclo[2.2.1]heptylamino) benzylamino]-3-ethyl-2,3-dihydro-1H-imidazo[4,5-g]quinazoline-2-thione 2 hydrochloride (Compound 95)

According to an almost similar manner to that in Example 22, the title compound was obtained from the compound obtained in Reference Example 121.

$^1$H-NMR(DMSO-d$_6$) δ (ppm): 1.08–1.21(4H, m), 1.32 (3H, t, J=7.1 Hz), 1.49–1.60(4H, m), 1.70–1.78(1H, m), 2.25–2.32(2H, m), 3.34–3.38(1H, m), 4.36(2H, q, J=7.1 Hz), 4.92(2H, d, J=4.6 Hz), 6.79–6.85(2H, m), 7.21(1H, dd, J=7.6 Hz, 7.6 Hz), 7.28(1H, d, J=7.3 Hz), 7.72(1H, s), 8.38(1H, s), 8.90(1H, s), 10.68(1H, t, J=4.6 Hz), 13.73(1H, s).

EXAMPLE 96

8-[2-(4-Ethoxycarbonyl-1-piperazinyl) benzylamino]-3-ethyl-2,3-dihydro-1H-imidazo[4,5-g]quinazoline-2-thione 2 hydrochloride (Compound 96)

According to an almost similar manner to that in Example 22, the title compound was obtained from the compound obtained in Reference Example 71.

$^1$H-NMR(as free base, DMSO-d$_6$) δ (ppm): 1.24(3H, t, J=7.1 Hz), 1.34(3H, t, J=7.1 Hz), 2.88–2.93(4H, m), 3.50–3.60(4H, m), 4.09(2H, q, J=7.1 Hz), 4.36(2H, q, J=7.1 Hz), 4.93(2H, d, J=5.3 Hz), 7.02(1H, dd, J=7.3 Hz, 7.3 Hz), 7.13(1H, d, J=7.3 Hz ), 7.20–7.27(2H, m), 7.56(1H, s), 8.14(1H, s), 8.42(1H, s), 8.85(1H, t, J=5.3 Hz), 13.22(1H, s).

Pharmaceutical Preparation 1 (Tablets)

Tablets with the following composition were prepared in a usual manner.

| | |
|---|---|
| Compound 33 | 100 mg |
| Lactose | 60 mg |
| Potato starch | 30 mg |
| Polyvinyl alcohol | 2 mg |
| Magnesium stearate | 1 mg |
| Tar pigment | trace |

Pharmaceutical Preparation 2 (Powder)
Powder with the following composition was prepared in a usual manner.

| Compound 34 | 150 mg |
|---|---|
| Lactose | 280 mg |

Pharmaceutical Preparation 3 (Syrup)
A syrup with the following composition was prepared in a usual manner.

| Compound 33 | 100 mg |
|---|---|
| Refined white sugar | 40 g |
| Ethyl p-hydroxybenzoate | 40 mg |
| Propyl p-hydroxybenzoate | 10 mg |
| Strawberry flavor | 0.1 cc |

The total amount was adjusted to 100 cc by adding water.

Industrial Applicability

According to the present invention, there are provided imidazoquinazoline derivatives or pharmaceutically acceptable salts thereof which have potent and selective cyclic guanosine 3',5'-monophosphate (cGMP) specific phosphodiesterase (PDE) inhibitory activity, increases the concentration of intracellular cGMP, enhances the effects of endothelium-derived relaxing factor (EDRF), nitro vasodilator or atrial natriuretic peptide, shows the anti-platelet activity, the anti-vasocontraction activity and the vasodilating activity, and are useful for treating or ameliorating cardiovascular diseases such as thrombosis, angina pectoris, hypertension, congestive heart failure, post-PTCA restenosis, peripheral vascular diseases, arterial sclerosis etc., inflammatory allergic diseases such as bronchitis, chronic asthma, allergic asthma, allergic coryza etc., alimentary canal diseases such as irritable intestine syndrome etc., glaucoma, impotence and the like.

What is claimed is:
1. An imidazoquinazoline derivative represented by formula (I):

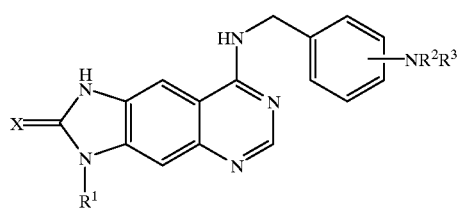

(I)

wherein
R$^1$ represents hydrogen, lower alkyl, cycloalkyl, bicycloalkyl, tricycloalkyl, benzocycloalkenyl, lower alkenyl, aralkyl, aryl, or heteroaryl selected from the group consisting of pyridyl, quinolyl, isoquinolyl, thienyl, furyl, pyrrolyl, benzothienyl, benzofuryl, indolyl, tetrahydroquinolyl, tetrahydroisoquinolyl and imidazolinyl, R$^2$ is lower alkyl;
R$^3$ is a hydroxy-containing lower alkyl; and
X represents O or S,
wherein said lower alkyl, cycloalkyl, bicycloalkyl and tricycloalkyl may be independently substituted with, the same or different, 1 to 3 substituents selected from the group consisting of cycloalkyl, hydroxy, lower alkoxy, hydroxyalkoxy, carboxy, lower alkoxycarbonyl, amino, monoalkyl-substituted amino, dialkyl-substituted amino, monoaryl-substituted amino, diaryl-substituted amino, nitro, halogen, heteroaryl (wherein said heteroaryl is selected from the group consisting of pyridyl, quinolyl, isoquinolyl, thienyl, furyl, pyrrolyl, benzothienyl, benzofuryl, indolyl, tetrahydroquinolyl, tetrahydroisoquinolyl and imidazolinyl; and said heteroaryl is optionally substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl) and alicyclic heterocyclic group (wherein said alicyclic heterocyclic group is selected from the group consisting of tetrahydrofuryl, piperidino, piperidyl, morpholino, morpholinyl, thiomorpholino, thiomorpholinyl, piperazinyl, homopiperazinyl, pyrrolidinyl, imidazolyl and tetrahydroisoquinolyl; and said alicyclic heterocyclic group is optionally substituted with substituents selected from the group consisting of lower alkyl, aryl and aralkyl); and said benzocycloalkenyl, lower alkenyl, aralkyl, aryl, heteroaryl and N-containing heterocyclic group may be independently substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl,
or a pharmaceutically acceptable salt thereof.

2. An imidazoquinazoline derivative represented by formula (I):

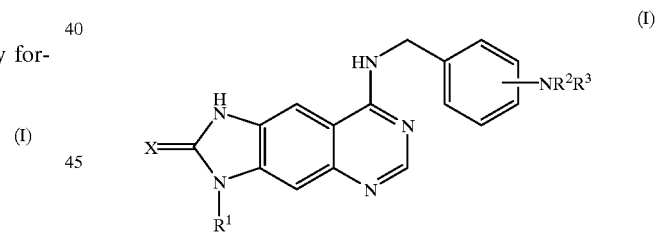

(I)

wherein
R$^1$ represents hydrogen, lower alkyl, cycloalkyl, bicycloalkyl, tricycloalkyl, benzocycloalkenyl, lower alkenyl, aralkyl, aryl, or heteroaryl selected from the group consisting of pyridyl, quinolyl, isoquinolyl, thienyl, furyl, pyrrolyl, benzothienyl, benzofuryl, indolyl, tetrahydroquinolyl, tetrahydroisoquinolyl and imidazolinyl, (wherein said lower alkyl, cycloalkyl, bicycloalkyl and tricycloalkyl may be independently substituted with, the same or different, 1 to 3 substituents selected from the group consisting of cycloalkyl, hydroxy, lower alkoxy, hydroxyalkoxy, carboxy, lower alkoxycarbonyl, amino, monoalkyl-substituted amino, dialkyl-substituted amino, monoaryl-substituted amino, diaryl-substituted amino, nitro, halogen, heteroaryl (wherein said heteroaryl is selected from the group consisting of pyridyl, quinolyl, isoquinolyl, thienyl, furyl, pyrrolyl, benzothienyl, benzofuryl, indolyl, tetrahydroquinolyl, tetrahydroisoquinolyl and imidazolinyl; and said heteroaryl is optionally substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl) and alicyclic heterocyclic group (wherein said alicyclic heterocyclic group is selected from the group consisting of tetrahydrofuryl, piperidino, piperidyl, morpholino, morpholinyl, thiomorpholino, thiomorpholinyl, piperazinyl, homopiperazinyl, pyrrolidinyl, imidazolyl and tetrahydroisoquinolyl; and said alicyclic heterocyclic group is optionally substituted with substituents selected from the group consisting of lower alkyl, aryl and aralkyl); and said benzocycloalkenyl, lower alkenyl, aralkyl, aryl and heteroaryl may be independently substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl), $R^2$ and $R^3$ are combined to represent an N-containing heterocyclic group selected from the group consisting of pyrrolidinyl, piperidino, piperazinyl, morpholino, thiomorpholino, homopiperazinyl, imidazolyl, 1-perhydroazepinyl, 1-perhydroazocinyl and tetrahydroisoquinolyl, (wherein said N-containing heterocyclic group is optionally substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl), X represents O or S, or a pharmaceutically acceptable salt thereof.

3. An imidazoquinazoline derivative represented by formula (I):

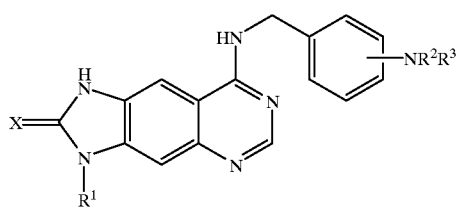

(I)

wherein $R^1$ represents lower alkyl which is optionally substituted with, the same or different, 1 to 3 substituents selected from the group consisting of cycloalkyl, hydroxy, lower alkoxy, hydroxyalkoxy, carboxy, lower alkoxycarbonyl, amino, monoalkyl-substituted amino, dialkyl-substituted amino, monoaryl-substituted amino, diaryl-substituted amino, nitro, halogen, optionally substituted herteroaryl (wherein said heteroaryl is selected from the group consisting of pyridyl, quinolyl, isoquinolyl, thienyl, furyl, pyrrolyl, benzothienyl, benzofuryl, indolyl, tetrahydroquinolyl, tetrahydroiso-quinolyl and imidazolinyl; and said heteroaryl is optionally substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl) and optionally substituted alicyclic heterocyclic group (wherein said alicyclic heterocyclic group is selected from the group consisting of tetrahydrofuryl, piperidino, piperidyl, morpholino, morpholinyl, thiomorpholino, thiomorpholinyl, piperazinyl, homopiperazinyl, pyrrolidinyl, imidazolyl and tetrahydroisoquinolyl; and said alicyclic heterocyclic group is optionally substituted with substituents selected from the group consisting of lower alkyl, aryl and aralkyl);

$R^2$ and $R^3$ are combined to represent an N-containing heterocyclic group selected from the group consisting of pyrrolidinyl, piperidino, piperazinyl, morpholino, thiomorpholino, homopiperazinyl, imidazolyl, 1-perhydroazepinyl, 1-perhydroazocinyl and tetrahydroisoquinolyl, (wherein said N-containing heterocyclic group is optionally substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl);

X represents O or S, or a pharmaceutically acceptable salt thereof.

4. A compound according to claim 2 wherein X is S.

5. A compound according to claim 3 wherein X is S.

6. A compound according to claim 1 wherein X is S.

7. A compound according to claim 6, wherein $R^1$ is lower alkyl.

8. A compound according to claim 4 wherein $R^1$ is lower alkyl.

9. A compound according to claim 5, wherein $R^1$ is lower alkyl.

10. A compound according to claim 1 wherein X is O.

11. A compound according to claim 10 wherein $R^1$ is a lower alkyl.

12. An imidazoquinazoline derivative represented by formula (I):

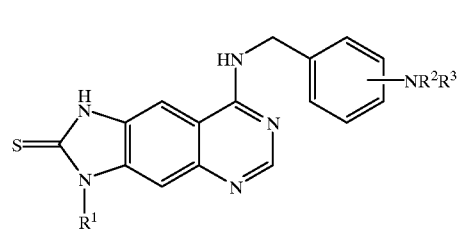

(I)

wherein $R^1$ is lower alkyl, $R^2$ is hydrogen, $R^3$ is lower alkyl; and wherein said lower alkyl may be independently substituted with 1 to 3 substituents selected from the group consisting of cycloalkyl, hydroxy, lower alkoxy, hydroxyalkoxy, carboxy, lower alkoxycarbonyl, amino, monoalkyl-substituted amino, dialkyl-substituted amino, monoaryl-substituted amino, diaryl-substituted amino, nitro, halogen, optionally substituted heteroaryl (said heteroaryl being selected from the group consisting of pyridyl, quinolyl, isoquinolyl, thienyl, furyl, pyrrolyl, benzothienyl, benzofuryl, indolyl, tetrahydroquinolyl, tetrahydroisoquinolyl and imidazolinyl, wherein said heteroaryl may be independently substituted with, the same or different, 1 to 5 substituents selected from the group consisting of lower alkyl, hydroxy, hydroxy-containing lower alkyl, lower alkoxy, lower alkoxyalkyl, carboxy, lower alkoxycarbonyl, amino, monoalkyl-substituted amino, dialkyl-substituted amino, nitro, sulfonamido, halogen and trifluoromethyl) and optionally substituted alicyclic heterocyclic group (said alicyclic heterocyclic group being selected from the group consisting of tetrahydrofuryl, piperidino, piperidyl, morpholino, morpholinyl, thiomorpholino, thiomorpholinyl, piperazinyl, homopiperazinyl, pyrrolidinyl, imidazolyl and tetrahydroisoquinoly, wherein said alicyclic heterocyclic group may be independently substituted with substituents selected from the group consisting of lower alkyl, aryl and aralkyl), or a pharmaceutically acceptable salt thereof.

13. An imidazoquinazoline derivative represented by formula (I):

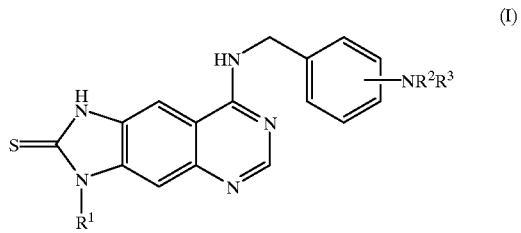

wherein $R^1$ is lower alkyl, $R^2$ is hydrogen, and $R^3$ is lower alkyl, or a pharmaceutically acceptable salt thereof.

* * * * *